(12) United States Patent
Korb et al.

(10) Patent No.: US 10,716,465 B2
(45) Date of Patent: *Jul. 21, 2020

(54) METHODS AND APPARATUSES FOR DETERMINING CONTACT LENS INTOLERANCE IN CONTACT LENS WEARER PATIENTS BASED ON DRY EYE TEAR FILM CHARACTERISTIC ANALYSIS AND DRY EYE SYMPTOMS

(71) Applicant: TearScience, Inc., Morrisville, NC (US)

(72) Inventors: Donald R. Korb, Boston, MA (US); Stephen M. Grenon, Durham, NC (US); Steve Bacich, Half Moon Bay, CA (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 159 days.

This patent is subject to a terminal disclaimer.

(21) Appl. No.: 15/892,549

(22) Filed: Feb. 9, 2018

(65) Prior Publication Data

US 2018/0177391 A1    Jun. 28, 2018

Related U.S. Application Data

(63) Continuation of application No. 14/268,647, filed on May 2, 2014, now Pat. No. 9,888,839, which is a (Continued)

(51) Int. Cl.
*A61B 3/00* (2006.01)
*A61B 3/10* (2006.01)
*G06T 7/00* (2017.01)

(52) U.S. Cl.
CPC ............ *A61B 3/0025* (2013.01); *A61B 3/101* (2013.01); *G06T 7/0012* (2013.01); *G06T 2207/30041* (2013.01)

(58) Field of Classification Search
CPC .......... A61B 7/101; A61B 7/00–7/185; A61B 3/101; A61B 3/00–3/185; G06T 7/0012; G06T 7/10–7/194
(Continued)

(56) References Cited

U.S. PATENT DOCUMENTS 3,941,901 A    3/1976 Harsch
3,971,952 A    7/1976 Inbar et al.
(Continued)

FOREIGN PATENT DOCUMENTS

CN    101663064 A    3/2010
CN    202891897 U    4/2013
(Continued)

OTHER PUBLICATIONS

Korb, Donald R. et al., "Increase in Tear Film Lipid Layer Thickness Following Treatment of Meibomian Gland Dysfunction," Adv. Exp. Med. Biol., vol. 350, 1994, pp. 293-298.
(Continued)

*Primary Examiner* — Zachary W Wilkes

(57) ABSTRACT

Methods and apparatuses for determining contact lens intolerance in contact lens wearer patients based on tear film characteristics analysis and dry eye symptoms are disclosed. In embodiments herein, imaging of the ocular tear film is performed during contact lens wear. An analysis of the image of the ocular tear film is performed to determine one or more tear film characteristics of the ocular tear film. The tear film characteristics can be used to determine the effect or possible effect of contact lens wear on the ocular tear film, and thus be used to determine contact lens intolerance of the patient. The tear film characteristics used to analyze contact lens intolerance based on images of the ocular tear film involving contact lens wear may include dry eye symptoms, including but not limited to tear film (e.g., lipid and/or aqueous) thickness, tear film viscosity, and tear film movement rate in the eye.

27 Claims, 56 Drawing Sheets
(23 of 56 Drawing Sheet(s) Filed in Color)

Related U.S. Application Data continuation-in-part of application No. 12/798,275, filed on Apr. 1, 2010, now Pat. No. 8,746,883.

(60) Provisional application No. 61/819,125, filed on May 3, 2013, provisional application No. 61/904,562, filed on Nov. 15, 2013, provisional application No. 61/211,596, filed on Apr. 1, 2009.

(58) Field of Classification Search
USPC .......... 351/205–206, 246–247, 219; 382/128
See application file for complete search history.

(56) References Cited

U.S. PATENT DOCUMENTS

| | | |
|---|---|---|
| 4,122,348 A | 10/1978 | Bruck |
| 4,533,223 A | 8/1985 | Duparchy |
| 4,588,883 A | 5/1986 | Abbas |
| 4,597,648 A | 7/1986 | Feldon et al. |
| 4,705,037 A | 11/1987 | Peyman et al. |
| 4,747,683 A | 5/1988 | Doane |
| 4,842,401 A | 6/1989 | Maurice |
| 4,885,352 A | 12/1989 | Erickson |
| 4,938,584 A | 7/1990 | Suematsu et al. |
| 5,110,200 A | 5/1992 | Snook |
| D330,769 S | 11/1992 | Blaha et al. |
| 5,216,456 A | 6/1993 | Volk |
| 5,258,791 A | 11/1993 | Penney et al. |
| 5,268,305 A | 12/1993 | Ribi et al. |
| 5,427,915 A | 6/1995 | Ribi et al. |
| 5,475,452 A | 12/1995 | Kuhn et al. |
| 5,491,097 A | 2/1996 | Ribi et al. |
| 5,494,829 A | 2/1996 | Sandstrom et al. |
| 5,571,568 A | 11/1996 | Ribi et al. |
| 5,621,523 A | 4/1997 | Oobayashi et al. |
| 5,622,872 A | 4/1997 | Ribi |
| 5,625,428 A | 4/1997 | Isogai |
| 5,626,134 A | 5/1997 | Zuckerman |
| 5,642,137 A | 6/1997 | Kitazumi |
| 5,647,032 A | 7/1997 | Jutamulia |
| 5,712,721 A | 1/1998 | Large |
| 5,719,659 A | 2/1998 | Suzuki |
| D394,505 S | 5/1998 | Hayashi |
| 5,760,950 A | 6/1998 | Maly et al. |
| 5,886,767 A | 3/1999 | Snook |
| 5,988,815 A | 11/1999 | Maus et al. |
| 6,059,773 A | 5/2000 | Maloney et al. |
| 6,088,470 A | 7/2000 | Camus et al. |
| 6,127,183 A | 10/2000 | Ivarsson et al. |
| 6,198,540 B1 | 3/2001 | Ueda et al. |
| 6,213,605 B1 | 4/2001 | D'Souza et al. |
| 6,236,459 B1 | 5/2001 | Negandaripour |
| 6,299,305 B1 | 10/2001 | Miwa |
| 6,394,603 B2 | 5/2002 | Miwa et al. |
| 6,447,119 B1 | 9/2002 | Stewart et al. |
| 6,450,641 B2 | 9/2002 | D'Souza et al. |
| D465,850 S | 11/2002 | Takizawa |
| D472,637 S | 4/2003 | Cooper et al. |
| 6,613,041 B1 | 9/2003 | Schründer |
| 6,659,613 B2 | 12/2003 | Applegate et al. |
| 6,685,320 B2 | 2/2004 | Hirohara et al. |
| 6,736,507 B2 | 5/2004 | Kudryashov et al. |
| 6,964,814 B2 | 11/2005 | Fujii et al. |
| 7,073,906 B1 | 7/2006 | Portney |
| 7,121,666 B2 | 10/2006 | Tseng et al. |
| 7,144,111 B1 | 12/2006 | Ross, III et al. |
| D552,736 S | 10/2007 | Yamaoka |
| 7,278,740 B1 | 10/2007 | Suzuki et al. |
| 7,281,801 B2 | 10/2007 | Wang |
| 7,431,458 B2 | 10/2008 | Jongsma et al. |
| D582,556 S | 12/2008 | Yamaoka |
| 7,611,245 B2 | 11/2009 | Carbonari |
| D607,562 S | 1/2010 | Heine et al. |
| 7,654,669 B2 | 2/2010 | Suzuki |
| 7,688,453 B2 | 3/2010 | Williby et al. |
| D614,774 S | 4/2010 | Gausmann et al. |
| 7,758,190 B2 | 7/2010 | Korb et al. |
| 7,771,353 B2 | 8/2010 | Luce |
| 7,982,881 B2 | 7/2011 | Fercher et al. |
| 7,988,294 B2 | 8/2011 | Korb et al. |
| 8,092,023 B2 | 1/2012 | Korb et al. |
| 8,192,026 B2 | 6/2012 | Gravely et al. |
| 8,215,774 B2 | 7/2012 | Korb et al. |
| 8,249,695 B2 | 8/2012 | Grenon et al. |
| 8,255,039 B2 | 8/2012 | Gravely et al. |
| 8,545,017 B2 | 10/2013 | Korb et al. |
| 8,585,204 B2 | 11/2013 | Gravely et al. |
| 8,591,033 B2 | 11/2013 | Korb et al. |
| 8,602,557 B2 | 12/2013 | Huth et al. |
| 8,610,976 B1 | 12/2013 | Cook et al. |
| 8,617,229 B2 | 12/2013 | Korb et al. |
| 8,641,194 B2 | 2/2014 | Primeau et al. |
| 8,746,883 B2 | 6/2014 | Korb et al. |
| 8,888,286 B2 | 11/2014 | Grenon et al. |
| 8,915,592 B2 | 12/2014 | Korb et al. |
| 9,173,558 B2 | 11/2015 | Huth et al. |
| 9,320,439 B2 | 4/2016 | Arita et al. |
| 9,339,177 B2 | 5/2016 | Grenon et al. |
| 9,456,741 B2 | 10/2016 | Huth et al. |
| 9,642,520 B2 | 5/2017 | Korb et al. |
| 9,662,008 B2 | 5/2017 | Korb et al. |
| 9,668,647 B2 | 6/2017 | Grenon et al. |
| 9,693,682 B2 | 7/2017 | Korb et al. |
| 9,888,839 B2 * | 2/2018 | Korb ..................... A61B 3/101 |
| 9,999,346 B2 | 6/2018 | Korb et al. |
| 2001/0055095 A1 | 12/2001 | D'Souza et al. |
| 2002/0039234 A1 | 4/2002 | Iwamoto |
| 2002/0049374 A1 | 4/2002 | Abreu |
| 2002/0180929 A1 | 12/2002 | Tseng et al. |
| 2003/0056281 A1 | 3/2003 | Hasegawa |
| 2004/0212781 A1 | 10/2004 | Mihashi et al. |
| 2005/0096431 A1 | 5/2005 | Fujii et al. |
| 2005/0119737 A1 | 6/2005 | Bene et al. |
| 2005/0159657 A1 | 7/2005 | Cappo et al. |
| 2006/0055956 A1 | 3/2006 | Takahashi et al. |
| 2006/0103724 A1 | 5/2006 | Jongsma et al. |
| 2006/0109423 A1 | 5/2006 | Wang |
| 2006/0140454 A1 | 6/2006 | Northcott et al. |
| 2006/0159722 A1 | 7/2006 | Braithwaite et al. |
| 2006/0234071 A1 | 10/2006 | Friz et al. |
| 2006/0270802 A1 | 11/2006 | Washizu et al. |
| 2008/0002202 A1 | 1/2008 | Hall et al. |
| 2008/0081996 A1 | 4/2008 | Grenon et al. |
| 2008/0081999 A1 | 4/2008 | Gravely et al. |
| 2008/0161741 A1 | 7/2008 | Bene et al. |
| 2008/0273171 A1 | 11/2008 | Huth et al. |
| 2008/0285043 A1 | 11/2008 | Fercher et al. |
| 2008/0287808 A1 | 11/2008 | Tearney et al. |
| 2008/0309855 A1 | 12/2008 | Yan et al. |
| 2008/0316499 A1 | 12/2008 | Korb et al. |
| 2008/0319323 A1 | 12/2008 | Gravely et al. |
| 2009/0161090 A1 | 6/2009 | Campbell et al. |
| 2009/0201465 A1 | 8/2009 | Huth |
| 2009/0225276 A1 | 9/2009 | Suzuki |
| 2009/0275929 A1 | 11/2009 | Zickler |
| 2010/0026323 A1 | 2/2010 | Tiefenthaler |
| 2010/0085540 A1 | 4/2010 | Korb et al. |
| 2010/0102211 A1 | 4/2010 | Murooka et al. |
| 2010/0253907 A1 | 10/2010 | Korb et al. |
| 2010/0259721 A1 | 10/2010 | Korb et al. |
| 2010/0259723 A1 | 10/2010 | Korb et al. |
| 2010/0297193 A1 | 11/2010 | Archambeau et al. |
| 2010/0315591 A1 | 12/2010 | Grafton et al. |
| 2011/0007321 A1 | 1/2011 | Everett et al. |
| 2011/0043661 A1 | 2/2011 | Podoleanu |
| 2011/0053283 A1 | 3/2011 | Hood et al. |
| 2011/0096292 A1 | 4/2011 | Saito |
| 2011/0181836 A1 | 7/2011 | Rowe |
| 2011/0206291 A1 | 8/2011 | Kashani et al. |
| 2011/0237999 A1 | 9/2011 | Muller et al. |
| 2011/0273550 A1 | 11/2011 | Amano et al. |
| 2011/0292395 A1 | 12/2011 | Fercher et al. |
| 2012/0188508 A1 | 7/2012 | Kim et al. |
| 2012/0226156 A1 | 9/2012 | Grenon et al. |

(56) References Cited

U.S. PATENT DOCUMENTS

| | | |
|---|---|---|
| 2013/0010257 A1 | 1/2013 | Primeau et al. |
| 2013/0050647 A1 | 2/2013 | Steinmueller |
| 2013/0058550 A1 | 3/2013 | Tanimoto et al. |
| 2013/0141698 A1 | 6/2013 | Huth et al. |
| 2013/0169933 A1 | 7/2013 | Wang |
| 2013/0208495 A1 | 8/2013 | Dau et al. |
| 2013/0293842 A1 | 11/2013 | Grenon et al. |
| 2013/0308095 A1 | 11/2013 | Korb et al. |
| 2014/0016093 A1 | 1/2014 | Korb et al. |
| 2014/0028979 A1 | 1/2014 | De Juan, Jr. et al. |
| 2014/0104574 A1 | 4/2014 | Grenon et al. |
| 2014/0118699 A1 | 5/2014 | Huth et al. |
| 2014/0240671 A1 | 8/2014 | Korb et al. |
| 2014/0285767 A1 | 9/2014 | Korb et al. |
| 2014/0330129 A1 | 11/2014 | Grenon et al. |
| 2014/0363064 A1 | 12/2014 | Lee et al. |
| 2015/0138504 A1 | 5/2015 | Korb et al. |
| 2015/0141837 A1 | 5/2015 | Arita et al. |
| 2015/0351626 A1 | 12/2015 | Huth et al. |
| 2015/0351627 A1 | 12/2015 | Huth et al. |
| 2015/0351628 A1 | 12/2015 | Huth et al. |
| 2017/0280991 A1 | 10/2017 | Huth et al. |
| 2017/0280992 A1 | 10/2017 | Huth et al. |
| 2018/0001108 A1 | 1/2018 | Kelleher |
| 2018/0042472 A1 | 2/2018 | Grenon et al. |
| 2018/0177391 A1 | 6/2018 | Korb et al. |
| 2018/0279871 A1 | 10/2018 | Grenon et al. |
| 2019/0150728 A1 | 5/2019 | Grenon et al. |

FOREIGN PATENT DOCUMENTS

| | | |
|---|---|---|
| CN | 103799976 A | 5/2014 |
| DE | 3108878 A1 | 9/1982 |
| EP | 0943288 A1 | 9/1999 |
| EP | 1900320 A1 | 3/2008 |
| EP | 2189108 A1 | 5/2010 |
| EP | 2695570 A1 | 2/2014 |
| EP | 1900320 B1 | 4/2014 |
| EP | 3015107 A1 | 5/2016 |
| GB | 2407378 B | 9/2006 |
| JP | 6269412 A | 9/1994 |
| JP | 7002647 A | 1/1995 |
| JP | 7136120 A | 5/1995 |
| JP | H107136120 A | 5/1995 |
| JP | 07313464 A | 12/1995 |
| JP | 07313465 A | 12/1995 |
| JP | 8052112 A | 2/1996 |
| JP | 8098811 A | 4/1996 |
| JP | H109201334 A | 8/1997 |
| JP | 2000262468 A | 9/2000 |
| JP | 2001309889 A | 11/2001 |
| JP | 2004236727 A | 8/2004 |
| JP | 2005211173 A | 8/2005 |
| JP | 2005211633 A | 8/2005 |
| JP | 2005230328 A | 9/2005 |
| JP | 2007068928 A | 3/2007 |
| JP | 2007209370 A | 8/2007 |
| JP | 2007523382 A | 8/2007 |
| JP | 2008246004 A | 10/2008 |
| JP | 2009134276 A | 6/2009 |
| JP | 3168993 U | 7/2011 |
| JP | 5748268 B2 | 7/2015 |
| JP | 2016179098 A | 10/2016 |
| JP | 2017012663 A | 1/2017 |
| KR | 20010058557 B1 | 7/2001 |
| KR | 101259056 B1 | 4/2013 |
| KR | 20160146220 A | 12/2016 |
| KR | 101755630 B1 | 7/2017 |
| WO | 0026614 A1 | 5/2000 |
| WO | 2005044099 A1 | 5/2005 |
| WO | 2007004348 A1 | 1/2007 |
| WO | 2008089327 A1 | 7/2008 |
| WO | 2008137863 A2 | 11/2008 |
| WO | 2008156883 A | 12/2008 |
| WO | 2008156884 A1 | 12/2008 |
| WO | 2012137545 A1 | 10/2012 |
| WO | 2013082356 A2 | 6/2013 |
| WO | 2013082356 A3 | 6/2013 |
| WO | 2013166352 A2 | 11/2013 |
| WO | 2013166477 A2 | 11/2013 |
| WO | 2014018640 A1 | 1/2014 |
| WO | 2015187315 A1 | 12/2015 |
| WO | 2015187317 A1 | 12/2015 |
| WO | 2016063130 A1 | 4/2016 |
| WO | 2018004234 A1 | 1/2018 |

OTHER PUBLICATIONS

Korb, Donald R. et al., "Tear Film Lipid Layer Thickness as a Function of Blinking," Cornea, vol. 13, No. 4, 1994, pp. 354-359.

Korb, Donald R. O.D., et al., "Comparison of Fluorescein Break-Up Time Measurement Reproducibility Using Standard Fluorescein Strips Versus the Dry Eye Test (DET) Method," Cornea, vol. 20(8), Philadelphia, 2001, 8 pages.

Korb, Donald R., "Alleviation of Computer-Induced Eye Discomfort Syndrome and Associated Lipid Layer Changes," Lacrimal Gland, Tear Film, and Dry Eye Syndrome 3, 2002, pp. 501-506.

Korb, Donald R., "The Tear Film—Its Role Today and in the Future," 2002, 52 pages.

Korb, Donald R., et al., "Human and Rabbit Lipid Layer and Interference Pattern Observations," Lacrimal Gland, Tear Film, and Dry Eye Syndromes 2, Plenum Press, New York, 1998, pp. 305-308.

Korb, Donald R., et al., "Tear Film Lipid Layer Formation: Implications for Contact Lens Wear," Review, Optometry and Vision Science, vol. 73, No. 3, 1996, pp. 189-192.

Korb, Donald R., et al., "The Effects of Anionic and Zwitterionic Phospholipids on the Tear Film Lipid Layer," Lacrimal Gland, Tear Film, and Dry Eye Syndromes 3, Kluwer Academic/Plenum Publishers, 2002, pp. 495-499.

Korb, Donald R., et al., "The Tear Film Structure, Function and Clinical Examination," British Contact Lens Association, Butterworth Heinemann, Circa 1999, pp. 154-179.

Korb, Donald R., O.D. et al., "The Phenomenon of Central Circular Clouding; the loss of corneal transparency unique to contact lens practice requiring specialized techniques for early recognition," Journal of American Optometric Association, vol. 39, No. 3, Mar. 1968, pp. 223-230.

Korb, Donald R., O.D., et al., "Lid Wiper Epitheliopathy and Dry Eye Syndrome," Eye & Contact Lens, vol. 31, No. 1, 2005, pp. 2-8.

Korb, Donald R., O.D., et al., "Meibomian Gland Dysfunction and Contact Lens Intolerance" Jnl American Optometric Association, vol. 51, No. 3, Mar. 1980, 9 pages (pp. 243-251).

Korb, Donald R., OD, et al., "A Device to Standardize and Quantify the Force Used to Diagnose Meibomian Gland Obstruction and Dysfunction" 2007, 1 page.

Korb, Donald R., OD, et al., "A New Device for the Diagnosis of Meibomian Gland Dysfunction and Obstruction" 2007, 1 page.

Korb, Donald, "Survey of Preferred tests for Diagnosis of the Tear Film and Dry Eye," Cornea, vol. 19, 2000, pp. 483-486.

Kowalik, W. et al., "Corneal Topography Measurement of the Eye by Means of Radial Shearing Interferometer," Proc. SPIE—Int. Soc. Opt. Eng. vol. 4356, 2001. pp. 375-380.

Kronemyer, Bob, "Dry Eye Experts Unveil New Treatment Guidelines, Terminology" Ocular Surgery News, U.S. Edition, May 2007, 1 page.

Liebovitch, Larry S., Ph.D., "The Shape of the Eye: Why the Eye is Round" Florida Atlantic University, Boca Raton, FL, Circa 1986, 28 pages (pp. 1-27).

Licznerski, T.J. et al., "Application of Twyman-Green Interferometer for Evaluation of In Vivio Breakup Characteristic of the Human Tear Film," Journal of Biomedical Optics, vol. 4, No. 1, Jan. 1999, pp. 176-182.

Licznerski, T.J. et al., "Interference and Model Study of the Human Tear Film," Politechnika Wroclawska, Source DAI-C 60/04, Winter 1999, p. 782 (Abstract only).

Lilcznerski, T.J. et al., "Novel Double Path Shearing Interferometer in Corneal Topography Measurements," Proceedings of the SPIE, vol. 5959, 2005, 6 pages.

(56) References Cited

OTHER PUBLICATIONS

Licznerski, Tomasz J., et al., "Analysis of Shearing Interferograms of Tear Film Using Fast Fourier Transforms" Journal of Biomedical Optics, vol. 3, No. 1, Jan. 1998, pp. 32-37.
Lopez Garcia, J.S. et al., "Measure of the Fatty Layer Thickness of Precorneal Tear Film by Interference Colours in Different Types of Dry Eye," Sociedad Espanola de Oftalmologia, vol. 78, Part 5, Jan. 2003, pp. 257-264.
Lorentz, Holly Irene, "Lipid Deposition on Hydrogel Contact Lenses" Master's Thesis, University of Waterloo, Ontario, Canada, 2006, 175 pages.
Loveridge, Ron, "Effective Management of Induced Dry Eye Syndrome with Soft CLs" www.optometry.co.uk, Apr. 2000,pp. 35-38.
Lui, Haixia, MD, et al., "Temporal Progression and Spatial Repeatability of Tear Breakup" Optometry and Vision Science, vol. 83, No. 10, Oct. 2006, pp. 723-730.
Mathers, W.D., "Assessment of the Tear Film with Tandem Scanning Confocal Microscopy," Cornea, vol. 16, No. 2, 1997, pp. 162-168.
Mathers, W.D., "Ocular Evaporation in Meibomian Gland Dysfunction and Dry Eye," Ophthalmology, vol. 100, No. 3, Mar. 1993, pp. 347-351.
Matsumoto, Yukihiro, et al., "Efficacy of a New Warm Moist Air Device on Tear Functions of Patients with Simple Meibomian Gland Dysfunction" Cornea, vol. 25, No. 6, Jul. 2006, 1 page.
McCarty, C.A. et al., "The Epidemiology of Dry Eye in Melbourne, Australia," Ophthalmology, vol. 105, No. 6, Jun. 1998, pp. 1114-1119.
McDonald, James E., "Surface Phenomena of the Tear Films," Tr. Am. Opth. Soc., vol. 66, 1968, pp. 905-939.
McGrath, Dermot, "Iris diaphragm IOLs safe and effective in treating aniridia," EuroTimes, European Society of Cataract & Refractive Surgeons, May 2007, http://www.escrs.org/PUBLICATIONS/EUROTIMES/07MAY/IRISDIAPHRAGMIOLS.PDF, p. 42.
Miano, Fausto, et al., "Interface Properties of Simplified Tear-Like Fluids in Relation to Lipid and Aqueous Layers Composition" Lacrimal Gland, Tear Film, and Dry Eye Syndromes 3, Kluwer Academic/Plenum Publishers, 2002, 13 pages (pp. 405-417).
Millar, et al., "Analysis of comparison of human meibomian lipid films and mixtures with cholestryl esters in vitro films using high resolution color microscopy," Cornea, vol. 53, No. 8, Jul. 2012, pp. 4710-4719.
Miller, David "Pressure of the Lid on the Eye" Arch. Opthalmology, vol. 78, 1967, 7 pages (pp. 382-330).
Mitra, M. et al., "Tear Film Lipid Layer Thickness and Ocular Comfort after Meibomian Therapy via Latent Heat with a Novel Device in Normal Subjects" Eye, vol. 19, 2005, 4 pages (pp. 657-660).
Mori, Asako, M.D., et al., "Efficacy and Safety of Infrared Warming of the Eyelids" Cornea, vol. 18(2), 1999, 6 pages (pp. 188-193).
Nichols, Jason J., et al., "The Impact of Hydrogel Lens Settling on the Thickness of the Tears and Contact Lens" Investigative Ophthalmology & Visual Science, vol. 45, No. 8, Aug. 2004, pp. 2549-2554.
Nichols, Jason J., et al., "The Thickness of the Post-Lens Tear Film Measured by Interferometry" Lacrimal Gland, Tear Film, and Dry Eye Syndromes 3, Kluwer Academic/Plenum Publishers, 2002, pp. 929-933.
Nichols, Jason J., et al., "Thickness of the Pre- and Post-Contact Lens Tear Film Measured In Vivo by Interferometry" Investigative Ophthalmology & Visual Science, vol. 44, No. 1, Jan. 2003, pp. 68-77.
Nichols, Jason J., OD, MS, FAAO, et al., "Evaluation of Tear Film Interference Patterns and Measures of Tear Break-Up Time" Optometry and Vision Science, vol. 79, No. 6, Jun. 2002, pp. 363-369.
Nichols, Jason J., OD, MS, MPH, et al., "The Effect of Eye Closure on the Post-Lens Tear Film Thickness During Silicone Hydrogel Contact Lens Wear" Cornea, vol. 22, No. 6, 2003, pp. 539-544.

Nichols, K.K. et al., "The Lack of Association Between Signs and Symptoms in Patients with Dry Eye Disease," Cornea, vol. 23, No. 8, Nov. 2004, pp. 762-770.
Nichols, K.K. et al., "The Repeatability of Clinical Measurements of Dry Eye," Cornea, vol. 23, No. 3, Apr. 2004, pp. 272-285.
Norn, M.S., "Semiquantitative Interference Study of Fatty Layer of Precorneal Film," ACTA Ophthalmologica, vol. 57, 1979, pp. 766-774.
Corrected Notice of Acceptance for Australian patent application 2011235961 dated Sep. 19, 2013, 2 pages.
Notice of Acceptance for Australian patent application 2011235961 dated Sep. 11, 2013, 2 pages.
Ohashi, Yoshiki, et al., "Laboratory Findings in Tear Fluid Analysis," Clinica Chimica Acta 369, 2006, 12 pages (pp. 17-28).
Olson, Mary Catherine, B.A., et al., "Increase in Tear Film Lipid Layer Thickness Following Treatment with Warm Compresses in Patients with Meibomian Gland Dysfunction" Eye & Contact Lens, vol. 29(2), 2003, 6 pages.
Ong, B. L., et al., "Meibomian Gland Dysfunction: Some Clinical, Biochemical and Physical Observations" Ophthal. Physiol. Opt., vol. 10, Apr. 1990, 5 pages (pp. 144-148).
Patel, S. et al., "Corneal Sensitivity and Some Properties of the Tear Film After Laser In Situ Keratomileusis," Journal of Refractive Surgery, vol. 17, No. 1, 2001, pp. 17-24.
Patel, Sudi, PhD, FCOptom, FAAO, et al., "Tear Meniscus Height, Lower Punctum Lacrimale, and Tear Lipid Layer in Normal Aging" Optometry and Vision Science, vol. 83, No. 10, Oct. 2006, 9 pages (pp. 732-739).
Paugh, J.R. et al., "White Light Tear Film Interferometry in Dry Eye Sub-Types," IOVS, vol. 45, Supp. 1, Apr. 2004, E-Abstract 93, 2 pages.
Pflugfelder, S.C. et al., "Evaluation of Subjective Assessments and Objective Diagnostic Tests for Diagnosing Tear-Film Disorders Known to Cause Ocular Irritation," Cornea, vol. 17, No. 1, 1998, pp. 38-56.
Pimenidi, M.K., et al., "Meibomian Gland Disfunction in Computer Vision Syndrome (abstract)," Annals of Ophthalmology (Vestn Oftalmol.) (Russia), Nov.-Dec. 2010, 126(6), http://www.medlit.ru/medeng/vof/vof10e0649.htm, 3 pages.
Primeau et al., "Interferometer for measuring the dynamic surface topography of a human tear film," Design and Quality for Biomedical Technologies V, vol. 8215, Feb. 2012, 11 pages.
Prydal, J.I. et al., "In Vivo Confocal Microscopy of the Cornea and Tear Film," Scanning, vol. 17, 1995, pp. 133-135.
Prydal, J.I. et al., "Study of Precorneal Tear Film Thickness and Structure by Interferometry and Confocal Microscopy," Investigative Ophthalmology and Visual Science, vol. 33, No. 6, May 1992, pp. 1996-2005.
Prydal, Jeremy I. et al., "Study of Human Precorneal Tear Film Thickness and Structure Using Laser Interferometry," Investigative Ophthalmology & Visual Science, vol. 33, No. 6, May 1992, pp. 2006-2011.
Remeseiro et al., "Automatic classification of the interferential tear film lipid layer using colour texture analysis," Computer Methods and Programs in Biomedicine, vol. 111, No. 1, Elsevier Ireland Ltd., Jul. 2013, pp. 93-103.
Rolando, M. et al., "The Dynamic Lipid Interference Pattern (DLIP) Test in Normal and Dry Eyes," IOVS, vol. 46, Supp. S, 2005, E-Abstract 4422, 2 pages.
Rolando, Maurizio et al., "New Test to Quantify Lipid Layer Behavior in Healthy Subjects and Patients with Keratoconjunctivitis Sicca," Cornea, vol. 27, No. 8, Sep. 2008, pp. 866-870.
Scaffidi, R.C. et al., "Lipid Layer Thickness and Dry Eye Symptoms," IOVS, vol. 46, Supp. S, 2005, E-Abstract 4444, 2 pages.
Schaumberg, D.A. et al., "Development and Validation of a Short Global Dry Eye Symptom Index," The Ocular Surface, vol. 5, No. 1, Jan. 2007, pp. 50-57.
Shiel, William C., Jr., MD, FACP, FACR, "Sjogren's Syndrome" MedicineNet.com, http:www.medicinenet.com, Sep. 2006, 3 pages.
Sullivan, David A., et al., "Androgen Influence on the Meibomian Gland" Investigative Ophthalmology & Visual Science, vol. 41, No. 12, Nov. 2000, 11 pages (pp. 3732-3742).

(56) References Cited

OTHER PUBLICATIONS

Sullivan, David A., et al., "Androgen Regulation of the Meibomian Gland" Lacrimal Gland, Tear Film, and Dry Eye Syndromes 2, Plenum Press, New York, 1998, 5 pages (pp. 327-331).

Szczesna-Iskander, D. et al., "Future Directions in Non-Invasive Measurements of Tear Film Surface Kinetics," Optometry and Vision Science, vol. 89, No. 5, May 2012 pp. 749-759.

Szczesna, D. et al., "Numerical Analysis of Interferograms of Tear Film Build-Up Time," Ophthalmic and Physiological Optics, vol. 29, No. 3, May 2009, pp. 211-218.

Szczesna, D., et al., "Predicting dry eye using noninvasive techniques of tear film surface assessment," Investigative Ophthalmology and Visual Science, vol. 52, No. 2, Feb. 2011, http://www.iovs.org/content/52/2/751.full.pdf+html, pp. 751-756.

Szczesna, D.H. et al., "Interferometric Measurements of the Tear Film Irregularities on the Human Cornea," Proceedings of the SPIE, vol. 5959, 2005, 10 pages.

Szczesna, Dorota H., et al., "Assessing Tear Film on Soft Contact Lenses With Lateral Shearing Interferometry," Eye & Contact Lens: Science & Clinical Practices, vol. 37, Issue 6, Nov. 2011, pp. 342-347.

Szczesna, Dorota H., et al., "Lateral Shearing Interferometry for Analysis of Tear Film Surface Kinetics," Optom. Vis. Sci., vol. 87, No. 7, Jul. 2010, pp. 513-517.

Szczesna, Dorota H., et al., "Robust estimation of tear film surface quality in lateral shearing interferometry," Journal of Biomedical Optics, vol. 14, No. 6, Nov./Dec. 2009, 4 pages.

Thai, Lee Choon, BSc, MCOptom, et al., "Contact Lens Drying and Visual Performance: The Vision Cycle with Contact Lenses" Optometry and Vision Science, vol. 79, No. 6, Jun. 2002, 8 pages (pp. 381-388).

Thai, Lee Choon, BSc, MCOptom, et al., "Effect of Contact Lens Materials on Tear Physiology" Optometry and Vision Science, vol. 81, No. 3, Mar. 2004, 11 pages (pp. 194-204).

Tomlinson, Alan, et al., "Reliability of Measurements of Tear Physiology" Lacrimal Gland, Tear Film, and Dry Eye Syndromes 3, Kluwer Academic/Plenum Publishers, 2002, 9 pages (pp. 1097-1105).

Tomlinson, Alan, et al., "Tear Film Osmolarity: Determination of a Referent for Dry Eye Diagnosis" Investigative Ophthalmology & Visual Science, vol. 47, No. 10, Oct. 2006, 7 pages (pp. 4309-4315).

Tseng, S.C. et al., "Changes of Lipid Tear Film in Dry Eye Patients and Normal Subjects Following One Drop of a New Emulsion Eye Drop Using Kinetic Analysis of Tear Interference Images," ARVO, vol. 44, 2003, E-Abstract 2457, 2 pages.

Uchida, A. et al., "Nonivasive Interference Tear Meniscometry in Dry Eye Patients with Sjogren Syndrome," Am. J. Ophthalmol., vol. 144, No. 2, Aug. 2007, pp. 232-237.

Van Veen, R. L. P., et al., "Determination of VIS-NIR Absorption Coefficients of Mammalian Fat, with Time- and Spatially Resolved Diffuse Reflectance and Transmission Spectroscopy" Circa 2004, 3 pages.

Veres, A., et al., "Imaging lid-parallel conjunctival folds with OCT and comparing its grading with the slit lamp classification in dry eye patients and normal subjets," Investigative Ophthalmology and Visual Science, vol. 52, No. 6, May 2011, http://www.iovs.org/content/52/6/2945.full.pdf+html, pp. 2945-2951.

Wang, Jianhua et al., "Relationships between Central Tear Film Thickness and Tear Menisci of the Upper and Lower Eyelids" Investigative Ophthalmology & Visual Science, vol. 47, No. 10, Oct. 2006, 7 pages (pp. 4349-4355).

Wu, Dijia et al., "Sign Ambiguity Resolution for Phase Demodulation in Interferometry with Application to Prelens Tear Film Analysis," 2010 IEEE Computer Society Conference on Computer Visions and Pattern Recognition, CVPR 2010, 2010, pp. 2807-2814.

Wu, Dijia et al., "Texture Based Prelens Tear Film Segmentation in Interferometry Images," Machine Vision and Applications, vol. 21, No. 3, Apr. 2010, pp. 253-259.

Yokoi, N, et al., "Development of Automated Rheological Analysis for Tear Film Lipid Layer Spread Using the Cross-Correlation Method" Association for Research in Vision and Ophthalmology, 2007, 1 page.

Yokoi et al., "A Newly Developed Video-Meibography System Featuring a Newly Designed Probe," Japan Journal of Ophthalmology, vol. 51, Jan. 2007, pp. 53-56.

Yokoi, N. et al., "Assessment of Meibomian Gland Function in Dry Eye Using Meibometry," Arch. Ophthalmol., No. 117, Jun. 1999, pp. 723-729.

Yokoi, N. et al., "Correlation of Tear Lipid Layer Interference Patterns with the Diagnosis and Severity of Dry Eye," Amercian Journal of Ophthalmology, vol. 122, Dec. 1996, pp. 818-824.

Yokoi, N. et al., "New Instruments for Dry Eye Diagnosis," Seminars in Opthalmology, vol. 20, 2004, pp. 63-70.

Yokoi, Norihiko, et al., "Non-Invasive Methods of Assessing the Tear Film" Experimental Eye Research, vol. 78, Elsevier Ltd., 2003, 9 pages (pp. 399-407).

Young, G. et al., "Characteristics of the Pre-Lens Tear Films During Hydrogel Contact Lens Wear," Ophthal. Physiol. Opt., vol. 11, Jan. 1991, pp. 53-58.

Oculus, "Oculus Keratograph 5M Der Revolutionär," Date Unknown, Oculus, 2 pages.

Bon, "Meibographie: mit der Phoenix Analyse-Software," bon Optic Vertriebsgesellschaft mbH, Nov. 2011, 6 pages.

Yokoi, N. et al., "Relationship between tear volume and tear meniscus curvature," Arch. Ophthalmology, vol. 122, Sep. 2004 ,pp. 1265-1269.

Notice of Allowance for U.S. Appl. No. 11/820,664 dated May 27, 2010, 10 pages.

Notice of Allowance for U.S. Appl. No. 11/820,664 dated Mar. 25, 2010, 10 pages.

Final Office Action for U.S. Appl. No. 11/820,664 dated Dec. 29, 2009, 7 pages.

Non-final Office Action for U.S. Appl. No. 11/820,664 dated Jun. 5, 2009, 9 pages.

Notice of Allowance for U.S. Appl. No. 12/633,057 dated Jun. 9, 2011, 8 pages.

Fogt, Nick, et al., "Interferometric Measurement of Tear Film Thickness by use of Spectral Oscillations" J. Opt. Soc. Am. A., vol. 15, No. 1, Jan. 1998, 8 pages (pp. 268-275).

Foulks, G.N. et al., "Meibomian Gland Dysfunction: a Clinical Scheme for Description, Diagnosis, Classification, and Grading," The Ocular Surface, vol. 1, No. 3, Jul. 2003, pp. 107-126.

Foulks, G.N., "The Correlation Between the Tear Film Lipid Layer and Dry Eye Disease," Survey of Ophthalmology, vol. 52, No. 4, Jul.-Aug. 2007, pp. 369-374.

Foulks, G., "Ocular Surface Cell Biology—from the Light to the Dark Side," Ocular Surface, vol. 10, No. 4, Oct. 2012, 1 page.

Garcia, Julius, "Research Report; Tear Film Measurement" Report No. 09354231-1; Aug. 2006, 46 pages.

Garcia-Resua, C., et al., "Clinical Evaluation of the Tears Lipid Layer in a Young University Population" Rev. Esp. Contact, vol. 12, 2005, 6 pages.

Garncarz, B.E. et al., "Corneal Topography Measurement by Means of Radial Shearing Interference II—Experiment Results," Optik, vol. 113, No. 1, 2002, pp. 46-50.

Goto, E. et al., "Differentiation of Lipid Tear Deficiency Dry Eye by Kinetic Analysis of Tear Interference Images," Archives of Ophthalmology, vol. 121, No. 2 Feb. 2003, pp. 173-180.

Goto, E. et al., "Successful Tear Lipid Layer Treatment for Refractory Dry Eye in Office Workers by Low-Dose Lipid Application on the Full-Length Eyelid Margin," American Journal of Ophthalmology, vol. 142, No. 2, Aug. 2006, pp. 264-270.

Goto, E. et al., "Tear Evaporation Dynamics in Normal Subjects and Subjects with Obstructive Meibomian Gland Dysfunction," Investigative Ophthalmology abnd Visual Science, vol. 44, 2003, pp. 533-539.

Goto, E., et al. "Treatment of Non-Inflamed Obstructive Meibomian Gland Dysfunction by an Infrared Warm Compression Device" British Journal of Ophthalmology, BJO Online, http://www.bmjjournals.com/cgi/reprintform, vol. 26, 2002, 5 pages (pp. 1402-1407).

(56) References Cited

OTHER PUBLICATIONS

Goto, Eiki, et al. "Computer-Synthesis of an Interference Color Chart of Human Tear Lipid Layer, by a Colorimetric Approach" Investigative Ophthalmology & Visual Science, vol. 44, No. 11, Nov. 2003, 5 pages (pp. 4693-4697).

Goto, Eiki, et al., "Kinetic Analysis of Tear Interference Images in Aqueous Tear Deficiency Dry Eye Before and After Punctual Occlusion" Investigative Ophthalmology & Visual Science, vol. 44, No. 5, May 2003, 9 pages (pp. 1897-1905).

Goto, Eiki, M.D., "Quantification of Tear Interference Image; Tear Fluid Surface Nanotechnology" Cornea, vol. 23, Suppl. 1, Nov. 2004, 5 pages (pp. S20-S24).

Gravely, Ben, "Observations from TFA3" Aug. 2006, 3 pages.

Greiner, Jack V., et al., "Effect of Meibomian Gland Occlusion on Tear Film Lipid Layer Thickness" Lacrimal Gland, Tear Film, and Dry Eye Syndromes 2, Plenum Press, New York, 1998, 4 pages (pp. 345-348).

Greiner, Jack V., et al., "Meibomian Gland Phospholipids" Current Eye Research, Oxford University Press, 1995, 5 pages (pp. 371-375).

Greiner, Jack V., et al., "Volume of the Human and Rabbit Meibomian Gland System" Lacrimal Gland, Tear Film, and Dry Eye Syndromes 2, Plenum Pres, New York, 1998, 5 pages (pp. 339-343).

Guillon, J.P. et al., "Preocular Tear Film Characteristics of Nonwearers and Soft Contact Lens Wearers," Optometry and Vision Science, vol. 74, No. 5, 1997, pp. 273-279.

Guillon, J.P., "Tear Film Photography and Contact Lens Wear," Journal of the British Contact Lens Association, 1982, pp. 84-87.

Guillon, J.P., "The Tear Film Structure of the Contact Lens Wearer," Dept. of Optometry and Visual Science, City University, London, 1987, 398 pages.

Guillon, Jean-Pierre, "Non-Invasive Tearscope Plus Routine for Contact Lens Fitting," Contact Lens and Anterior Eye, (Supplement) 21, 1998, pp. S31-S40.

Guillon, Jean-Pierre, "Use of the Tearscope Plus and Attachments in the Routine Examination of the Marginal Dry Eye Contact Lens Patient," Lacrimal Gland, Tear Film, and Dry Eye Syndrome 2, 1998, pp. 859-867.

Hamilton, Dr. Roy C., "Ocular Explosion; a Dreaded Complication of Ophthalmic Regional Anaesthesia" Ophthalmic Anaesthesia News, Issue 4, Apr. 2001, 43 pages.

Hayreh, Sohan Singh, et al., "Parapapillary Chorioretinal Atrophy in Chronic High-Pressure Experimental Glaucoma in Rhesus Monkeys" Investigative Ophthalmology & Visual Science, vol. 39, No. 12, Nov. 1998, 8 pages (pp. 2296-1303).

Hellmuth, T. et al., "Non-Contact Measurement of the Optical Imaging Quality of an Eye," Proc. SPIE—Int. Soc. Opt. Eng. vol. 4431, 2001, pp. 52-58.

Hickson, Ian, "The Eye" Ian Hickson's Description of the Eye, http://academia.hixie.ch/bath/eye/home.html, 1998, 11 pages.

Author Unknown, Honan Balloon Intraocular Pressure Reducer with Valve—Complete, Ambler Surgical, Ambler Product No. HBC-120, Nov. 19, 2007, http://www.amblersurgical.com/store/product.cfm/pID:2456_5961E, 1 page.

Hosaka, Eri et al., "Interferometry in the Evaluation of Precorneal Tear Film Thickness in Dry Eye," American Journal of Opthalmology, vol. 151, No. 1, Jan. 2011, pp. 18-23.

International Search Report and Written Opinion for PCT/US2013/038116 dated Sep. 12, 2013, 13 pages.

International Search Report and Written Opinion for PCT/US2013/038149 dated Sep. 12, 2013, 18 pages.

International Search Report and Written Opinion for PCT/US2013/039395 dated Oct. 11, 2013, 11 pages.

Shida, Reiko et al., "Tear Film with 'Orgahexa Eyemasks' in Patients with Meibomian Gland Dysfunction," Optometry and Visions Science, vol. 85, No. 8, Aug. 2008, pp. E684-E691.

Iskander, D. Robert, PhD., et al., "Applications of High-Speed Videokeratoscopy" Clinical and Experimental Optometry, vol. 88, vol. 4, Jul. 2005, 9 pages (pp. 223-231).

Isreb, M.A. et al., "Correlation of Lipid Layer Thickness Measurements with Fluorescein Tear Film Breakup Time and Schirmer's Test," Eye, vol. 17, 2003, pp. 79-83.

Kaisheva, M et al., "Thin Liquid Films from Water-Based Dispersions of Cellulose Acethophthalate in the Presence of Pilocarpine Hydrochloride," J. Dispersion Sci. Technol., 1997, 14 pages.

Khamene, Ali, et al., "A Spectral-Discrimination Method for Tear-Film Lipid-Layer Thickness Estimation from Fringe Pattern Images" IEEE Transactions on Biomedical Engineering, vol. 47, No. 2, Jan. 2000, 10 pages (pp. 249-258).

Kilp, H. et al., "Tear Film Observation by Reflecting Microscopy and Differential Interference Contrast Microscopy," The Dry Eye Institute, Inc., 1986, pp. 564-569.

Kimball, S., et al., "Evidence for the major contribution of evaporation to tear film thinning between blinks," Investigative Ophthalmology and Visual Science, vol. 51, No. 12, Dec. 2010, http://www.iovs.org/content/51/12/6294.full.pdf+html, pp. 6294-6297.

King-Smith, P. Ewen et al., "The Thickness of the Human Precorneal Tear Film: Evidence from Reflection Spectra," Investigative Ophthalmology & Visual Science, Oct. 2000, vol. 41, No. 11, pp. 3348-3359.

King-Smith, P. Ewen, et al., "Application of a novel interferometric method to investigate the relation between lipid layer thickness and tear film thinning," Investigative Ophthalmology and Visual Science, vol. 51, No. 5, May 2010, http://www.iovs.org/content/51/5/2418.full.pdf+html, pp. 2418-2423.

King-Smith, P. Ewen, et al., "Evaporation from the Human Tear Film Studied by Interferometry" Lacrimal Gland, Tear Film, and Dry Eye Syndromes 3, Kluwer Academic/Plenum Publishers, 2002, 5 pages (pp. 425-429).

King-Smith, P. Ewen, et al., "Interferometric Imaging of the Full Thickness of the Precorneal Tear Film" J. Opt. Soc. Am. A, vol. 23, No. 9, Sep. 2006, 8 pages (pp. 2097-2104).

King-Smith, P. Ewen, et al., "Three Interferometric Methods for Measuring the Thickness of Layers of the Tear Film" Optometry and Vision Science, vol. 76, No. 1, Jan. 1999, 14 pages (pp. 19-32).

King-Smith, P.E. et al., "Can the Mucus Layer of the Tear Film be Demonstrated by Interferometry?," IOVS, vol. 45, Supp. 2, Apr. 2004, E-Abstract 3882. 2 pages.

King-Smith, P.E. et al., "Human Tear Film Breakup Studied by a New Imaging Interferometer: Preliminary Observations," IOVS, vol. 46, Supp. S, 2005, E-Abstract 4400, 2 pages.

Kojima, Takashi et al.., "A New Noninvasive Tear Stability Analysis System for the Assessment of Dry Eyes," Investigative Ophthalmology & Visual Science, May 2004, vol. 45, No. 5, pp. 1369-1374.

Korb, D. et al., "Lipid Layer Thickness Changes Following the Instillation of Two Novel Lubricant Eye Drops," IOVS, vol. 46, Supp. S, 2005, E-Abstract 2036, 2 pages.

Korb, Donald R. et al., "Meibomian Gland Diagnostic Expressibility: Correlation With Dry Eye Symptoms and Gland Location," Cornea, vol. 27, No. 10, Dec. 2008, pp. 1142-1147.

Korb, Donald R. et al., "Effect of Periocular Humidity on the Tear Film Lipid Layer," Cornea, vol. 15, No. 2, 1996, pp. 129-134.

Non-Final Office Action for U.S. Appl. No. 15/995,612, dated Jul. 10, 2018, 6 pages.

Final Office Action for U.S. Appl. No. 14/269,646, dated Jul. 11, 2018, 36 pages.

Author Unknown, "Tomey's RT-7000 is new and improved," Instruments—New Product Gallery, Vision Care Product News (VCPN), Jul. 2008, 1 page.

Author Unknown, "Tearscope Plus: Introduction and guided tour to the benefits of the Keeler Tearscope-plus," Keeler Instruments, bon Optic, created Jan. 24, 2006, www.bon.de/download/TearscopeE.pdf, 22 pages.

Australian Patent Examination Report No. 1 for Australian patent application 2011235961, dated Jan. 2, 2013, 3 pages.

Alonso-Caneiro, D. et al., "Context-Based Modelling of Interferometric Signals for the Assessment of Tear-Film Surface Quality," 2009 IEEE/SP 15th Workshop on Statistical Signal Processing (SSP), 2009, pp. 553-556.

An, Yang et al., "Contrast Sensitivity Measurement in Dry Eyes," Int J Ophthalmol, vol. 10, No. 3, Mar. 2010, pp. 488-491.

(56) References Cited

OTHER PUBLICATIONS

Arndt, G. Dickey et al., "Microwave Treatment of Prostate Cancer and Hyperplasia," NASA Tech Briefs, Jun. 2005, 1 page.
Author Unknown, "Blepharitis," The Eye Digest, The Dry Eye Research Center, University of Illinois at Chicago, 2003, 3 pages.
Author Unknown, "Introduction to the Report of the International Dry Eye WorkShop (2007)," The Ocular Surface, vol. 5, No. 2, Apr. 2007, pp. 69-70.
Author Unknown, "Keratoconjunctivitis Sicca" Wikipedia, http://en.wikipedia.org/wiki/keratoconjunctivitis_sicca, Nov. 2006, 4 pages.
Author Unknown, "Measurement of Intraocular Pressure" Biomedical Foundations of Ophthalmology, Intraocular Pressure, vol. 2, Chapter 7, Circa 1982, 6 pages (pp. 11-16).
Author Unknown, "Thermographic Camera" Wikipedia, http://en.wikipedia.org/wiki/thermographic_camera, Sep. 2006, 4 pages.
Bartlett, Hannah, et al. "New Perspectives on the Investigation and Treatment of Dry Eye Syndrome—Part 1" Optician, vol. 231, No. 6038, Feb. 2006, 9 pages (pp. 27-37).
Begley, Carolyn, G., et al., "Relationship Between Symptom Profile and Clinical Signs Among Dry Eye Patients" Circa 2003, 1 page.
Begley, Carolyn, G., et al., "The Relationship Between Habitual Patient-Reported Symptoms and Clinical Signs among Patients with Dry Eye of Varying Severity" Investigative Ophthalmology & Visual Science, vol. 44, No. 11, Nov. 2003, 9 pages (pp. 4753-4761).
Behrens, Ashley, MD, "Interferometry for the Detection of Dry Eye," Cataract & Refractive Surgery Today Europe, Nov./Dec. 2008. pp. 57-58.
Behrens, Ashley, MD, "Multiwavelength Interferometry is Creating a New Understanding of the Tear Film," Refractive Eyecare, Oct. 2009, from www.refractiveeyecare.com, 5 pages.
Berliner, M. L, M.D., "The Margins of the Eyelid" Chapter Eight, Biomicroscopy of the Eye, Slit Lamp Microscopy of the Living Eye, vol. 1, Medical Book Department of Harper & Brothers, NYC, Paul B. Hoeber, Inc., 1949, 5 pages (pp. 252-257).
Blackie, Caroline et al., "The Relationship Between Dry Eye Symptoms and Lipid Layer Thickness," Cornea, vol. 28, No. 7, Aug. 2009, pp. 789-794.
Borchman, Douglas, et al., "Temperature-Induced Conformational Changes in Human Tear Lipids Hydrocarbon Chains" Biopolymers, vol. 87, No. 2-3, Jun. 13, 2007, pp. 124-133 (10 pages).
Boyer, Kim L. et al., "Resilient Subclass Discriminant Analysis with Application to Prelens Tear Film Interferometry," Proceedings, Lecture Notes in Computer Science, vol. 6718/2011, MCPR, Cancun, Mexico, Jun. 29-Jul. 2, 2011, pp. 1-11.
Bron, A.J. et al., "Functional Aspects of the Tear Film Lipid Layer," Experimental Eye Research, vol. 78, 2004, pp. 347-360.
Bron, A.J. et al., "The Contribution of Meibomian Disease to Dry Eye," Ocul. Surf., vol. 2, 2004, pp. 149-164.
Bron, Anthony J., BSc, FRCS, FCOphth, et al., "The Ocular Appendages: Eyelids, Conjunctiva and Lacrimal Apparatus" Chapter 2, Wolff's Anatomy of the Eye and Orbit, Eighth Edition, Chapman & Hall Medical, Jan. 1997, 12 pages (pp. 30-42).
Carrington, S. D., et al., "Polarized Light Biomicroscopic Observations on the Pre-Corneal Tear Film" J. Small Anim. Pract., vol. 28, 1987, 20 pages (pp. 605-622).
Craig, J.P. et al., "Importance of the Lipid Layer in Human Tear Film Stability and Evaporation," Optometry and Visual Science, vol. 70, No. 1, 1997, pp. 8-13.
Cruz, Daniele, "Dry Eye Syndrome More Widespread than Predicted" Ocular Surgery News, U.S. Edition, May 2007, 1 page.
Cruz, Daniele, "Surgeon: Early Treatment Key to Avoiding Dry Eye Progression" Ocular Surgery News, U.S. Edition, May 2007, 1 page.
Danjo, Yukitaka, et al., "Measurement of the Precorneal Tear Film Thickness with a Non-Contact Optical Interferometry Film Thickness Measurement System" Jpn J Ophthal., vol. 38, 1994, 7 pages (pp. 260-266).
De Paiva, Cintia S., et al., "Diagnostic Approaches to Lacrimal Keratoconjunctivitis," Dry Eye and Ocular Surface Disorders, New York, NY: Marcel Dekker, 2004, pp. 269-270.
Di Pascuale, Mario A., M.D., et al., "Lipid Tear Deficiency in Persistent Dry Eye After Laser In Situ Keratomileusis and Treatment Results of New Eye-Warming Device" J Cataract Refract. Surg., vol. 31, ASCRS and ESCRS, Elsevier Inc., 2005, 9 pages (pp. 1741-1749).
Di Pascuale, Mario A., M.D., et al., "Sequential Changes of Lipid Tear Film after the Instillation of a Single Drop of a New Emulsion Eye Drop in Dry Eye Patients" American Academy of Ophthalmology, vol. 111, 2004, 9 pages (pp. 783-791).
Doane, Marshall G., "Abnormalities of the Structure of the Superficial Lipid Layer on the In Vivo Dry-Eye Tear Film" (and critique of same) Lacrimal Gland, Tear Film, and Dry Eye Syndromes, Plenum Press, New York, 1994, 11 pages (pp. 489-493).
Doane, Marshall G., "An Instrument for In Vivo Tear Film Interferometry" (and critique of same), Optometry and Vision Science, vol. 66, No. 6, 1989, 10 pages (pp. 383-388).
Doane, Marshall G., et al., "Tear Film Interferometry as a Diagnostic Tool for Evaluating Normal and Dry-Eye Tear Film" Lacrimal Gland, Tear Film, and Dry Eye Syndromes 2, Plenum Press, New York, 1998, 7 pages (pp. 397-303).
Dogru, M. et al., "New Insights into the Diagnosis and Treatment of Dry Eye," Ocular Surface, vol. 2, No. 2, 2004, pp. 59-74.
Dogru, M. et al., "Strip Meniscometry: A New and Simple Method of Tear Meniscus Evaluation," Invest. Ophthalmol. Vis. Sci., vol. 47, No. 5, May 2006, pp. 1895-1901.
Driver, Paul J., et al., "Meibomian Gland Dysfunction" Major Review, Survey of Ophthalmology, vol. 40, No. 5, Mar.-Apr. 1996, 25 pages (pp. 343-367).
Dubra, Alfredo, et al., "Double Lateral Shearing Interferometer for the Quantitative Measurement of Tear Film Topography" Applied Optics, vol. 44, No. 7, Mar. 2005, 9 pages (pp. 1191-1199).
Elizondo, A.E. et al., "Detection of Blink Related Microtrauma by Kinetic Analysis of Tear Interference Images in Patients with Steven Johnson Syndrome and Toxic Epidermal Necrolysis Syndrome," IOVS, vol. 46, Supp. S, 2005, E-Abstract 2654, 2 pages.
English translation of Japanese patent application announcement 2007-209370, 14 pages.
Eom et al., "Correlation Between Quantitative Measurements of Tear Film Lipid Layer Thickness and Meibomian Gland Loss in Patients with Obstructive Meibomian Gland Dysfunction and Normal Controls," American Journal of Ophthalmology, Jun. 2013, vol. 155, No. 6, Elsevier Inc., pp. 1104-1110.
Ernest, J. Terry, M.D. et al., "Ocular Massage Before Cataract Surgery" Tr. Am. Ophth. Soc., vol. LXXXIII, 1985, 13 pages (pp. 205-217).
European Search Report dated Jan. 20, 2012, for European Patent Application No. 11183259.8, 11 pages.
European Search Report for patent application 08732520.5 dated Feb. 24, 2012, 8 pages.
Extended European Search Report and Written Opinion for patent application 10759411.1-1657 dated May 14, 2013, 9 pages.
Examination Report for European patent application 11183259.8-1657 dated May 8, 2013, 7 pages.
Fanning, Gary L., M.D., "Ocular Compression: A Review," Oasis Newsletter, Ophthalmic Anesthesia Society, Summer 2006, http://www.eyeanesthesia.org/newsletter/pdf/oasis_summer06.pdf, 7 pages.
Fenimore, C.P., et al., "Assessment of Resolution and Dynamic Range for Digital Cinema" National Institute of Standards and Technology, Gaithersburg, MD, Circa 2002, 8 pages.
Finlayson, Graham, et al., "Hue that is Invariant to Brightness and Gamma" School of Information Systems, University of East Anglia, Norwich, United Kingdom, Circa 2002, 9 pages (pp. 303-312).
First Office Action for Chinese patent application 201080024927.9 dated May 13, 2013, 16 pages.
Final Office Action for U.S. Appl. No. 12/633,057 dated Apr. 6, 2011, 6 pages.
Non-final Office Action for U.S. Appl. No. 12/633,057 dated Aug. 19, 2010, 8 pages.
Notice of Allowance for U.S. Appl. No. 11/900,314 dated Jan. 25, 2012, 7 pages.
Non-final Office Action for U.S. Appl. No. 11/900,314 dated Aug. 22, 2011, 26 pages.

(56) References Cited

OTHER PUBLICATIONS

Non-final Office Action for U.S. Appl. No. 12/798,325 dated Jan. 27, 2012, 15 pages.
Non-final Office Action for U.S. Appl. No. 12/798,325 dated Aug. 30, 2012, 16 pages.
Notice of Allowance for U.S. Appl. No. 12/798,325 dated Feb. 15, 2013, 9 pages.
Notice of Allowance for U.S. Appl. No. 12/798,325 dated May 29, 2013, 10 pages.
Notice of Allowance for U.S. Appl. No. 29/329,613 dated Feb. 4, 2010, 7 pages.
Notice of Allowance for U.S. Appl. No. 29/329,613 dated Nov. 13, 2009, 7 pages.
Non-Final Rejection dated Apr. 20, 2012, for U.S. Appl. No. 12/798,275, 15 pages.
Final Office Action for U.S. Appl. No. 12/798,275 dated Nov. 20, 2012, 16 pages.
Reply to Final Office Action for U.S. Appl. No. 12/798,275, filed Jan. 29, 2013, 6 pages.
Advisory Action for U.S. Appl. No. 12/798,275 dated Feb. 5, 2013, 9 pages.
Non-final Office Action for U.S. Appl. No. 12/798,275 dated Jul. 30, 2013, 15 pages.
Notice of Allowance for U.S. Appl. No. 12/798,326 dated Aug. 29, 2011, 9 pages.
Non-final Office Action for U.S. Appl. No. 12/798,326 dated Jun. 28, 2011, 19 pages.
Non-final Office Action for U.S. Appl. No. 12/798,326 dated Mar. 29, 2011, 23 pages.
Notice of Allowance for U.S. Appl. No. 12/798,324 dated Apr. 2, 2012, 9 pages.
Non-final Office Action for U.S. Appl. No. 12/798,324 dated Dec. 15, 2011, 27 pages.
Non-final Office Action for U.S. Appl. No. 13/455,628 dated Aug. 29, 2012, 18 pages.
Final Office Action for U.S. Appl. No. 13/455,628 dated May 10, 2013, 9 pages.
Notice of Allowance for U.S. Appl. No. 13/455,628 dated Jul. 12, 2013, 8 pages.
Translation of Notice of Rejection for Japanese patent application 2010-513285 dated Nov. 6, 2012, 4 pages.
Non-final Office Action for U.S. Appl. No. 13/195,353 dated May 3, 2013, 5 pages.
Notice of Allowance for U.S. Appl. No. 13/195,353 dated Jul. 26, 2013, 9 pages.
Fagehi, Raied et al., "Contact Lens In Vitro Wettability by Interferometry Measures of Drying Dynamics," Eye & Contact Lens, vol. 39, No. 6, Contact Lens Association of Ophthalmologists, Nov. 2013, pp. 365-375.
Finis et al., "Evaluation of lipid layer thickness measurement of the tear film as a diagnostic tool for Meibomian gland dysfunction," Cornea, vol. 32, No. 12, Dec. 2013, Lippincott Williams & Wilkins, 5 pages.
Lu, Hui et al., "Combination of Optical Coherence Tomography and Reflectometry Technique for Eye Measurement," Proceedings of SPIE, vol. 8567, Ophthalmic Technologies XXIII, 85672C, Mar. 26, 2013, 6 pages.
Lu, Hui et al., "Tear film measurement by optical reflectometry technique," Journal of Biomedical Optics, vol. 19, No. 2, Feb. 2014, 9 pages.
Primeau et al., "Interferometer and analysis methods for the in vitro characterization of dynamic fluid layers on contact lenses," Optical Engineering, vol. 51, No. 6, SPIE, Jun. 1, 2012, 9 pages.
Sweeney, Deborah F., et al., "Tear film stability: A review," Experimental Eye Research, vol. 117, Elsevier Ltd., Dec. 2013, pp. 28-38.
Szczesna, Dorota H. et al., "Interferometric measurements of dynamic changes of tear film," Journal of Biomedical Optics, vol. 11, No. 3, May 2006, 8 pages.
International Search Report and Written Opinion for PCT/US2013/077117 dated Mar. 18, 2014, 34 pages.

Second Office Action for Chinese patent application 201080024927.9 dated Mar. 21, 2014, 15 pages.
Notice of Rejection for Japanese patent application 2010-513285 dated Dec. 3, 2013, 8 pages.
Translation of Notice of Rejection for Japanese patent application 2012-503707 dated Dec. 3, 2013, 3 pages.
Notice of Allowance for U.S. Appl. No. 12/798,275 dated Jan. 2, 2014, 8 pages.
King-Smith, P.E. et al., "Tear film interferometry and corneal surface roughness," Investigative Ophthalmology & Visual Science, vol. 55, No. 4, Apr. 1, 2014, Association for Research in Vision and Ophthalmology Inc., pp. 2614-2618.
Qazi, Yureeda et al., "Image-guided evaluation and monitoring of treatment response in patients with dry eye disease," Graefe's Archive for Clinical and Experimental Ophthalmology, vol. 252, Issue 6, Jun. 2014, Springer Verlag, pp. 857-872.
Wu, Yuan et al., "Correlation between measurement of tear meniscus by anterior segment module of OCT with dry eye signs and symptoms," Chinese Journal of Experimental Ophthalmology, vol. 32, No. 6, Jun. 2014, Henan Institute of Ophthalmology, pp. 541-545.
Notice of Allowance for U.S. Appl. No. 13/870,054 dated Jul. 17, 2014, 9 pages.
Notice of Allowance for U.S. Appl. No. 14/137,105 dated Jul. 18, 2014, 9 pages.
Hwang, Ho Sik et al., "Novel Tear Interferometer Made of Paper for Lipid Layer Evaluation," Cornea, vol. 33, Issue 8, Aug. 2014, pp. 826-831.
Lam, Sin Man et al., "Longitudinal changes in tear fluid lipidome brought about by eyelid-warming treatment in a cohort of meibomian gland dysfunction," Journal of Lipid Research, vol. 55, No. 9, Sep. 2014, American Society for Biochemistry and Molecular Biology, Inc., pp. 1959-1969.
Szczesna, Dorota H. et al., "Application of interferometry for evaluation of the effect of contact lens material on tear film quality," Proceedings of SPIE, vol. 7064, Aug. 11, 2008, SPIE, 9 pages.
International Preliminary Report on Patentability for PCT/US2013/038116, dated Nov. 6, 2014, 11 pages.
International Preliminary Report on Patentability for PCT/US2013/038149, dated Nov. 6, 2014, 17 pages.
International Search Report and Written Opinion for PCT/US2014/036636, dated Oct. 2, 2014, 9 pages.
International Search Report and Written Opinion for PCT/US2014/036780, dated Nov. 13, 2014, 9 pages.
Notification of Reasons of Refusal for Japanese Patent Application No. 2016-512105, dated Apr. 10, 2018, 6 pages.
Notice of Acceptance for Australian Patent Application No. 2014259619, dated Aug. 13, 2019, 4 pages.
Notification of Deficiencies for Israeli Patent Application No. 242340, dated Jul. 4, 2019, 16 pages.
Notice of Allowance for U.S. Appl. No. 15/791,615, dated Aug. 15, 2019, 8 pages.
Non-Final Office Action for U.S. Appl. No. 16/008,619, dated Jul. 10, 2019, 15 pages.
Non-Final Office Action for U.S. Appl. No. 16/251,332, dated Jul. 11, 2019, 6 pages.
Examination Report No. 2 for Australian Patent Application No. 2014259619, dated Jan. 17, 2019, 3 pages.
Final Office Action for Japanese Patent Application No. 2016-512105, dated Dec. 5, 2018, 3 pages.
Non-Final Office Action for U.S. Appl. No. 15/791,615, dated Feb. 5, 2019, 15 pages.
Examination Report for European Patent Application No. 10759411.1, dated Apr. 12, 2019, 4 pages.
Final Office Action for U.S. Appl. No. 15/791,615, dated Jun. 6, 2019, 15 pages.
Corrected Notice of Allowability, Interview Summary, and AFCP 2.0 Decision for U.S. Appl. No. 14/269,646, dated Apr. 4, 2019, 10 pages.
Examination Report No. 3 for Australian Patent Application No. 2014259619, dated Jun. 13, 2019, 3 pages.
Notice of Allowance for U.S. Appl. No. 14/543,583, dated Jun. 12, 2017, 8 pages.

(56) References Cited

OTHER PUBLICATIONS

Notice of Allowance for U.S. Appl. No. 14/299,504, dated Sep. 16, 2016, 7 pages.
Corrected Notice of Allowance for U.S. Appl. No. 14/299,504, dated Feb. 21, 2017, 4 pages.
Corrected Notice of Allowance for U.S. Appl. No. 14/299,504, dated Mar. 17, 2017, 4 pages.
Notice of Allowance for U.S. Appl. No. 14/299,504, dated Apr. 5, 2017, 7 pages.
Non-Final Office Action for U.S. Appl. No. 15/143,834, dated Sep. 12, 2016, 5 pages.
Notice of Allowance for U.S. Appl. No. 15/143,834, dated Jan. 27, 2017, 8 pages.
Non-Final Office Action for U.S. Appl. No. 15/152,624, dated Sep. 27, 2016, 5 pages.
Notice of Allowance for U.S. Appl. No. 15/152,624, dated Jan. 27, 2017, 7 pages.
Final Office Action for U.S. Appl. No. 13/870,214, dated Jul. 25, 2016, 12 pages.
Notice of Allowance for U.S. Appl. No. 13/870,214, dated Dec. 2, 2016, 7 pages.
Non-Final Office Action for U.S. Appl. No. 14/268,647, dated Dec. 12, 2016, 25 pages.
Non-Final Office Action for U.S. Appl. No. 14/269,646, dated Jul. 27, 2016, 19 pages.
Final Office Action for U.S. Appl. No. 14/269,646, dated Feb. 8, 2017, 34 pages.
Advisory Action for U.S. Appl. No. 14/269,646, dated May 11, 2017, 4 pages.
Karpecki, Paul M. et al., "Meibomian Gland Dysfunction (MGD) Treatment for the Relief of Evaporative Dry Eye Disease: A safety assessment of the iLux™ system on healthy volunteers," 8th International Conference on the Tear Film & Ocular Surface: Basic Science and Clinical Relevance, Conference Poster, Sep. 7-10, 2016, Montpellier, France, Tear Film Innovations, Inc., 1 page.
Hwang, Hyeonha et al., "Image-based quantitative analysis of tear film lipid layer thickness for meibomian gland evaluation," BioMedical Engineering Online, vol. 16, Dec. 2017, Springer, 15 pages.
Matsumoto, Yukihiro, et al., "Increased Tear Evaporation in a Patient with Ectrodactyly-Ectodermal Dysplasia-Clefting Syndrome," Japanese Journal of Ophthalmology, vol. 48, No. 4, Jul. 2004, pp. 372-375.
Examination Report for European Patent Application No. 14792343.7, dated Sep. 5, 2017, 5 pages.
Non-Final Office Action for U.S. Appl. No. 15/608,308, dated Sep. 5, 2017, 17 pages.
Notice of Allowance for U.S. Appl. No. 15/608,308, dated Feb. 16, 2018, 7 pages.
Non-Final Office Action for U.S. Appl. No. 15/615,244, dated Sep. 5, 2017, 6 pages.
Notice of Allowance for U.S. Appl. No. 15/615,244, dated Feb. 6, 2018, 7 pages.
Non-Final Office Action for U.S. Appl. No. 15/589,146, dated Sep. 18, 2017, 13 pages.
Notice of Allowance for U.S. Appl. No. 15/589,146, dated Feb. 12, 2018, 7 pages.
Notice of Allowance for U.S. Appl. No. 14/268,647, dated Aug. 28, 2017, 10 pages.
Non-Final Office Action for U.S. Appl. No. 14/269,646, dated Jan. 12, 2018, 41 pages.
Summons to attend oral proceedings for European Patent Application No. 10759411.1, dated Dec. 3, 2018, 8 pages.
Examination Report for European Patent Application No. 14792343.7, dated Dec. 11, 2018, 4 pages.
Notice of Allowance for U.S. Appl. No. 15/995,612, dated Nov. 15, 2018, 8 pages.
Notice of Allowance, Interview Summary, and AFCP 2.0 Decision for U.S. Appl. No. 14/269,646, dated Nov. 21, 2018, 21 pages.

Corrected Notice of Allowability, Interview Summary, and AFCP 2.0 Decision for U.S. Appl. No. 14/269,646, dated Dec. 26, 2018, 19 pages.
Office Action for Chinese Patent Application No. 201210500620.2, dated Sep. 3, 2014, 18 pages.
Corrected Notice of Allowability for U.S. Appl. No. 13/870,054 dated Nov. 14, 2014, 5 pages.
Corrected Notice of Allowability for U.S. Appl. No. 14/137,105, dated Sep. 25, 2014, 4 pages.
Third Office Action for Chinese Patent Application No. 201080024927.9, dated Nov. 26, 2014, 7 pages.
Chan, Xiong, et al., "Influence of watching video display terminal on ocular surface and application of non-invasive ocular surface analyzer," Chinese Journal of Experimental Ophthalmology, vol. 34, Issue 5, May 2016, pp. 443-447 (Abstract).
Chan, Xiong, et al., "Influence of watching video display terminal on ocular surface and application of non-invasive ocular surface analyzer," Chinese Journal of Experimental Ophthalmology, vol. 34, Issue 5, May 2016, pp. 443-447 (Google Translation).
Finis, D. et al., "Factors Influencing the Measurement of Tear Film Lipid Layer Thickness with Interferometry," Klin Monatsbl Augenheilkd, vol. 231, No. 6, Jun. 2014, pp. 603-610.
Micali, Jason D. et al., "Dynamic measurement of the corneal tear film with a Twyman-Green interferometer," Interferometry XVII: Advanced Applications, Aug. 18, 2014, San Diego, California, Proceedings of SPIE, vol. 9204, 6 pages.
Examination Report for European Patent Application No. 11183259.8 dated Mar. 23, 2015, 8 pages.
Examination Report for European Patent Application No. 08732520.5, dated Jul. 13, 2015, 6 pages.
Examination Report for European Patent Application No. 10759411.1 dated Mar. 23, 2015, 7 pages.
International Preliminary Report on Patentability for PCT/US2013/039395, dated Jun. 4, 2015, 10 pages.
International Preliminary Report on Patentability for International Patent Application No. PCT/US2013/077117, dated Jul. 2, 2015, 33 pages.
International Preliminary Report on Patentability for International Patent Application No. PCT/US2014/036636, dated Nov. 12, 2015, 8 pages.
International Preliminary Report on Patentability for International Patent Application No. PCT/US2014/036780, dated Nov. 12, 2015, 8 pages.
International Search Report and Written Opinion for PCT/US2014/065992, dated Mar. 3, 2015, 9 pages.
International Preliminary Report on Patentability for PCT/US2014/065992, dated May 26, 2016, 8 pages.
Second Office Action for Chinese Patent Application No. 201210500620.2, dated Mar. 30, 2015, 14 pages.
Third Office Action for Chinese Patent Application No. 201210500620.2, dated Jul. 27, 2015, 17 pages.
Fourth Office Action for Chinese Patent Application No. 201210500620.2, dated Dec. 31, 2015, 8 pages.
First Office Action and Examination Search Report for Canadian Patent Application No. 2,757,486, dated Dec. 22, 2015, 5 pages.
Notice of Rejection for Japanese Patent Application No. 2014-238420, dated Oct. 13, 2015, 4 pages.
Decision to Grant for Japanese Patent Application No. 2014-238420, dated Jun. 7, 2016, 2 pages.
Notice of Preliminary Rejection for Korean Patent Application No. 10-2011-7026079, dated Apr. 28, 2016, 15 pages.
Non-Final Office Action for U.S. Appl. No. 14/543,583, dated Mar. 22, 2016, 17 pages.
Non-Final Office Action for U.S. Appl. No. 14/299,504, dated Aug. 13, 2015, 14 pages.
Notice of Allowance for U.S. Appl. No. 14/299,504, dated Feb. 3, 2016, 8 pages.
Corrected Notice of Allowance for U.S. Appl. No. 14/299,504, dated Jun. 30, 2016, 4 pages.
Notice of Allowance for U.S. Appl. No. 14/543,931, dated Jan. 11, 2016, 8 pages.
Non-Final Office Action for U.S. Appl. No. 13/870,214, dated Nov. 10, 2015, 11 pages.

(56) References Cited

OTHER PUBLICATIONS

Non-Final Office Action for U.S. Appl. No. 13/886,383, dated Jun. 25, 2015, 22 pages.
Arita, Reiko, et al., "Tear Interferometric Patterns Reflect Clinical Tear Dynamics in Dry Eye Patients," Investigative Ophthalmology & Visual Science, vol. 57, Issue 8, Jul. 2016, Association for Research in Vision and Ophthalmology Inc., pp. 3928-3934.
Ji, Yong Woo et al., "Automated Measurement of Tear Film Dynamics and Lipid Layer Thickness for Assessment of Non-Sjögren Dry Eye Syndrome With Meibomian Gland Dysfunction," Cornea, vol. 36, Issue 2, Feb. 2017, Wolters Kluwer Health, Inc., pp. 176-182.
Micali, Jason D., et al., "Dual interferometer for dynamic measurement of corneal topography," Journal of Biomedical Optics, vol. 21, Issue 8, Aug. 31, 2016, SPIE, pp. 085007-1 to 085007-19.
Examination Report for European Patent Application No. 11183259.8, dated Feb. 14, 2017, 11 pages.
Examination Report for European Patent Application No. 10759411.1, dated Feb. 14, 2017, 10 pages.
Extended European Search Report for European Patent Application No. 13864124.6, dated Jun. 24, 2016, 4 pages.
First Office Action and Search Report for Chinese Patent Application No. 201480031610.6 dated May 2, 2017, 21 pages.
Extended European Search Report for European Patent Application No. 14792343.7, dated Nov. 16, 2016, 7 pages.
International Search Report and Written Opinion for International Patent Application No. PCT/US2008/057578, dated Aug. 26, 2008, 11 pages.
International Preliminary Report on Patentability for International Patent Application No. PCT/US2008/057578, dated Dec. 22, 2009, 11 pages.
International Search Report and Written Opinion for International Patent Application No. PCT/US2008/057581, dated Aug. 26, 2008, 11 pages.
International Preliminary Report on Patentability for International Patent Application No. PCT/US2008/057581, dated Dec. 22, 2009, 11 pages.
Second Office Action and Examination Search Report for Canadian Patent Application No. 2,757,486, dated Dec. 15, 2016, 7 pages.
Notice of Allowance for Korean Patent Application No. 10-2011-7026079, dated Jan. 16, 2017, 4 pages.
International Search Report and Written Opinion for International Patent Application No. PCT/US2010/029645, dated Jun. 4, 2010, 15 pages.
International Preliminary Report on Patentability for International Patent Application No. PCT/US2010/029645, dated Oct. 13, 2011, 12 pages.
Non-Final Office Action for U.S. Appl. No. 14/543,583, dated Sep. 13, 2016, 14 pages.
Final Office Action for U.S. Appl. No. 14/543,583, dated Mar. 1, 2017, 14 pages.
Advisory Action for U.S. Appl. No. 14/543,583, dated May 11, 2017, 3 pages.
Examination Report No. 1 for Standard Patent Application for Australian Patent Application No. 2014259619, dated Aug. 10, 2018, 4 pages.
Examination Report for European Patent Application No. 14792343.7, dated Aug. 21, 2018, 4 pages.
Examination Report Under Sections 12 & 13 of the Patents Act for Indian Patent Application No. 2026/MUMNP/2011, dated Oct. 5, 2018, 6 pages.
Applicant-Initiated Interview Summary for U.S. Appl. No. 14/269,646, dated Oct. 16, 2018, 4 pages.
Examination Report for European Patent Application No. 13864124.6, dated Dec. 4, 2019, 4 pages.
First Office Action for Chinese Patent Application No. 201810288156.2, dated Dec. 19, 2019, 18 pages.
Notice of Allowance for U.S. Appl. No. 16/008,619, dated Oct. 30, 2019, 8 pages.
Notice of Allowance for U.S. Appl. No. 16/251,332, dated Oct. 22, 2019, 8 pages.
Decision to Grant for Japanese Patent Application No. 2016-512105, dated Oct. 9, 2019, 5 pages.
First Office Action and Examination Search Report for Canadian Patent Application No. 3,010,578, dated Oct. 29, 2019, 9 pages.

\* cited by examiner

| LIPID THICKNESS (nm) N=1.477 | OPTICAL PATHLENGTH (nm) | PHANTOM THICKNESS (nm) |
|---|---|---|
| 20 | 56 | 17 |
| 60 | 167 | 52 |
| 90 | 250 | 78 |
| 130 | 361 | 113 |
| 170 | 473 | 147 |
| 200 | 556 | 173 |
| 230 | 639 | 199 |
| 256 | 712 | 222 |
| 280 | 778 | 243 |

FIG. 47

| EXPECTED PHANTOM THICKNESS (nm) | MEASURED PHANTOM THICKNESS (nm) | OPTICAL PATHLENGTH (nm) | CORRESPONDING LIPID THICKNESS (nm) |
|---|---|---|---|
| 17 | 20.76 | 56 | 24.19 |
| 52 | --- | 167 | 60.60 |
| 78 | 70.90 | 250 | 82.63 |
| 113 | 108.55 | 361 | 126.50 |
| 147 | 146.35 | 473 | 170.56 |
| 173 | 171.20 | 556 | 199.52 |
| 199 | 198.69 | 639 | 231.55 |
| 222 | 211.04 | 712 | 245.94 |
| 243 | 238.51 | 778 | 277.96 |

FIG. 49

| THICKNESS (nm) | R | G | B | HUE (°) | CHROMA | LIGHTNESS |
|---|---|---|---|---|---|---|
| 20.76 | 99 | 103 | 108 | 214 | 0.03 | 0.41 |
| 52 | 147 | 160 | 175 | 212 | 0.11 | 0.63 |
| 70.90 | 173 | 184 | 193 | 208 | 0.08 | 0.72 |
| 108.55 | 176 | 162 | 139 | 38 | 0.15 | 0.62 |
| 146.35 | 123 | 101 | 89 | 21 | 0.13 | 0.42 |
| 171.20 | 94 | 96 | 124 | 236 | 0.12 | 0.43 |
| 198.69 | 96 | 131 | 178 | 215 | 0.32 | 0.54 |
| 211.04 | 109 | 150 | 188 | 209 | 0.31 | 0.58 |
| 238.51 | 149 | 175 | 164 | 155 | 0.10 | 0.64 |

*FIG. 50*

METHODS AND APPARATUSES FOR DETERMINING CONTACT LENS INTOLERANCE IN CONTACT LENS WEARER PATIENTS BASED ON DRY EYE TEAR FILM CHARACTERISTIC ANALYSIS AND DRY EYE SYMPTOMS

PRIORITY APPLICATIONS

The present application is a continuation application of, and claims priority to, co-pending U.S. patent application Ser. No. 14/268,647, now published as U.S. Patent Application Publication No. 2017/0245750, entitled "METHODS AND APPARATUSES FOR DETERMINING CONTACT LENS INTOLERANCE IN CONTACT LENS WEARER PATIENTS BASED ON DRY EYE TEAR FILM CHARACTERISTIC ANALYSIS AND DRY EYE SYMPTOMS," filed on May 2, 2014, which is a continuation in part of U.S. patent application Ser. No. 12/798,275 entitled "OCULAR SURFACE INTERFEROMETRY (OSI) DEVICES AND SYSTEMS FOR IMAGING, PROCESSING, AND/OR DISPLAYING AN OCULAR TEAR FILM," filed on Apr. 1, 2010, issued as U.S. Pat. No. 8,746,883, which claims priority to U.S. Provisional Patent Application Ser. No. 61/211,596 entitled "OCULAR SURFACE INTERFEROMETRY (OSI) METHODS FOR IMAGING PROCESSING, AND/OR DISPLAYING AN OCULAR TEAR FILM," filed on Apr. 1, 2009, all of which are incorporated herein by reference in their entireties.

U.S. patent application Ser. No. 14/268,647, to which the present application is a continuation application and claims priority, also claims priority to U.S. Provisional Patent Application Ser. No. 61/819,125 entitled "APPARATUSES AND METHODS FOR DETERMINING CONTACT LENS INTOLERANCE AND DIAGNOSING, MEASURING, AND/OR ANALYZING DRY EYE CONDITIONS AND SYMPTOMS IN CONTACT LENS WEARERS," filed on May 3, 2013, which is incorporated herein by reference in its entirety.

U.S. patent application Ser. No. 14/268,647, to which the present application is a continuation application and claims priority, also claims priority to U.S. Provisional Patent Application Ser. No. 61/904,562 entitled "OCULAR SURFACE INTERFEROMETRY (OSI) SYSTEM AND METHODS FOR IMAGING, PROCESSING, AND/OR DISPLAYING AN OCULAR TEAR FILM AND MEIBOMIAN GLAND FEATURES," filed on Nov. 15, 2013, which is incorporated herein by reference in its entirety.

RELATED APPLICATIONS

The present application is related to U.S. patent application Ser. No. 12/798,325 entitled "OCULAR SURFACE INTERFEROMETRY (OSI) METHODS FOR IMAGING, PROCESSING, AND/OR DISPLAYING AN OCULAR TEAR FILM," filed on Apr. 1, 2010, issued as U.S. Pat. No. 8,545,017, which claims priority to U.S. Provisional Patent Application Ser. No. 61/211,596 entitled "OCULAR SURFACE INTERFEROMETRY (OSI) METHODS FOR IMAGING, PROCESSING, AND/OR DISPLAYING AN OCULAR TEAR FILM," filed on Apr. 1, 2009, which are both incorporated herein by reference in their entireties.

The present application is also related to U.S. patent application Ser. No. 12/798,326 entitled "OCULAR SURFACE INTERFEROMETRY (OSI) METHODS FOR IMAGING AND MEASURING OCULAR TEAR FILM LAYER THICKNESS(ES)," filed on Apr. 1, 2010, issued as U.S. Pat. No. 8,092,023, which claims priority to U.S. Provisional Patent Application Ser. No. 61/211,596 entitled "OCULAR SURFACE INTERFEROMETRY (OSI) METHODS FOR IMAGING, PROCESSING, AND/OR DISPLAYING AN OCULAR TEAR FILM," filed on Apr. 1, 2009, which are both incorporated herein by reference in their entireties.

The present application is also related to U.S. patent application Ser. No. 12/798,324 entitled "OCULAR SURFACE INTERFEROMETRY (OSI) DEVICES AND SYSTEMS FOR IMAGING AND MEASURING OCULAR TEAR FILM LAYER THICKNESS(ES)," filed on Apr. 1, 2010, issued as U.S. Pat. No. 8,215,774, which claims priority to U.S. Provisional Patent Application Ser. No. 61/211,596 entitled "OCULAR SURFACE INTERFEROMETRY (OSI) METHODS FOR IMAGING, PROCESSING, AND/OR DISPLAYING AN OCULAR TEAR FILM," filed on Apr. 1, 2009, which are both incorporated herein by reference in their entireties.

The present application is also related to U.S. patent application Ser. No. 13/886,383 entitled "OPTICAL PHANTOMS FOR USE WITH OCULAR SURFACE INTERFEROMETRY (OSI) DEVICES AND SYSTEMS CONFIGURED TO MEASURE TEAR FILM LAYER THICKNESS(ES), AND RELATED USE FOR CALIBRATION," filed on May 3, 2013, which claims priority to U.S. Provisional Patent Application Ser. No. 61/642,688, entitled "OPTICAL PHANTOMS FOR USE WITH OCULAR SURFACE INTERFEROMETRY (OSI) DEVICES AND SYSTEMS CONFIGURED TO MEASURE TEAR FILM LAYER THICKNESS(ES), AND RELATED USE FOR CALIBRATION," filed on May 4, 2012, which are both incorporated herein by reference in their entireties.

The present application is being filed with color versions (3 sets) of the drawings discussed and referenced in this disclosure. Color drawings more fully disclose the subject matter disclosed herein.

FIELD OF THE DISCLOSURE

The technology of the disclosure relates to imaging and analysis of a patient's ocular tear film to determine tear film characteristics relating to dry eye symptoms, including lipid layer deficiency, in contact lens wearers.

BACKGROUND

In the human eye, the precorneal tear film covering ocular surfaces is composed of three primary layers: the mucin layer, the aqueous layer, and the lipid layer. Each layer plays a role in the protection and lubrication of the eye and thus affects dryness of the eye or lack thereof. Dryness of the eye is a recognized ocular disease, which is generally referred to as "dry eye," "dry eye syndrome" (DES), or "keratoconjunctivitis sicca" (KCS). Dry eye can cause symptoms, such as itchiness, burning, and irritation, which can result in discomfort. There is a correlation between the ocular tear film layer thicknesses and dry eye disease. The various different medical conditions and damage to the eye as well as the relationship of the aqueous and lipid layers to those conditions are reviewed in Surv Opthalmol 52:369-374, 2007 and additionally briefly discussed below.

As illustrated in FIG. 1, the precorneal tear film includes an innermost layer of the tear film in contact with a cornea 10 of an eye 11 known as the mucus layer 12. The mucus layer 12 is comprised of many mucins. The mucins serve to retain aqueous in the middle layer of the tear film known as the aqueous layer. Thus, the mucus layer 12 is important in that it assists in the retention of aqueous on the cornea 10 to provide a protective layer and lubrication, which prevents dryness of the eye 11.

A middle or aqueous layer 14 comprises the bulk of the tear film. The aqueous layer 14 is formed by secretion of aqueous by lacrimal glands 16 and accessory tear glands 17 surrounding the eye 11, as illustrated in FIG. 2A. FIG. 2B illustrates the eye 11 in FIG. 2A during a blink. The aqueous, secreted by the lacrimal glands 16 and accessory tear glands 17, is also commonly referred to as "tears." One function of the aqueous layer 14 is to help flush out any dust, debris, or foreign objects that may get into the eye 11. Another important function of the aqueous layer 14 is to provide a protective layer and lubrication to the eye 11 to keep it moist and comfortable. Defects that cause a lack of sufficient aqueous in the aqueous layer 14, also known as "aqueous deficiency," are a common cause of dry eye.

The outermost layer of the tear film, known as the "lipid layer" 18 and also illustrated in FIG. 1, also aids to prevent dryness of the eye. The lipid layer 18 is comprised of many lipids known as "meibum" or "sebum" that is produced by meibomian glands 20 in upper and lower eyelids 22, 24, as illustrated in FIG. 3. This outermost lipid layer is very thin, typically less than 250 nanometers (nm) in thickness. The lipid layer 18 provides a protective coating over the aqueous layer 14 to limit the rate at which the aqueous layer 14 evaporates. Blinking causes the upper eyelid 22 to mall up aqueous and lipids as a tear film, thus forming a protective coating over the eye 11. A higher rate of evaporation of the aqueous layer 14 can cause dryness of the eye. Thus, if the lipid layer 18 is not sufficient to limit the rate of evaporation of the aqueous layer 14, dryness of the eye may result.

For wearers of contact lenses, a widely reported ailment to physicians is intolerance to prolonged contact lens usage. Contact lens wear can contribute to dry eye. A contact lens can disrupt the natural tear film and can reduce corneal sensitivity over time, which can cause a reduction in tear production. In some patients, contact lens wear becomes unmanageable due to pain, irritation, or general decrease of visual acuity due to ocular discomfort. Typical remedies include repetitive eye drop applications, alterations of daily activity, or repeated removal of the contact lenses and return to standard eyeglasses or poor vision. For physicians, a typical treatment regime of revised medications and replacement contact lenses is tried and evaluated until a recommendation to alternative vision correction is employed for the patient. For many of these patients, evaporative dry eye disease is an underlying cause for their contact lens intolerance.

A system for determining which patients would be ideal candidates, or non-candidates for contact lenses, in the presence of ongoing dry eye disease would be of benefit to physicians and patients. Since dry eye disease can be an underlying problem as in the case of meibomian gland dysfunction (MGD) or non-obvious meibomian gland disease, a system that can be predictive of future contact lens problems would be advantageous. For MGD or meibomian gland disease in which dry eye signs are visible to the physician, a system that can qualitatively assess the potential impact of contact lens wear to the patient prospectively would be a benefit to future contact lens wear and the selection of model type.

SUMMARY

Methods and apparatuses for determining contact lens intolerance in contact lens wearer patients based on tear film characteristics analysis and dry eye symptoms are disclosed. An ocular tear film may be affected by contact lens wear. Contact lens wear can contribute to dry eye. A contact lens can disrupt the natural tear film and can reduce corneal sensitivity over time, which can cause a reduction in tear film production. For many patients, evaporative dry eye disease is an underlying cause for their contact lens intolerance. Thus, in embodiments herein, imaging of the ocular tear film is performed during contact lens wear or at time points immediately preceding or following contact lens wear. For example, the imaging may include captured optical wave interference of specularly reflected light from the ocular tear film, when the ocular tear film is illuminated with the light source. An analysis of the image of the ocular tear film is performed to determine one or more tear film characteristics of the ocular tear film. The tear film characteristics can be used to determine the effect or possible effect of contact lens wear on the ocular tear film, and thus be used to determine contact lens intolerance of the patient. As examples, the tear film characteristics used to analyze contact lens intolerance based on images of the ocular tear film involving contact lens wear may include dry eye symptoms, including but not limited to tear film thickness, tear film viscosity, and tear film movement rate in the eye. When referring to tear film herein, it should be noted that such refers to the lipid layer and/or the aqueous layer of the ocular tear film.

In this regard, in one embodiment, a method for diagnosing contact lens intolerance on an ocular tear film of a patient is provided. The method comprises illuminating the ocular tear film of the patient with a contact lens disposed on a patient's eye with a light source. The method also comprises capturing in at least one first image of the ocular tear film without the contact lens disposed on the patient's eye, optical wave interference of specularly reflected light from the ocular tear film, when the ocular tear film is illuminated with the light source. The method also comprises isolating at least one contact lens-based region of interest in the at least one first image where the contact lens is present on the ocular tear film. The method also comprises converting the at least one contact lens-based region of interest in the at least one first image into at least one contact lens-based color-based value. The method also comprises comparing the at least one contact lens-based color-based value to a lipid layer—contact lens layer optical wave interference model. The method also comprises determining a contact lens-based tear film characteristic of the at least one contact lens-based region of interest of the ocular tear film based on the comparison of the at least one contact lens-based color-based value to the lipid layer—contact lens layer optical wave interference model.

In another embodiment, an apparatus for diagnosing contact lens intolerance on an ocular tear film of a patient is provided. The apparatus comprises a light source configured to illuminate the ocular tear film of a patient without a contact lens disposed on a patient's eye. The apparatus also comprises an imaging device configured to capture in at least one first image of the ocular tear film without the contact lens disposed on the patient's eye, optical wave interference of specularly reflected light from the ocular tear film, when the ocular tear film is illuminated with the light source. The apparatus also comprises a computer control system. The computer control system is configured to isolate at least one contact lens-based region of interest in the at least one first image where the contact lens is present on the ocular tear film. The computer control system is also configured to convert the at least one contact lens-based region of interest in the at least one first image into at least one contact lens-based color-based value. The computer control system is also configured to compare the at least one contact lens-based color-based value to a lipid layer—contact lens layer optical wave interference model. The computer control system is also configured to determine a contact lens-based tear film characteristic of the at least one contact lens-based region of interest of the ocular tear film based on the comparison of the at least one contact lens-based color-based value to the lipid layer—contact lens layer optical wave interference model.

In another embodiment, a method for diagnosing contact lens intolerance in a patient is provided. The method comprises illuminating an ocular tear film of a patient having a contact lens disposed on a patient's eye. The method also comprises capturing in at least one first image of the ocular tear film with the contact lens disposed on the patient's eye, optical wave interference of specularly reflected light from the ocular tear film, when the ocular tear film is illuminated. The method also comprises isolating at least one non-contact lens-based region of interest in the at least one first image where the contact lens is not present on the ocular tear film. The method also comprises determining a non-contact lens-based tear film characteristic in the at least one non-contact lens-based region of interest of the at least one first image.

In another embodiment, an apparatus for diagnosing contact lens intolerance in a patient is provided. The apparatus comprises an illuminator configured to illuminate an ocular tear film of a patient having a contact lens disposed on a patient's eye. The apparatus also comprises an imaging device configured to capture in at least one first image of the ocular tear film with the contact lens disposed on the patient's eye, optical wave interference of specularly reflected light from the ocular tear film, when the ocular tear film is illuminated. The apparatus also comprises a computer control system. The computer control system is configured to isolate at least one non-contact lens-based region of interest in the at least one first image where the contact lens is not present on the ocular tear film. The computer control system is also configured to determine a non-contact lens-based tear film characteristic in the at least one non-contact lens-based region of interest of the at least one first image.

Those skilled in the art will appreciate the scope of the present disclosure and realize additional aspects thereof after reading the following detailed description of the preferred embodiments in association with the accompanying drawing figures.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 47 is a table of lipid layer thicknesses of the selected points shown in FIG. 46 along with their corresponding optical path lengths and phantom thicknesses;

FIG. 49 is a table listing exemplary phantom lipid layer thicknesses for nine exemplary sample phantom wedges measured using exemplary ellipsometry along with corresponding biological lipid layer thicknesses;

FIG. 50 is a table that presents a comparison of expected exemplary interference colors from optical phantoms and a theoretical model;

DETAILED DESCRIPTION

The embodiments set forth below represent the necessary information to enable those skilled in the art to practice the disclosure and illustrate the best mode of practicing the disclosure. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Methods and apparatuses for determining contact lens intolerance in contact lens wearer patients based on tear film characteristics analysis and dry eye symptoms are disclosed. An ocular tear film may be affected by contact lens wear. Contact lens wear can contribute to dry eye. A contact lens can disrupt the natural tear film and can reduce corneal sensitivity over time, which can cause a reduction in tear film production. For many patients, evaporative dry eye disease is an underlying cause for their contact lens intolerance. Thus, in embodiments herein, imaging of the ocular tear film is performed during contact lens wear. For example, the imaging may include captured optical wave interference of specularly reflected light from the ocular tear film, when the ocular tear film is illuminated with the light source. An analysis of the image of the ocular tear film is performed to determine one or more tear film characteristics of the ocular tear film. The tear film characteristics can be used to determine the effect or possible effect of contact lens wear on the ocular tear film, and thus be used to determine contact lens intolerance of the patient. As examples, the tear film characteristics used to analyze contact lens intolerance based on images of the ocular tear film involving contact lens wear may include dry eye symptoms, including but not limited to tear film thickness, tear film viscosity, and tear film movement rate in the eye. When referring to tear film herein, it should be noted that such refers to the lipid layer and/or the aqueous layer of the ocular tear film.

Figure 4A:
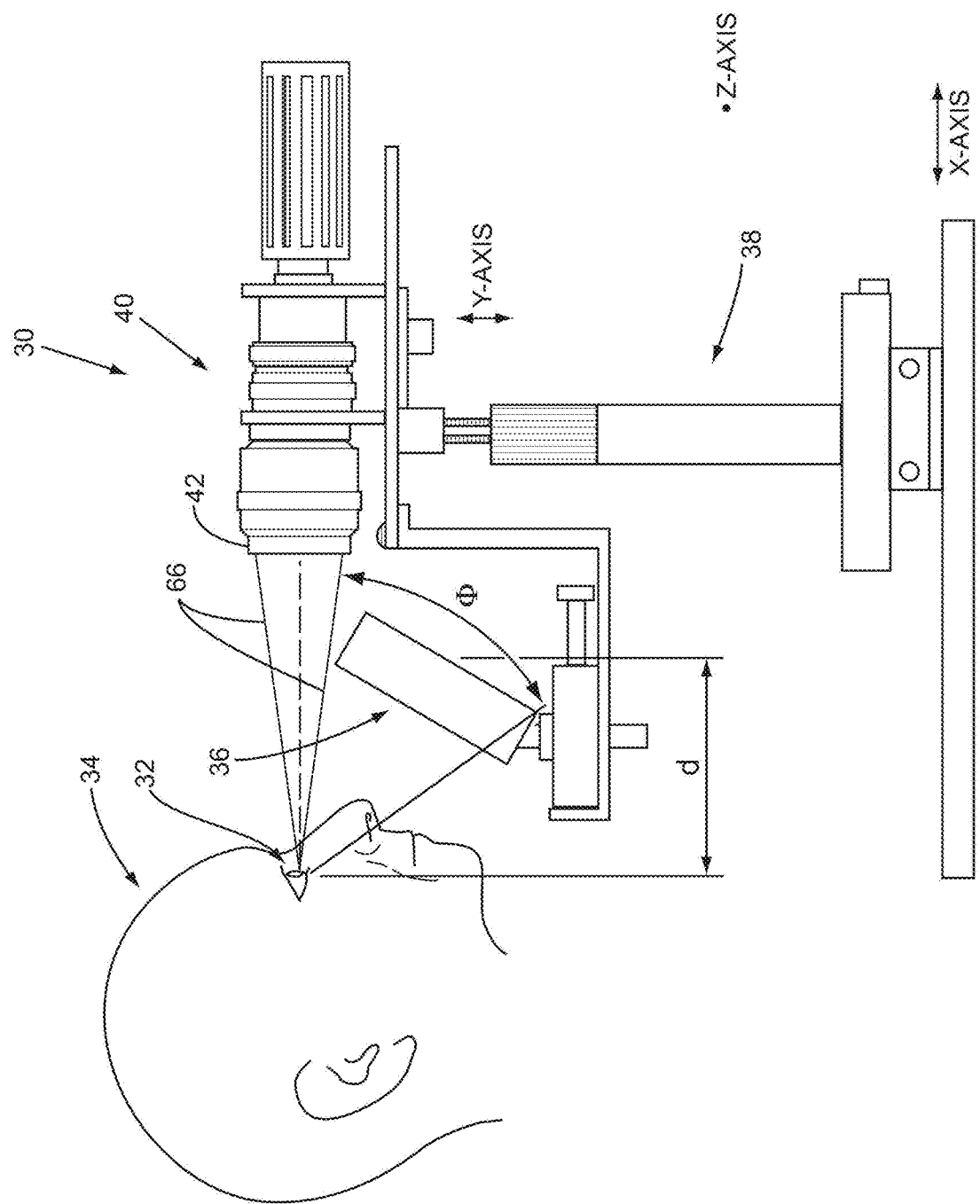
FIGS. 4A and 4B are illustrations of an exemplary light source and imaging device to facilitate discussion of illumination of the tear film and capture of interference interactions of specularly reflected light from the tear film.
Figure 4B:
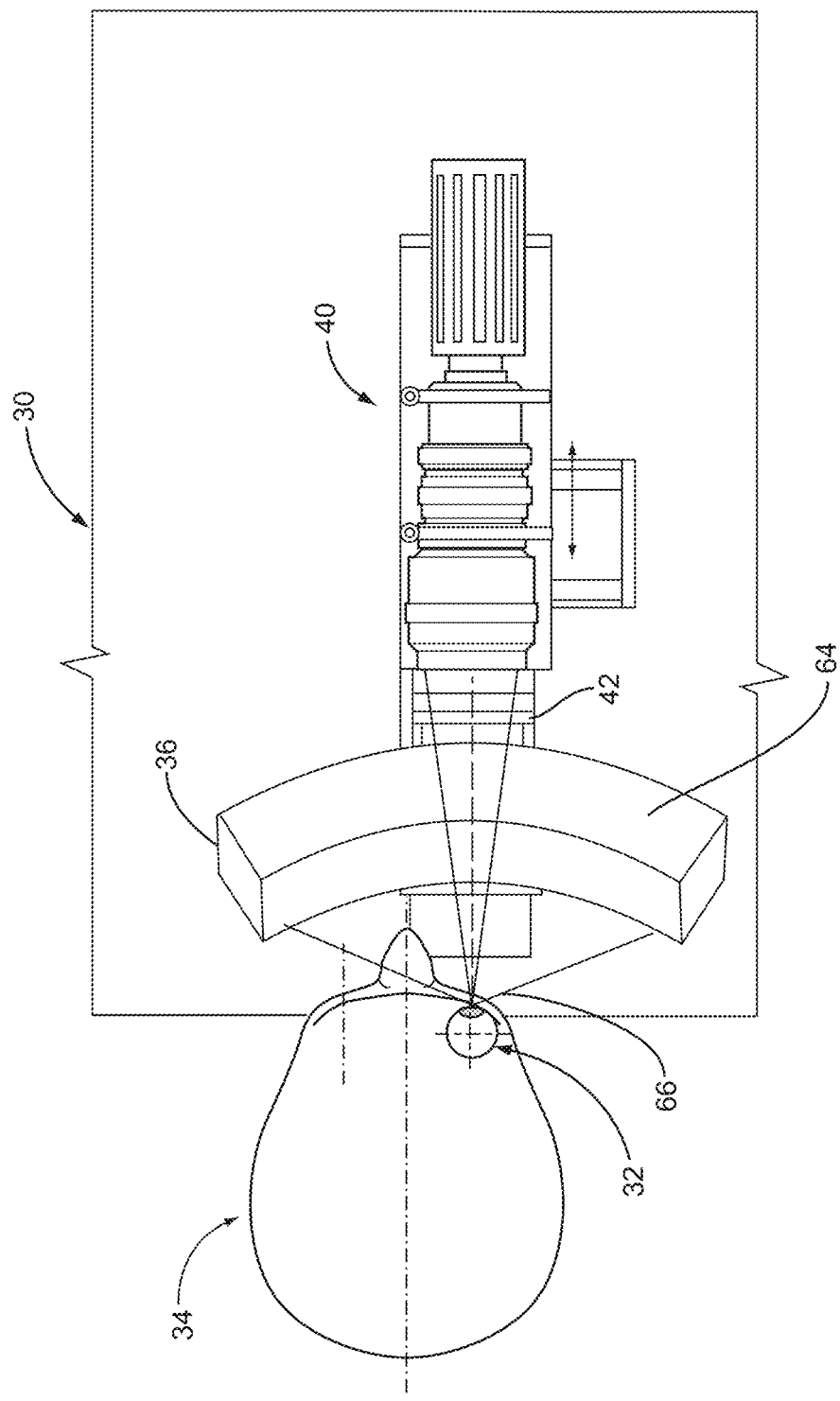

In this regard, FIGS. 4A-4B illustrate a general embodiment of an ocular surface interferometry (OSI) device 30 that can be used to determine contact lens intolerance in contact lens wearer patients based on tear film characteristics analysis and dry eye symptoms. In general, the OSI device 30 is configured to illuminate a patient's ocular tear film, capture images of interference interactions of specularly reflected light from the ocular tear film, and process and analyze the interference interactions to determine tear film characteristics of a contact lens wearer patient. As shown in FIG. 4A, the exemplary OSI device 30 positioned in front of one of the patient's eye 32 is shown from a side view. A top view of the patient 34 in front of the OSI device 30 is illustrated in FIG. 4B. The ocular tear film of a patient's eyes 32 is illuminated with a light source 36 (also referred to herein as "illuminator 36") and comprises a large area light source having a spectrum in the visible region adequate for tear film layer thickness (TFLT) measurement and correlation to dry eye. The illuminator 36 can be a white or multi-wavelength light source.

In this embodiment, the illuminator 36 is a Lambertian emitter and is adapted to be positioned in front of the eye 32 on a stand 38. As employed herein, the terms "Lambertian surface" and "Lambertian emitter" are defined to be a light emitter having equal or substantially equal (also referred to as "uniform" or substantially uniform) intensity in all directions. This allows the imaging of a uniformly or substantially uniformly bright tear film region for determining tear film characteristics of a contact lens wearer patient, as discussed in more detail in this disclosure. The illuminator 36 could also be a multi-light wave illuminator or a monochromatic illuminator. The illuminator 36 in this embodiment, comprises a large surface area emitter, arranged such that rays emitted from the emitter are specularly reflected from the ocular tear film and undergo constructive and destructive interference in tear film layers therein. An image of the patient's 34 lipid layer is the backdrop over which the interference image is seen and it should be as spatially uniform as possible.

Figure 5:
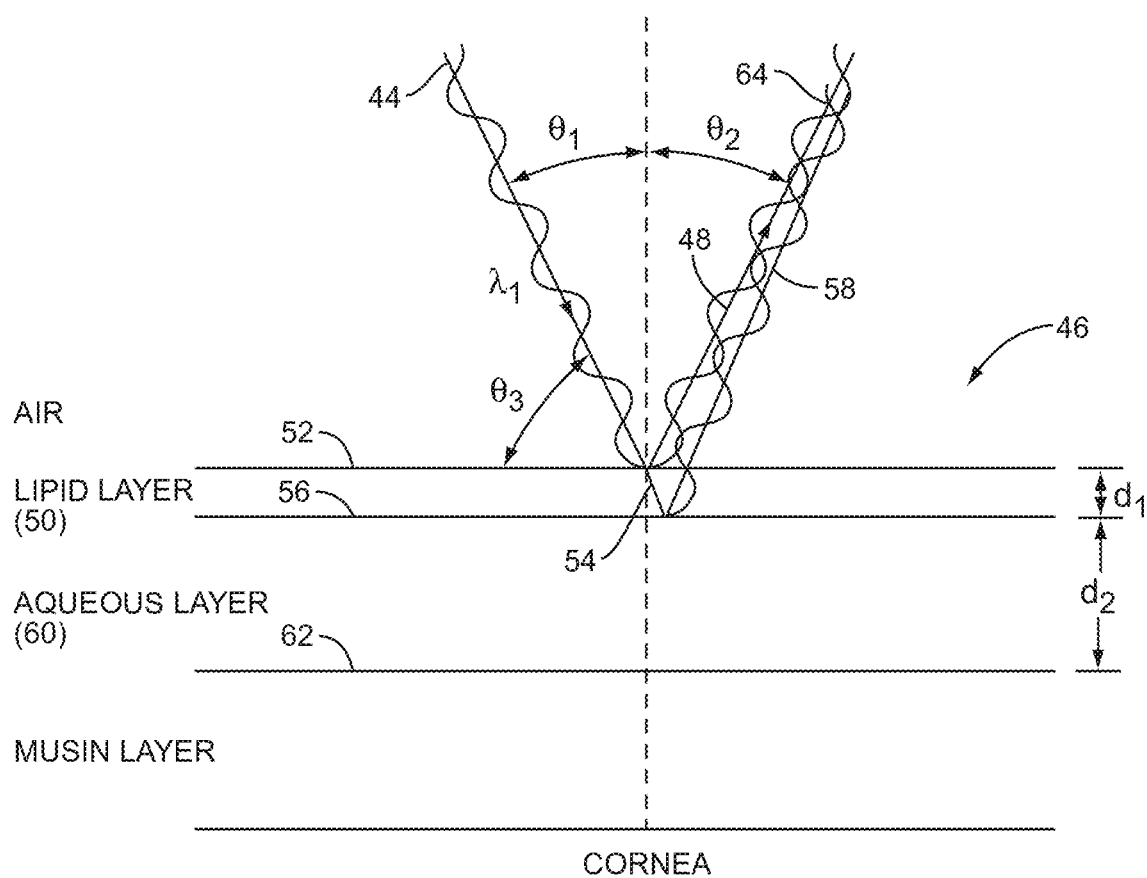
FIG. 5 illustrates (in a microscopic section view) exemplary tear film layers to illustrate how light rays can specularly reflect from various tear film layer transitions.

An imaging device 40 is included in the OSI device 30 and is employed to capture interference interactions of specularly reflected light from the patient's 34 ocular tear film when illuminated by the illuminator 36. The imaging device 40 may be a still or video camera, or other device that captures images and produces an output signal representing information in captured images. The output signal may be a digital representation of the captured images. The geometry of the illuminator 36 can be understood by starting from an imaging lens 42 of the imaging device 40 and proceeding forward to the eye 32 and then to the illuminator 36. The fundamental equation for tracing ray lines is Snell's law, which provides:

$$n1 \sin \Theta_1 = n2 \sin \Theta_2,$$

where "n1" and "n2" are the indexes of refraction of two mediums containing the ray, and $\Theta_1$ and $\Theta_2$ is the angle of the ray relative to the normal from the transition surface. As illustrated in FIG. 5, light rays 44 are directed by the illuminator 36 to an ocular tear film 46. In the case of specularly reflected light 48 that does not enter a lipid layer 50 and instead reflects from an anterior surface 52 of the lipid layer 50, Snell's law reduces down to $\Theta_1 = \Theta_2$, since the index of refraction does not change (i.e., air in both instances). Under these conditions, Snell's law reduces to the classical law of reflection such that the angle of incidence is equal and opposite to the angle of reflectance.

Some of the light rays 54 pass through the anterior surface 52 of the lipid layer 50 and enter into the lipid layer 50, as illustrated in FIG. 5. As a result, the angle of these light rays 54 (i.e., $\Theta_3$) normal to the anterior surface 52 of the lipid layer 50 will be different than the angle of the light rays 44 ($\Theta_1$) according to Snell's law. This is because the index of refraction of the lipid layer 50 is different than the index of refraction of air. Some of the light rays 54 passing through the lipid layer 50 will specularly reflect from the lipid layer-to-aqueous layer transition 56 thereby producing specularly reflected light rays 58. The specularly reflected light rays 48, 58 undergo constructive and destructive interference anterior of the lipid layer 50. The modulations of the interference of the specularly reflected light rays 48, 58 superimposed on the anterior surface 52 of the lipid layer 50 are collected by the imaging device 40 when focused on the anterior surface 52 of the lipid layer 50. Focusing the imaging device 40 on the anterior surface 52 of the lipid layer 50 allows capturing of the modulated interference information at the plane of the anterior surface 52. In this manner, the captured interference information and the resulting determined tear film characteristics of a contact lens wearer patient from the interference information is spatially registered to a particular area of the tear film 46 since the determined tear film characteristics of a contact lens wearer patient can be associated with such particular area, if desired.

The thickness of the lipid layer 50 ('$d_1$') is a function of the interference interactions between specularly reflected light rays 48, 58. The thickness of the lipid layer 50 ('$d_1$') is on the scale of the temporal (or longitudinal) coherence of the light source 30. Therefore, thin lipid layer films on the scale of one wavelength of visible light emitted by the light source 30 offer detectable colors from the interference of specularly reflected light when viewed by a camera or human eye. The colors may be detectable as a result of calculations performed on the interference signal and represented as a digital values including but not limited to a red-green-blue (RGB) value in the RGB color space. Quantification of the interference of the specularly reflected light can be used to measure LLT. Also, the change in thickness of the lipid layer over a period of time can be determined by evaluating the quantification of the interference of the specularly reflected light over a predetermined period of time. The thicknesses of an aqueous layer 60 ('$d_2$') can also be determined using the same principle. Some of the light rays 54 (not shown) passing through the lipid layer 50 can also pass through the lipid-to-aqueous layer transition 56 and enter into the aqueous layer 60 specularly reflecting from the aqueous-to-mucin/cornea layer transition 62. These specular reflections also undergo interference with the specularly reflected light rays 48, 58. The magnitude of the reflections from each interface depends on the refractive indices of the materials as well as the angle of incidence, according to Fresnel's equations, and so the depth of the modulation of the interference interactions is dependent on these parameters, thus so is the resulting color. Similarly, the change in thickness of the aqueous layer over a period of time can be determined by evaluating the quantification of the interference of the specularly reflected light over a predetermined period of time.

Turning back to FIGS. 4A and 4B, the illuminator 36 in this embodiment is a broad spectrum light source covering the visible region between about 400 nm to about 700 nm. The illuminator 36 contains an arced or curved housing 64 (see FIG. 4B) into which individual light emitters are mounted, subtending an arc of approximately 130 degrees from the optical axis of the eye 32 (see FIG. 4B). A curved surface may present better uniformity and be more efficient, as the geometry yields a smaller device to generating a given intensity of light. The total power radiated from the illuminator 36 should be kept to a minimum to prevent accelerated tear evaporation. Light entering the pupil can cause reflex tearing, squinting, and other visual discomforts, all of which affect tear film characteristic measurements accuracy involving a patient with contact lens wear.

In order to prevent alteration of the proprioceptive senses and reduce heating of the tear film 46, incident power and intensity on the eye 32 may be minimized and thus, the step of collecting and focusing the specularly reflected light may be carried out by the imaging device 40. The imaging device 40 may be a video camera, slit lamp microscope, or other observation apparatus mounted on the stand 38, as illustrated in FIGS. 4A and 4B. Detailed visualization of the image patterns of the tear film 46 involves collecting the specularly reflected light 66 and focusing the specularly reflected light at the lipid layer 50 such that the interference interactions of the specularly reflected light from the ocular tear film are observable.

Figure 6:
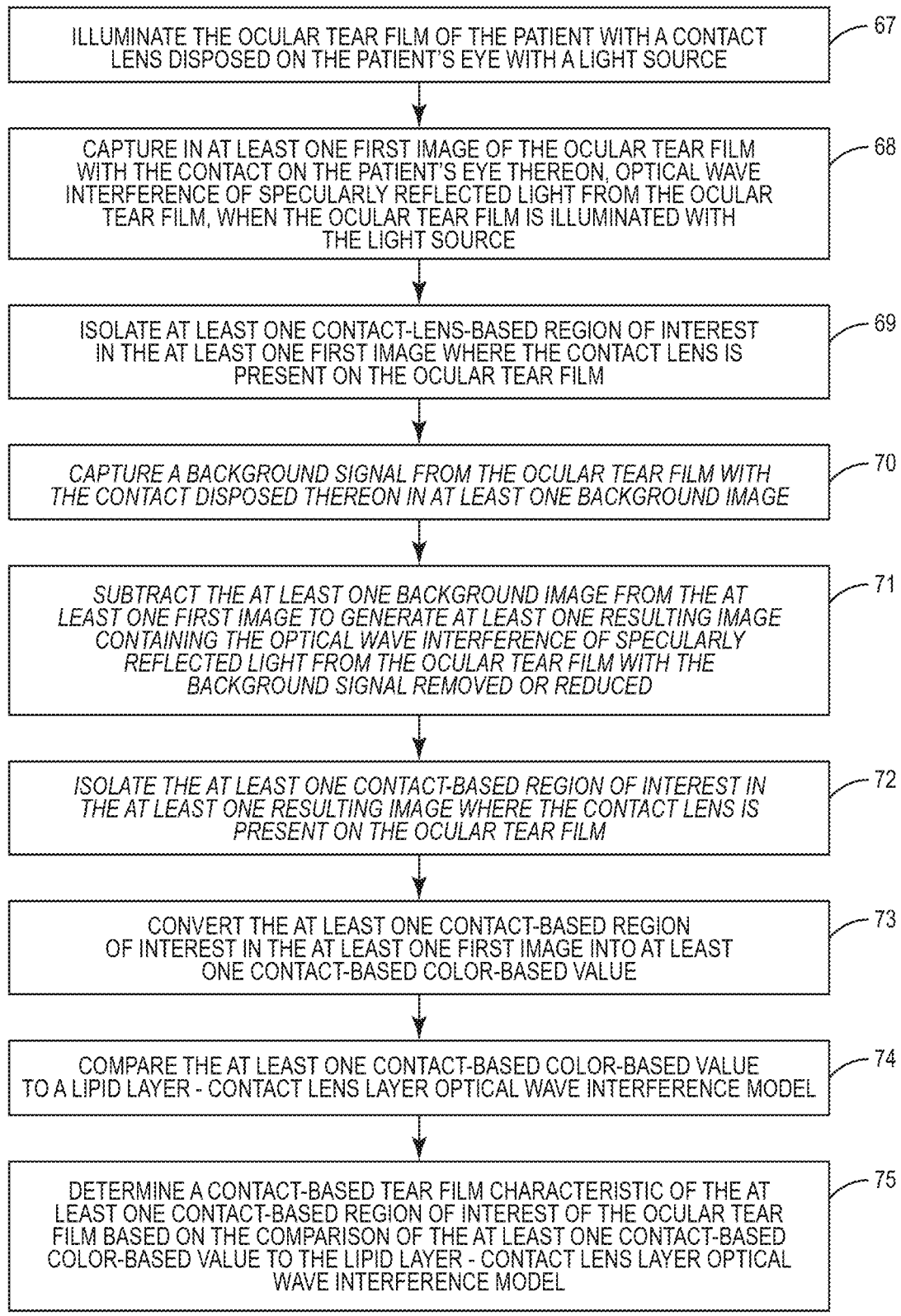
FIG. 6 is a flowchart of an exemplary process for determining tear film characteristics of a patient's ocular tear film based on analysis of imaged optical wave interference of specularly reflected light from a contact lens-based region of interest of the patient's tear film during contact lens wear, to determine the patient's intolerance to contact lens wear.

Against the backdrop of the OSI device 30 in FIGS. 4A and 4B, FIG. 6 illustrates a flowchart discussing how the OSI device 30 can be used to obtain interference interactions of specularly reflected light from the tear film 46, which can be used to determine tear film characteristics in contact lens wearers. As previously discussed above, an ocular tear film may be affected by contact lens wear. Contact lens wear can contribute to dry eye. A contact lens can disrupt the natural tear film and can reduce corneal sensitivity over time, which can cause a reduction in tear film production. For many of patients, evaporative dry eye disease is an underlying cause for their contact lens intolerance. Thus, in embodiments herein, imaging of the ocular tear film is performed during contact lens wear.

In this regard, as illustrated in FIG. 6, the illuminator 36 of the OSI device 30 is employed to illuminate the ocular tear film of a patient with a contact lens disposed on a patient's eye. The exemplary process will be described followed by a more detailed discussion of the steps of the process. The process in this example starts by adjusting the patient 32 with regard to an illuminator 36 and an imaging device 40 in the OSI device 30 in FIGS. 4A and 4B. The illuminator 36 is controlled to illuminate the patient's 34 tear film 46. The imaging device 40 is controlled to be focused on the anterior surface 52 of the lipid layer 50 such that the interference interactions of specularly reflected light from the tear film 46 are collected and are observable. Thereafter, the patient's 34 tear film 46 is illuminated by the illuminator 36 (block 67 in FIG. 6). The patient may be instructed to blink hard and/or hold a blink for a period of time, for example 15 seconds, prior to illumination and imaging, described below.

The imaging device 40 of the OSI device 30 is then controlled and focused on the lipid layer 50 to capture specularly reflected light in a first image from the ocular tear film with a contact lens disposed on the patient's eye as a result of illuminating the tear film with the illuminator 36 in a first image (block 68, FIG. 6). The ocular tear film is disposed on top of the contact lens. The first image contains optical wave interference of specularly reflected light from the ocular tear film when illuminated by the illuminator 36. An example of such a first image by the imaging device 40 is provided in FIG. 7. As illustrated therein, a first image 79 of a patient's eye 80 that has a contact lens 84 disposed on the patient's eye 80 is shown that has been illuminated with the illuminator 36. The illuminator 36 and the imaging device 40 may be controlled to illuminate an area or region of interest 81 on a tear film 82 that does not include a pupil 83 of the eye 80 so as to reduce reflex tearing. Reflex tearing will temporarily lead to thicker aqueous and lipid layers, thus temporarily altering the interference signals of specularly reflected light from the tear film 82.

Figure 7:
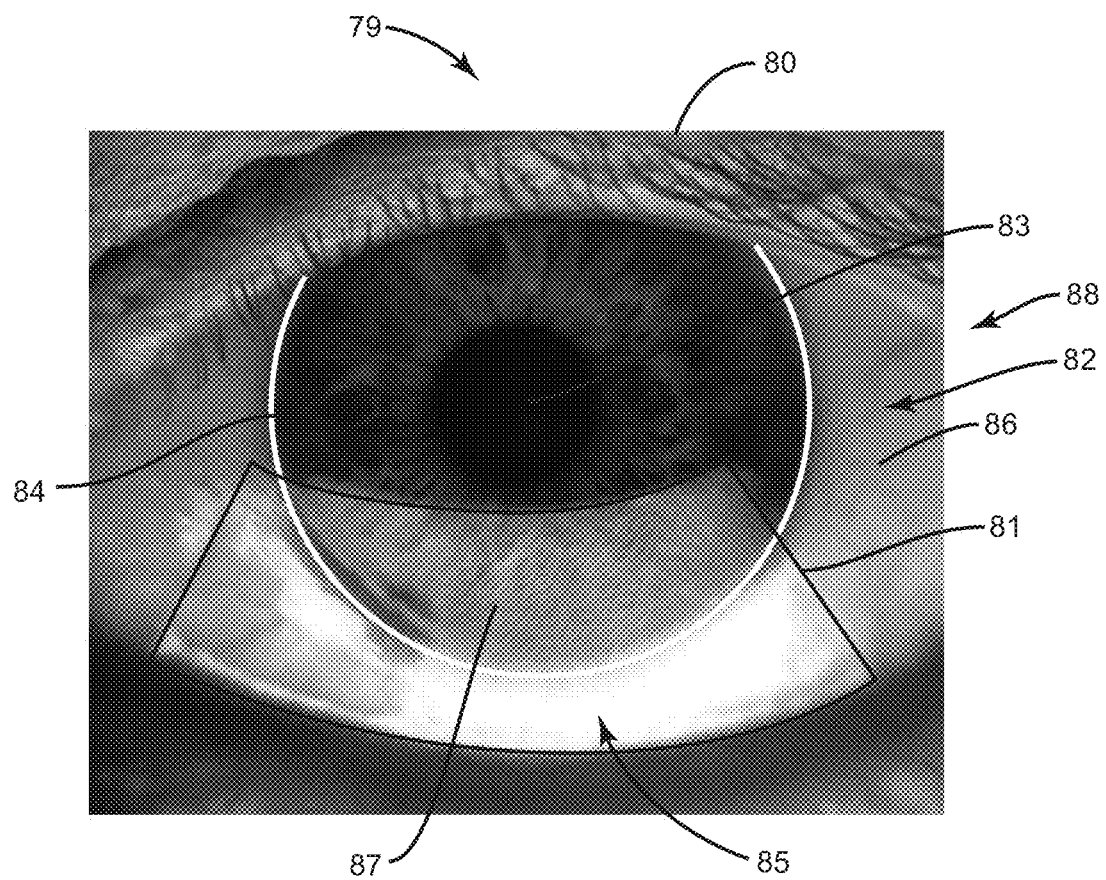
FIG. 7 illustrates a first image focused on a lipid layer of a patient's tear film while the patient is wearing a contact lens, and capturing interference interactions of specularly reflected light from an area or region of interest of the tear film.

As shown in FIG. 7, when the imaging device 40 is focused on an anterior surface 86 of the lipid layer 88 of the tear film 82 disposed on top of the contact lens 84, interference interactions 85 of the interference signal of the specularly reflected light from the tear film 82 as a result of illumination by the illuminator 36 are captured in the area or region of interest 81 in the first image 79. The region of interest 81 has a contact lens-based region 87 where the contact lens 84 was present in the first image 79. The interference interactions 85 appear to a human observer as colored patterns as a result of the wavelengths present in the interference of the specularly reflected light from the tear film 82. As will be discussed in more detail below, it may be desired to isolate the contact lens-based region 87 in the first image 79 to analyze the specularly reflected light from the tear film 82 as a result of illumination by the illuminator 36 in the contact lens-based region 87 and in the region of interest 81 where the contact lens 84 is not present in the first image 79 (block 72 in FIG. 6). In this manner, effect of tear film characteristics due to the patient's wear of the contact lens 84 may be determined and/or observed.

With continuing reference to FIG. 7, a background signal is also captured in the first image 79. The background signal is added to the specularly reflected light in the area or region of interest 81 and included outside the area or region of interest 81 as well. Background signal is light that is not specularly reflected from the tear film 82 and thus contains no interference information. Background signal can include stray and ambient light entering into the imaging device 40, scattered light from the patient's 34 face, eyelids, and/or eye 80 structures outside and beneath the tear film 82 as a result of stray light, ambient light and diffuse illumination by the illuminator 36, and images of structures beneath the tear film 82. For example, the first image 79 includes the iris of the eye 80 beneath the tear film 82. Background signal adds a bias (i.e., offset) error to the captured interference of specularly reflected light from the tear film 82 thereby reducing its signal strength and contrast. Further, if the background signal has a color hue different from the light of the light source, a color shift can also occur to the interference of specularly reflected light from the tear film 82 in the first image 79. The imaging device 40 produces a first output signal that represents the light rays captured in the first image 79. Because the first image 79 contains light rays from specularly reflected light as well as the background signal, the first output signal produced by the imaging device 40 from the first image 79 will contain an interference signal representing the captured interference of the specularly reflected light from the tear film 82 with a bias (i.e., offset) error caused by the background signal. As a result, the first output signal analyzed to determine tear film characteristic determinations and/or measurements involving a patient with contact lens wear may contain error as a result of the background signal bias (i.e., offset) error.

Figure 8:
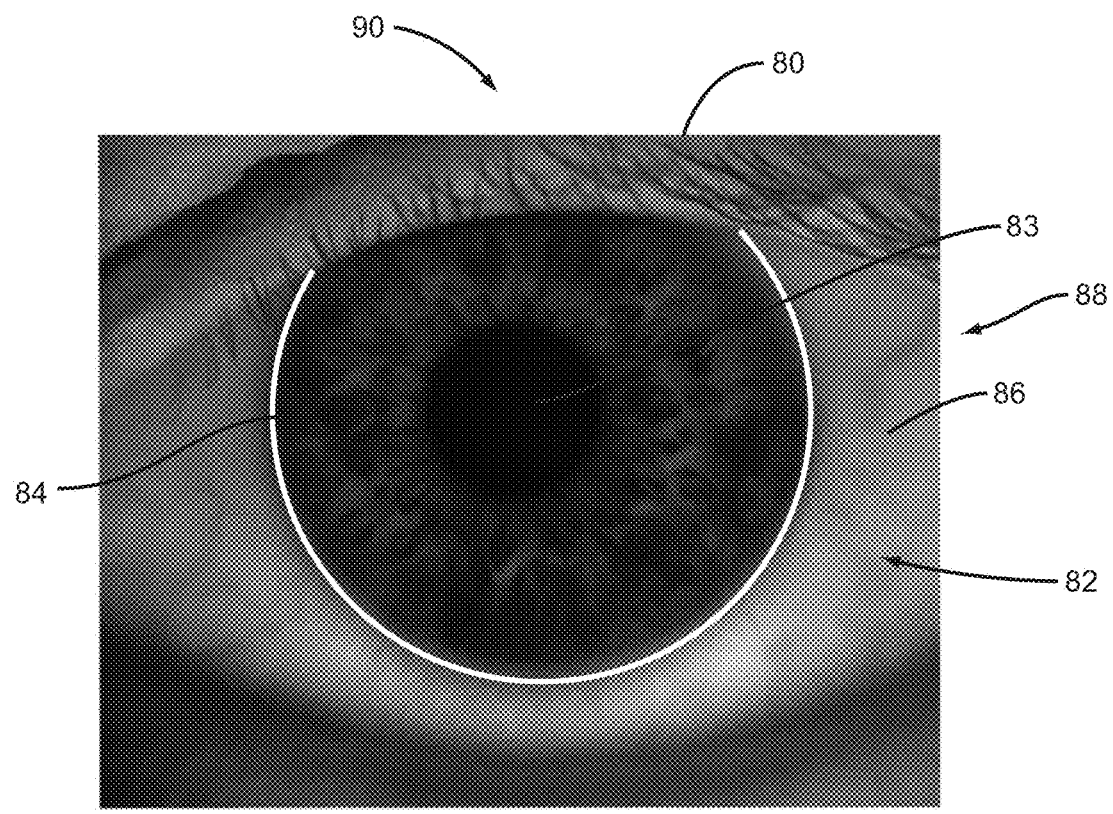
FIG. 8 illustrates a second image focused on the lipid layer of the tear film in FIG. 7 and capturing background signal when not illuminated by the light source.
Figure 9:
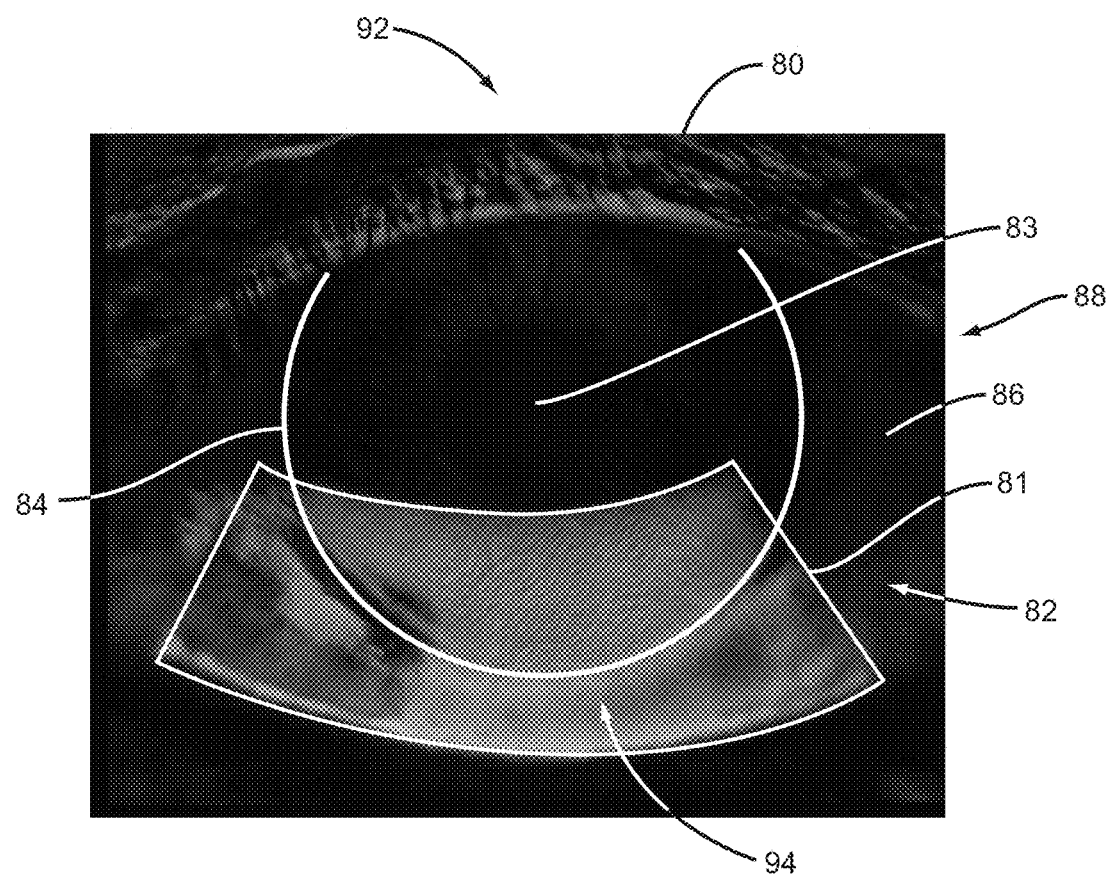
FIG. 9 illustrates an image of the tear film when background signal captured in the second image of FIG. 8 is subtracted from the first image of FIG. 7.

Thus, in this embodiment, the first output signal generated by the imaging device 40 as a result of the first image 79 is processed to subtract or substantially subtract the background signal from the interference signal to reduce error before being analyzed to determine tear film characteristic determinations and/or measurements involving a patient with contact lens wear. This is also referred to as "background subtraction." Background subtraction is the process of removing unwanted reflections from images. In this regard, the imaging device 40 is optionally controlled to capture a second, background image 90 ("second image 90") of the tear film 82 when not illuminated by the illuminator 36, as illustrated by example in FIG. 8 (block 70 in FIG. 6). The second image 90 can be captured using the same imaging device 40 settings and focal point as when capturing the first image 79 so that the first image 79 and second image 90 forms corresponding image pairs captured within a short time of each other. The imaging device 40 produces a second output signal containing background signal present in the first image 79. To eliminate or reduce this background signal from the first output signal, the second output signal is subtracted from the first output signal to produce a resulting signal (block 71 in FIG. 6). The image representing the resulting signal in this example is illustrated in FIG. 9 as resulting image 92. Thus, in this example, background subtraction involves two images 79, 90 to provide a frame pair where the two images 79, 90 are subtracted from each other, whereby specular reflection from the tear film 82 is retained, and while diffuse reflections from the iris and other areas are removed in whole or part.

As illustrated in FIG. 9, the resulting image 92 contains an image of the isolated interference 94 of the specularly reflected light from the tear film 82 with the background signal eliminated or reduced (block 71 in FIG. 6). In this manner, the resulting signal (representing the resulting image 92 in FIG. 9) includes an interference signal having signal improved purity and contrast in the area or region of interest 81 on the tear film 82. As will be discussed later in this application, the resulting signal provides for accurate analysis of interference interactions from the interference signal of specular reflections from the tear film 82 to in turn determine more tear film characteristics indicative of contact lens wear intolerance. Any method or device to obtain the first and second images of the tear film 82 and perform the subtraction of background signal in the second image 90 from the first image 79 may be employed. Other specific examples are discussed throughout the remainder of this application.

An optional registration function may be performed between the first image(s) 79 and the second image(s) 90 before subtraction is performed to ensure that an area or point in the second image(s) 90 to be subtracted from the first image(s) 79 is for an equivalent or corresponding area or point on the first image(s) 79. For example, a set of homologous points may be taken from the first and second images 79, 90 to calculate a rigid transformation matrix between the two images. The transformation matrix allows one point on one image (e.g., x1, y1) to be transformed to an equivalent two-dimensional (2D) image on the other image (e.g., x2, y2). For example, the Matlab® function "cp2tform" can be employed in this regard. Once the transformation matrix is determined, the transformation matrix can be applied to every point in the first and second images, and then each re-interpolated at the original points. For example, the Matlab® function "imtransform" can be employed in this regard. This allows a point from the second image 90 (e.g., x2, y2) to be subtracted from the correct, equivalent point (e.g., x1, y1) on the first image(s) 79, in the event there is any movement in orientation or the patient's eye between the capture of the first and second images 79, 90. The first and second images 79, 90 should be captured close in time.

Note that while this example discusses a first image and a second (i.e., background) image captured by the imaging device 40 and a resulting first output signal and second output signal, the first image and the second image may comprise a plurality of images taken in a time-sequenced fashion. If the imaging device 40 is a video camera, the first and second images may contain a number of sequentially-timed frames governed by the frame rate of the imaging device 40. The imaging device 40 produces a series of first output signals and second output signals. If more than one image is captured, the subtraction performed in a first image should ideally be from a second image taken immediately after the first image so that the same or substantially the same lighting conditions exist between the images so the background signal in the second image is present in the first image. The subtraction of the second output signal from the first output signal can be performed in real time. Alternatively, the first and second output signals can be recorded and processed at a later time. The illuminator 36 may be controlled to oscillate off and on quickly so that first and second images can be taken and the second output signal subtraction from the first output signal be performed in less than one second. For example, if the illuminator 36 oscillates between on and off at 30 Hz, the imaging device 40 can be synchronized to capture images of the tear film 46 at 60 frames per second (fps). In this regard, thirty (30) first images and thirty (30) second images can be obtained in one second, with each pair of first and second images taken sequentially.

Figure 10:
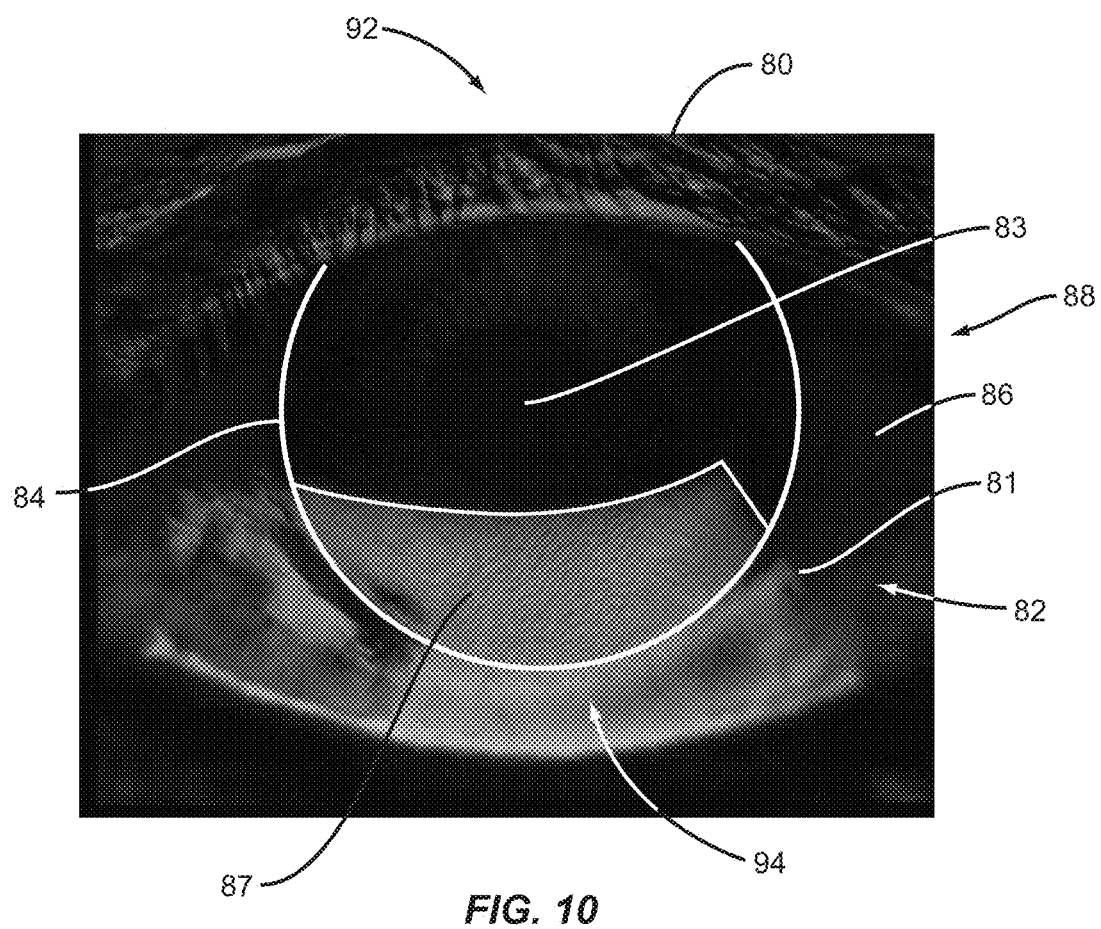
FIG. 10 illustrates the image of the tear film in FIG. 9 with a contact lens-based region of interest in the image isolated to determine and analyze one or more tear film characteristics of the contact lens-based region of interest of the tear film and/or analyze one or more tear film characteristics of a non-contact lens-based region of interest of the tear film to determine the effect of contact lens wear on the patient's tear film.

After the interference of the specularly reflected light is captured and a resulting signal containing the interference signal is produced and processed, the contact lens-based region of interest 87 is isolated from the resulting image 92 (block 72 in FIG. 6) as shown in FIG. 10. The interference signal or representations thereof in the contact lens-based regions of interest 87 can be converted to at least one color-based value (block 73 in FIG. 6) and compared against a lipid layer—contact lens layer interference model that includes a contact lens index of refraction as part of the aqueous layer in the model (block 74 in FIG. 6) to determine one or more tear film characteristics (block 75 in FIG. 6), such as measuring tear film thickness, as will be discussed in more detail below. The interference signal can be processed and converted by the imaging device into digital red-green-blue (RGB) component values which can be compared to RGB component values in a tear film interference model to determine tear film characteristics of the contact lens-based regions of interest 87.

The lipid layer—contact lens layer interference model is based on modeling the lipid layer of the tear film in various LLTs with the presence of a contact lens and representing resulting interference interactions in the interference signal of specularly reflected light from the model when illuminated by the light source. The lipid layer—contact lens layer interference model can be a theoretical tear film interference model where the particular light source, the particular imaging device, and the tear film layers are modeled mathematically, and the resulting interference signals for the various LLTs recorded when the modeled light source illuminates the modeled tear film layers recorded using the modeled imaging device. The settings for the mathematically modeled light source and imaging device should be replicated in the illuminator 36 and imaging device 40 used in the OSI device 30. Alternatively, as will be discussed in more detail below, the lipid layer—contact lens layer interference model can be based on a phantom tear film model, comprised of physical phantom tear film layers wherein the actual light source is used to illuminate the phantom tear film model and interference interactions in the interference signal representing interference of specularly reflected light are empirically observed and recorded using the actual imaging device 40.

The aqueous layer may be modeled in the lipid layer—contact lens layer interference model to be of an infinite, minimum, or varying thickness based on the index of refraction of the contact lens. If the aqueous layer is modeled to be of an infinite thickness, the lipid layer—contact lens layer interference model assumes no specular reflections occur from the aqueous (i.e. contact lens)-to-mucin layer transition 62 (see FIG. 5). If the contact lens is modeled to be of a certain minimum thickness (e.g., ≥2 μm), the specular reflection from the aqueous (contact lens)-to-mucin layer transition 62 may be considered negligible on the effect of the convolved RGB signals produced by the interference signal. In either case, the lipid layer—contact lens layer interference model will only assume and include specular reflections from the lipid-to-aqueous layer transition 56. Thus, these lipid layer—contact lens layer interference model embodiments allow the determining of tear film characteristics of the contact lens-based region of interest 87 regardless of ALT. The interference interactions in the interference signal are compared to the interference interactions in the lipid layer—contact lens layer interference model to determine tear film characteristics of the contact lens-based region of interest 87.

Alternatively, if the contact lens representing the aqueous layer 60 is modeled to be of varying thicknesses, the lipid layer—contact lens layer interference model additionally includes specular reflections from the aqueous (contact lens)-to-mucin layer transition 62 in the interference interactions. As a result, the lipid layer—contact lens layer interference model will include two-dimensions of data comprised of interference interactions corresponding to various LLT and ALT combinations. The interference interactions from the interference signal can be compared to interference interactions in the lipid layer—contact lens layer interference model to measure both LLT and ALT. More information regarding specific tear film interference models will be described later in this application.

In the above described embodiment in FIGS. 6-9, the second image 90 of the tear film 82 containing background signal is captured when not illuminated by the illuminator 36. Only ambient light illuminates the tear film 82 and eye 80 structures beneath. Thus, the second image 90 and the resulting second output signal produced by the imaging device 40 from the second image 90 does not include background signal resulting from scattered light from the patient's 34 face and eye structures as a result of diffuse illumination by the illuminator 36. Only scattered light resulting from ambient light is included in the second image 90. However, scattered light resulting from diffuse illumination by the illuminator 36 is included in background signal in the first image 79 containing the interference interactions of specularly reflected light from the tear film 82. Further, because the first image 79 is captured when the illuminator 36 is illuminating the tear film 82, the intensity of the eye structures beneath the tear film 82 captured in the first image 79, including the iris, are brighter than captured in the second image 90.

Thus, in other embodiments described herein, the imaging device 40 is controlled to capture a second image 90 of the tear film 82 when obliquely illuminated by the illuminator 36. As a result, the captured second image 90 additionally includes background signal from scattered light as a result of diffuse illumination by the illuminator 36 as well as a higher intensity signal of the directly illuminated eye structures beneath the tear film 82. Thus, when the second output signal is subtracted from the first output signal, the higher intensity eye structure background and the component of background signal representing scattered light as a result of diffuse illumination by the illuminator 36, as well as ambient and stray light, are subtracted or substantially subtracted from the resulting signal thereby further increasing the interference signal purity and contrast in the resulting signal. The resulting signal can then be processed and analyzed to determine tear film characteristics of a patient involving contact lens wear, as will be described in detail later in this application.

Figure 11:
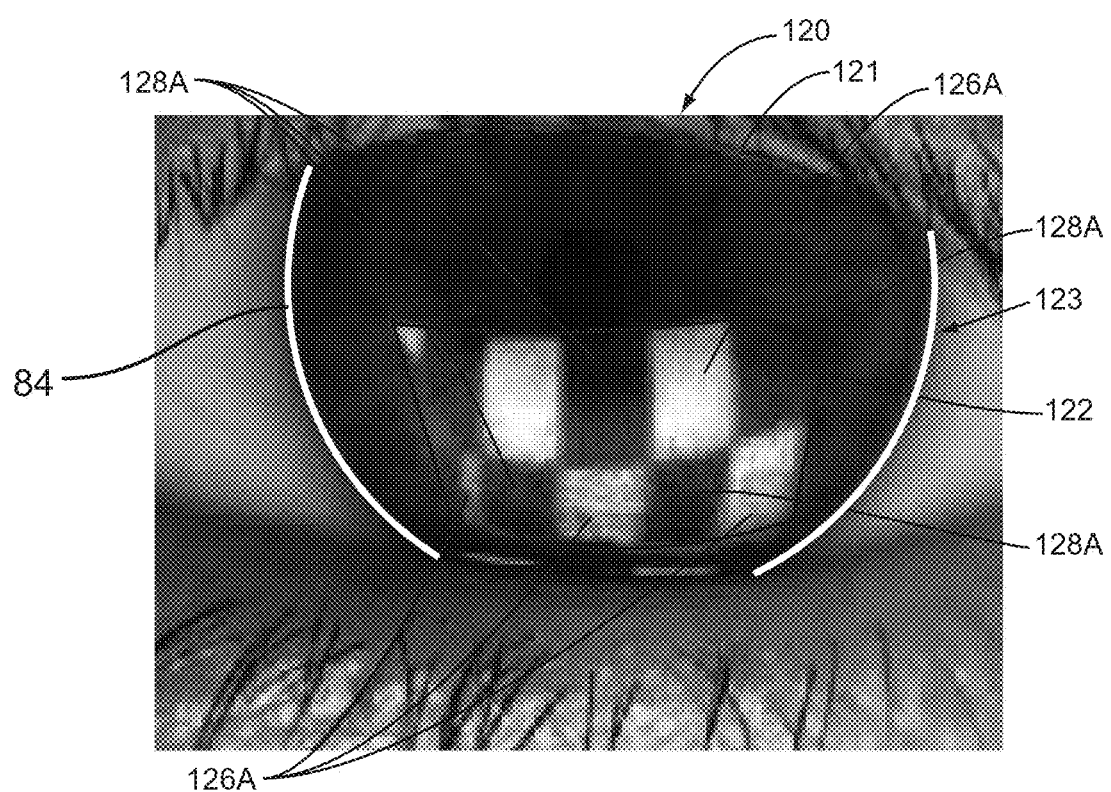
FIG. 11 illustrates a first image focused on the lipid layer of the tear film capturing interference interactions of specularly reflected light and background signal from tiled portions in an area or region of interest of the tear film during contact lens wear.
Figure 12:
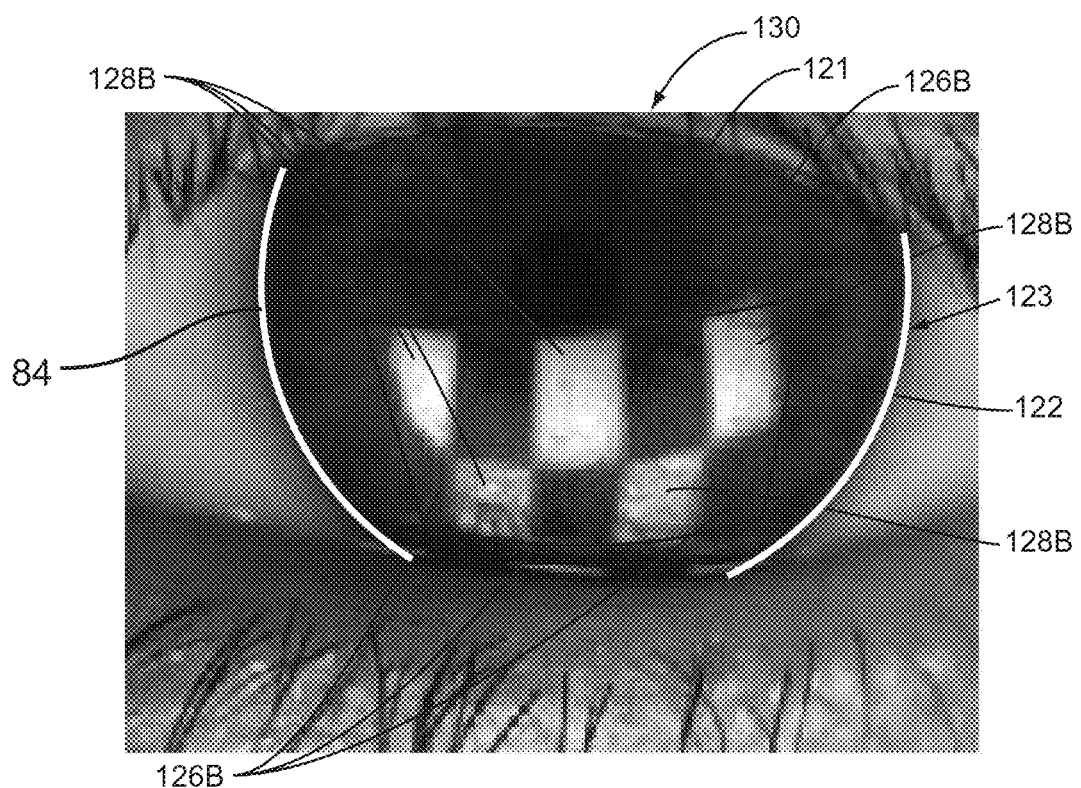
FIG. 12 illustrates a second image focused on the lipid layer of the tear film in FIG. 11 capturing background signal and interference interactions of specularly reflected light from the tiled portions in the area or region of interest in FIG. 11, respectively during contact lens wear.
Figure 13:
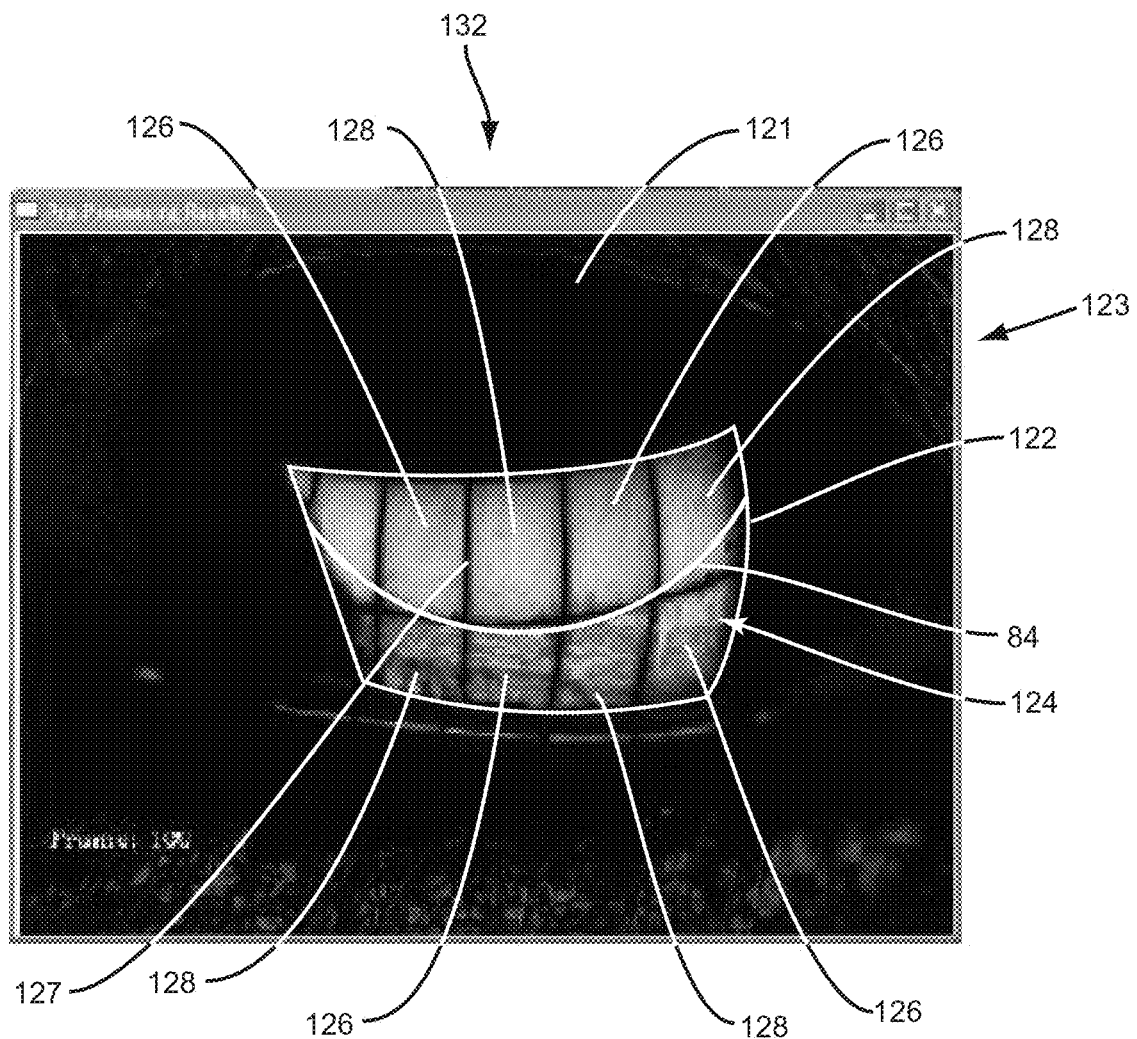
FIG. 13 illustrates an image when the background signal captured in diffusely illuminated tiled portions in the first and second images of FIGS. 11 and 12 are subtracted or substantially subtracted from the specularly reflected light in corresponding tiled portions in the first and second images of FIGS. 11 and 12.

In this regard, FIGS. 11-13 illustrate an embodiment for illuminating and capturing interference of specularly reflected light from the tear film. In this embodiment, the second image is captured when the tear film is obliquely illuminated by the illuminator 36 using illumination that possesses the same or nearly the same average geometry and illuminance level as used to produce specularly reflected light from a tear film. In this manner, the background signal captured in the second image contains the equivalent background signal present in the first image including scattered light from the tear film and patient's eye as a result of diffuse illumination by the illuminator 36. The second image also includes a representative signal of eye structure beneath the tear film because of the equivalent lighting when the illuminator 36 is activated when capturing the second image. In this embodiment, a "tiled" or "tiling" illumination of the tear film is provided. Tiling allows a light source to illuminate a sub-area(s) of interest on the tear film to obtain specularly reflected light while at the same time diffusely illuminating adjacent sub-area(s) of interest of the tear film to obtain scattered light as a result of diffuse illumination by the illuminator 36. In this manner, the subtracted background signal includes scattered light as a result of diffuse illumination by the illuminator 36 to allow further reduction of offset bias (i.e., offset) error and to thereby increase interference signal purity and contrast.

In this regard, the illuminator 36 is controlled to illuminate the patient's 34 tear film. The imaging device 40 is located appropriately and is controlled to be focused on the lipid layer such that the interference interactions of specularly reflected light from the tear film are observable when the tear film is illuminated. Thereafter, the lighting pattern of the illuminator 36 is controlled in a first "tiling" mode to produce specularly reflected light from a first area(s) of interest of the tear film while diffusely illuminating an adjacent, second area(s) of interest of the tear film. As will be discussed in more detail later in this application, the illuminator 36 may be controlled to turn on only certain lighting components in the illuminator 36 to control the lighting pattern. As will be further discussed, the lighting pattern can also be directed to the meibomian glands directly, the transillumination of the meibomian glands, and the characteristics of the patient's blinking or partial blinking.

An example of a first image 120 captured of a patient's eye 121 and tear film 123 by the imaging device 40 when the illuminator 36 produces a light pattern in the first mode is illustrated by example in FIG. 11. In this example, the illuminator 36 is controlled to provide a first tiled illumination pattern in an area or region of interest 122 on the tear film 123. While illumination of the tear film 123 occurs in the first mode, the imaging device 40 captures the first image 120 of the patient's eye 121 and the tear film 123. As illustrated in FIG. 11, the first image 120 of the patient's eye 121 has been illuminated so that specularly reflected light is produced in first portions 126A in the area or region of interest 122 of the tear film 123. The interference signal(s) from the first portions 126A include interference from specularly reflected light along with additive background signal, which includes scattered light signal as a result of diffuse illumination from the illuminator 36. Again, the illuminator 36 and the imaging device 40 may be controlled to illuminate the tear film 123 that does not include the pupil of the eye 121 so as to reduce reflex tearing. The illuminator 36 may be flashed in to produce specularly reflected light from the first portions 126A, whereby the imaging device 40 is synchronized with the flashing of the illuminator 36 in to capture the first image 120 of the patient's eye 121 and the tear film 123.

Also during the first mode, the illuminator 36 light pattern obliquely illuminates second, adjacent portions 128A to the first portions 126A in the area or region of interest 122, as shown in the first image 120 in FIG. 11. The second portions 128A include comparable background offset present in the first portion(s) 126A, which includes scattered light signal as a result of diffuse illumination from the illuminator 36 since the illuminator 36 is turned on when the first image 120 is captured by the imaging device 40. Further, the eye 121 structures beneath the tear film 123 are captured in the second portions 128A due to the diffuse illumination by the illuminator 36. This is opposed to the second image 90 of FIG. 9, where diffuse illumination by the illuminator 36 is not provided to the tear film when the second image 90 is obtained. Thus, in this embodiment, the area or region of interest 122 of the tear film 123 is broken into two portions at the same time: first portions 126A producing specularly reflected light combined with background signal, and second portions 128A diffusedly illuminated by the illuminator 36 and containing background signal, which includes scattered light from the illuminator 36. The imaging device 40 produces a first output signal that contains a representation of the first portions 126A and the second portions 128A.

Next, the illuminator 36 is controlled in a second mode to reverse the lighting pattern from the first mode when illuminating the tear film 123. A second image 130 is captured of the tear film 123 is captured in the second mode of illumination, as illustrated by example in FIG. 12. As shown in the second image 130 in FIG. 12, the second portions 128A in the first image 120 of FIG. 11 are now second portions 128B in the second image 130 in FIG. 12 containing specularly reflected light from the tear film 123 with additive background signal. The first portions 126A in the first image 120 of FIG. 11 are now first portions 126B in the second image 130 in FIG. 12 containing background signal without specularly reflected light. Again, the background signal in the first portions 126B includes scattered light signal as a result of diffuse illumination by the illuminator 36. The imaging device 40 produces a second output signal of the second image 130 in FIG. 12. The illuminator 36 may also be flashed in block 106 to produce specularly reflected light from the second portions 128B, whereby the imaging device 40 is synchronized with the flashing of the illuminator 36 to capture the second image 130 of the patient's eye 121 and the tear film 123.

The first and second output signals can then be combined to produce a resulting signal comprised of the interference signal of the specularly reflected light from the tear film 123 with background signal subtracted or substantially removed from the interference signal. A resulting image is produced as a result of having interference information from the specularly reflected light from the area or region of interest 122 of the tear film 123 with background signal eliminated or reduced, including background signal resulting from scattered light from diffuse illumination by the illuminator 36. An example of a resulting image 132 in this regard is illustrated in FIG. 13. The resulting image 132 represents the first output signal represented by the first image 120 in FIG. 11 combined with the second output signal represented by the second image 130 in FIG. 12. As illustrated in FIG. 13, interference signals of specularly reflected light from the tear film 123 are provided for both the first and second portions 126, 128 in the area or region of interest 122. The background signal has been eliminated or reduced. As can be seen in FIG. 13, the signal purity and contrast of the interference signal representing the specularly reflected light from the tear film 123 from first and second portions 126, 128 appears more vivid and higher in contrast than the interference interaction 94 in FIG. 9, for example.

In the discussion of the example first and second images 120, 130 in FIGS. 11 and 12 above, each first portion 126 can be thought of as a first image, and each second portion 128 can be thought of as a second image. Thus, when the first and second portions 126A, 128B are combined with corresponding first and second portions 126B, 128A, this is akin to subtracting second portions 126B, 128A from the first portions 126A, 128B, respectively.

In the example of FIGS. 11-13, the first image and second images 120, 130 contain a plurality of portions or tiles. The number of tiles depends on the resolution of lighting interactions provided for and selected for the illuminator 36 to produce the first and second modes of illumination to the tear film 123. The illumination modes can go from one extreme of one tile to any number of tiles desired. Each tile can be the size of one pixel in the imaging device 40 or areas covering more than one pixel depending on the capability of the illuminator 36 and the imaging device 40. The number of tiles can affect accuracy of the interference signals representing the specularly reflected light from the tear film. Providing too few tiles in a tile pattern can limit the representative accuracy of the average illumination geometry that produces the scattered light signal captured by the imaging device 40 in the portions 128A and 126B for precise subtraction from portions 128B and 126A respectively.

Note that while this example in FIGS. 11-13 discusses a first image and a second image captured by the imaging device 40 and a resulting first output signal and second output signal, the first image and the second image may comprise a plurality of images taken in a time-sequenced fashion. If the imaging device 40 is a video camera, the first and second images may contain a number of sequentially-timed frames governed by the frame rate of the imaging device 40. The imaging device 40 produces a series of first output signals and second output signals. If more than one image is captured, the subtraction performed in a first image should ideally be from a second image taken immediately after the first image so that the same or substantially the same lighting conditions exist between the images so the background signal in the second image is present in the first image, and more importantly, so that movement of the eye and especially of the tear-film dynamic is minimal between subtracted frames. The subtraction of the second output signal from the first output signal can be performed in real time. Alternatively, the first and second output signals can be recorded and processed at a later time.

The first and second output signals can then be combined to produce a resulting signal comprised of the interference signal of the specularly reflected light from the tear film 142 for the entire area or region of interest 146 with background signal subtracted or substantially removed from the interference signal. A resulting image (not shown) similar to FIG. 12 can be produced as a result of having interference information from the specularly reflected light from the area or region of interest 146 from the tear film 142 with background signal eliminated or reduced, including background signal resulting from scattered light from diffuse illumination by the illuminator 36.

The resulting image can then be processed and analyzed to determine tear film characteristics of a contact lens wearing patient. The processes described above in FIG. 6 of isolating a contact lens-based region of interest 127 in the region of interest 122 to determine tear film characteristics therein can be employed.

Exemplary OSI Device

The above discussed illustrations provide examples of illuminating and imaging a patient's tear film involving contact lens wear. These principles are described in more detail with respect to a specific example of an OSI device 170 illustrated in FIG. 14 and described below throughout the remainder of this application. The OSI device 170 can illuminate a patient's tear film, capture interference information from the patient's tear film, and process and analyze the interference information to measure tear film characteristics involving contact lens wear by a patient, including but not limited to TFLT. Tear film characteristics may include size, shape, movement or speed, break up or disappearance of tear film, spread or coverage within an area of interest, and consistency of TFLT within an area of interest. Further, the OSI device 170 includes a number of optional pre-processing features that may be employed to process the interference signal in the resulting signal to enhance tear film characteristic determinations and/or measurements. The OSI device 170 may include a display and user interface to allow a physician or technician to control the OSI device 170 to image a patient's eye and tear film and determine and/or measure tear film characteristic involving contact lens wear by a patient.

Illumination and Imaging

Figure 14:
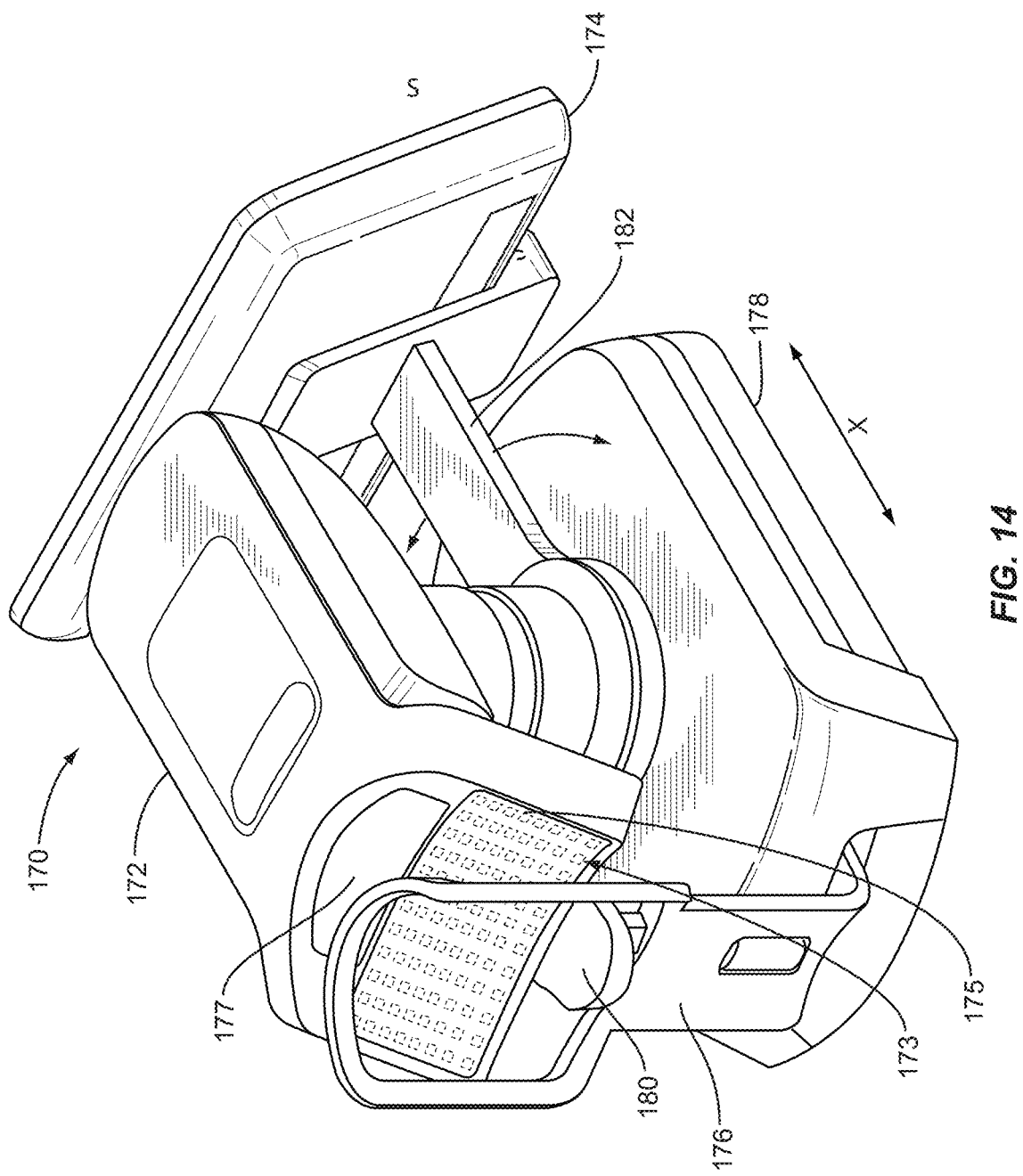
FIG. 14 is a perspective view of an exemplary ocular surface interferometry (OSI) device for illuminating and imaging a patient's tear film involving contact lens wear, displaying images, analyzing tear film characteristics of the tear film, and generating results from the analysis of the patient's tear film.

In this regard, FIG. 14 illustrates a perspective view of the OSI device 170. The OSI device 170 is designed to facilitate imaging of the patient's ocular tear film and processing and analyzing the images to determine characteristics regarding a patient's tear film. The OSI device 170 includes an imaging device and light source in this regard, as will be described in more detail below. As illustrated in FIG. 14, the OSI device 170 is comprised generally of a housing 172, a display monitor ("display") 174, and a patient head support 176. The housing 172 may be designed for table top placement. The housing 172 rests on a base 178 in a fixed relationship. As will be discussed in more detail below, the housing 172 houses an imaging device and other electronics, hardware, and software to allow a clinician to image a patient's ocular tear film. A light source 173 (also referred to herein as "illuminator 173") is also provided in the housing 172 and provided behind a diffusing translucent window 175. The translucent window 175 may be a flexible, white, translucent acrylic plastic sheet.

To image a patient's ocular tear film, the patient places his or her head in the patient head support 176 and rests his or her chin on a chin rest 180. The chin rest 180 can be adjusted to align the patient's eye and tear film with the imaging device inside the housing 172, as will be discussed in more detail below. The chin rest 180 may be designed to support up to two (2) pounds of weight, but such is not a limiting factor. A transparent window 177 allows the imaging device inside the housing 172 to have a clear line of sight to a patient's eye and tear film when the patient's head is placed in the patient head support 176. The OSI device 170 is designed to image one eye at a time, but can be configured to image both eyes of a patient, if desired.

In general, the display 174 provides input and output from the OSI device 170. For example, a user interface can be provided on the display 174 for the clinician to operate the OSI device 170 and to interact with a control system provided in the housing 172 that controls the operation of the OSI device 170, including an imaging device, an imaging device positioning system, a light source, other supporting hardware and software, and other components. For example, the user interface can allow control of imaging positioning, focus of the imaging device, and other settings of the imaging device for capturing images of a patient's ocular tear film. The control system may include a general purpose microprocessor or computer with memory for storage of data, including images of the patient's eye and tear film. The microprocessor should be selected to provide sufficient processing speed to process images of the patient's tear film and generate output characteristic information about the tear film (e.g., one minute per twenty second image acquisition). The control system may control synchronization of activation of the light source and the imaging device to capture images of areas of interest on the patient's ocular tear film when properly illuminated. Various input and output ports and other devices can be provided, including but not limited to a joystick for control of the imaging device, USB ports, wired and wireless communication including Ethernet communication, a keyboard, a mouse, speaker(s), etc. A power supply is provided inside the housing 172 to provide power to the components therein requiring power. A cooling system, such as a fan, may also be provided to cool the OSI device 170 from heat generating components therein.

The display 174 is driven by the control system to provide tear film characteristics regarding a patient's imaged tear film involving contact lens wear, including but not limited to TFLT. The display 174 also provides a graphical user interface (GUI) to allow a clinician or other user to control the OSI device 170. To allow for human diagnosis of the patient's tear film, images of the patient's ocular tear film taken by the imaging device in the housing 172 can also be displayed on the display 174 for review by a clinician, as will be illustrated and described in more detail below. The images displayed on the display 174 may be real-time images being taken by the imaging device, or may be previously recorded images stored in memory. To allow for different orientations of the OSI device 170 to provide a universal configuration for manufacturing, the display 174 can be rotated about the base 178. The display 174 is attached to a monitor arm 182 that is rotatable about the base 178, as illustrated. The display 174 can be placed opposite of the patient head support 176, as illustrated in FIG. 14, if the clinician desires to sit directly across from the patient. Alternatively, display 174 can be rotated either left or right about the X-axis to be placed adjacent to the patient head support 176. The display 174 may be a touch screen monitor to allow a clinician or other user to provide input and control to the control system inside the housing 172 directly via touch of the display 174 for control of the OSI device 170. The display 174 illustrated in FIG. 14 is a fifteen inch (15") flat panel liquid crystal display (LCD). However, the display 174 may be provided of any type or size, including but not limited to a cathode ray tube (CRT), plasma, LED, OLED, projection system, etc.

Figure 15:
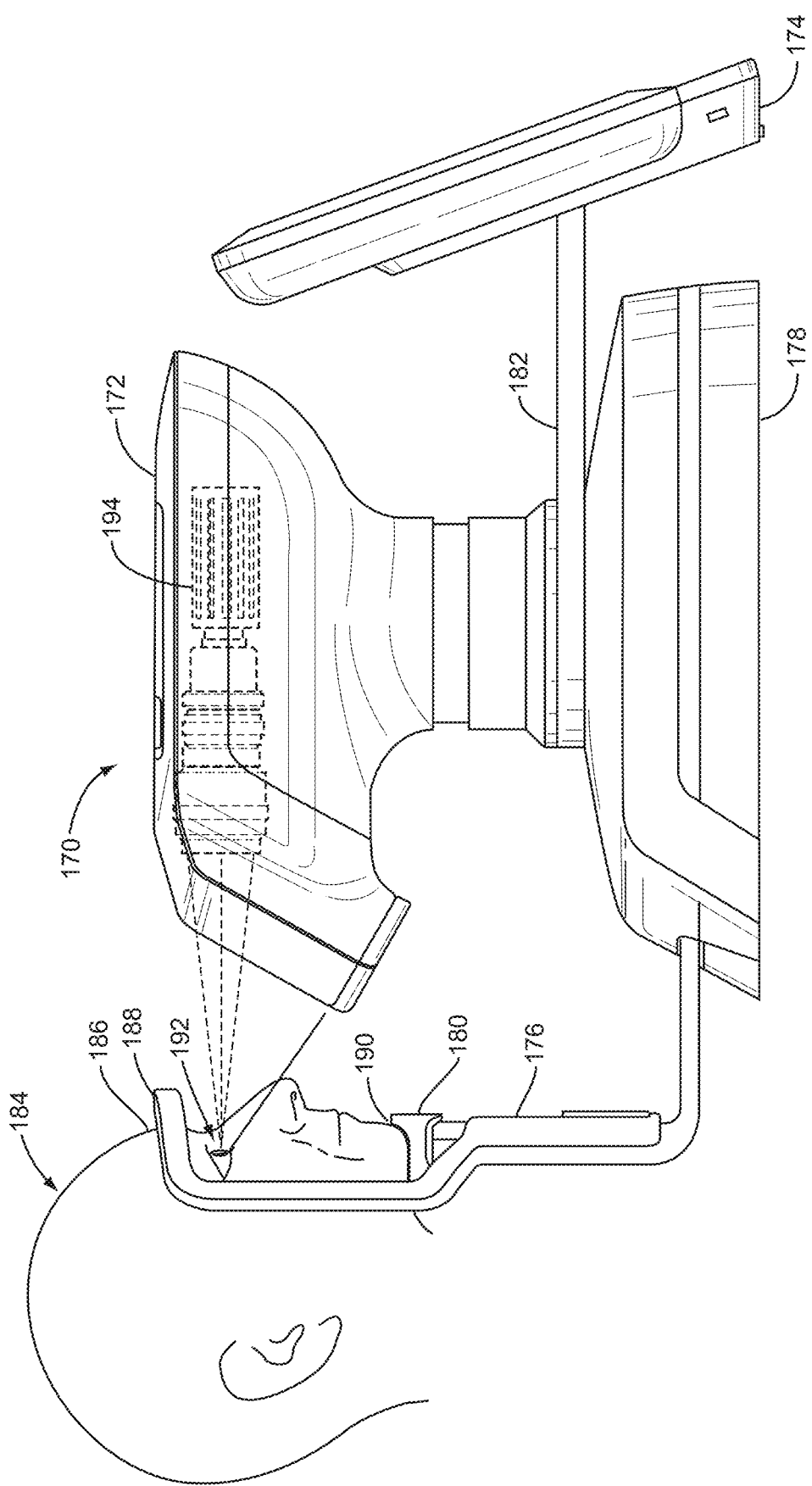
FIG. 15 is a side view of the OSI device of FIG. 14 illuminating and imaging a patient's eye and tear film.

FIG. 15 illustrates a side view of the OSI device 170 of FIG. 14 to further illustrate imaging of a patient's eye and ocular tear film. As illustrated therein, a patient places their head 184 in the patient head support 176. More particularly, the patient places their forehead 186 against a headrest 188 provided as part of the patient head support 176. The patient places their chin 190 in the chin rest 180. The patient head support 176 is designed to facilitate alignment of a patient's eye 192 with the OSI device 170, and in particular, an imaging device 194 (and illuminator) shown as being provided inside the housing 172. The chin rest 180 can be adjusted higher or lower to move the patient's eye 192 with respect to the OSI device 170.

Figure 16:
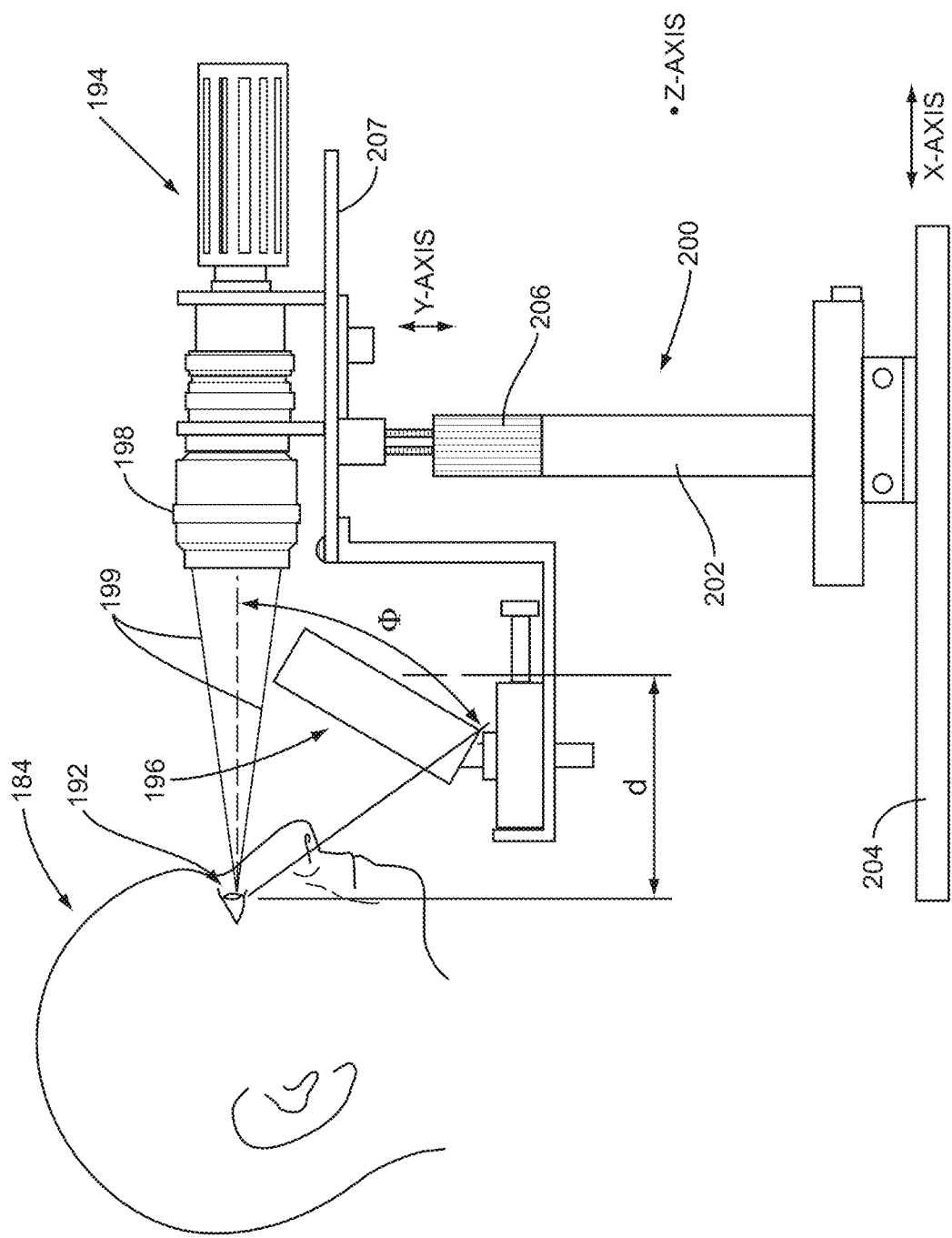
FIG. 16 is a side view of a video camera and illuminator within the OSI device of FIG. 14 imaging a patient's eye and tear film.

As shown in FIG. 16, the imaging device 194 is used to image the patient's ocular tear film to determine characteristics of the patient's tear film. In particular, the imaging device 194 is used to capture interference interactions of the specularly reflected light from the patient's tear film when illuminated by a light source 196 (also referred to herein as "illuminator 196") as well as background signal. As previously discussed, background signal may be captured when the illuminator 196 is illuminating or not illuminating a patient's tear film. In the OSI device 170, the imaging device 194 is the "The Imaging Source" model DFK21BU04 charge coupling device (CCD) digital video camera 198, but many types of metrological grade cameras or imaging devices can be provided. A CCD camera enjoys characteristics of efficient light gathering, linear behavior, cooled operation, and immediate image availability. A linear imaging device is one that provides an output signal representing a captured image which is precisely proportional to the input signal from the captured image. Thus, use of a linear imaging device (e.g., gamma correction set to 1.0, or no gamma correction) provides undistorted interference data which can then be analyzed using linear analysis models. In this manner, the resulting images of the tear film do not have to be linearized before analysis, thus saving processing time. Gamma correction can then be added to the captured linear images for human-perceptible display on a non-linear display 174 in the OSI device 170. Alternatively, the opposite scenario could be employed. That is, a non-linear imaging device or non-linear setting would be provided to capture tear film images, wherein the non-linear data representing the interference interactions of the interference signal can be provided to a non-linear display monitor without manipulation to display the tear film images to a clinician. The non-linear data would be linearized for tear film processing and analysis to estimate tear film layer thickness.

The video camera 198 is capable of producing lossless full motion video images of the patient's eye. As illustrated in FIG. 16, the video camera 198 has a depth of field defined by the angle between rays 199 and the lens focal length that allows the patient's entire tear film to be in focus simultaneously. The video camera 198 has an external trigger support so that the video camera 198 can be controlled by a control system to image the patient's eye. The video camera 198 includes a lens that fits within the housing 172. The video camera 198 in this embodiment has a resolution of 640×480 pixels and is capable of frame rates up to sixty (60) frames per second (fps). The lens system employed in the video camera 198 images a 16×12 mm dimension in a sample plane onto an active area of a CCD detector within the video camera 198. As an example, the video camera 198 may be the DBK21AU04 Bayer VGA (640×480) video camera using a Pentax VS-LD25 Daitron 25-mm fixed focal length lens. Other camera models with alternate pixel size and number, alternate lenses, (etc) may also be employed.

Although a video camera 198 is provided in the OSI device 170, a still camera could also be used if the frame rate is sufficiently fast enough to produce high quality images of the patient's eye. High frame rate in frames per second (fps) facilitate high quality subtraction of background signal from a captured interference signal representing specularly reflected light from a patient's tear film, and may provide less temporal (i.e., motion) artifacts (e.g., motion blurring) in captured images, resulting in high quality captured images. This is especially the case since the patient's eye may move irregularly as well as blinking, obscuring the tear film from the imaging device during examination.

A camera positioning system 200 is also provided in the housing 172 of the OSI device 170 to position the video camera 198 for imaging of the patient's tear film. The camera positioning system 200 is under the control of a control system. In this manner, a clinician can manipulate the position of the video camera 198 to prepare the OSI device 170 to image the patient's tear film. The camera positioning system 200 allows a clinician and/or control system to move the video camera 198 between different patients' eyes 192, but can also be designed to limit the range of motion within designed tolerances. The camera positioning system 200 also allows for fine tuning of the video camera 198 position. The camera positioning system 200 includes a stand 202 attached to a base 204. A linear servo or actuator 206 is provided in the camera positioning system 200 and connected between the stand 202 and a camera platform 207 supporting the video camera 198 to allow the video camera 198 to be moved in the vertical (i.e., Y-axis) direction.

In this embodiment of the OSI device 170, the camera positioning system 200 may not allow the video camera 198 to be moved in the X-axis or the Z-axis (in and out of FIG. 16), but the invention is not so limited. The illuminator 196 is also attached to the camera platform 207 such that the illuminator 196 maintains a fixed geometric relationship to the video camera 198. Thus, when the video camera 198 is adjusted to the patient's eye 192, the illuminator 196 is automatically adjusted to the patient's eye 192 in the same regard as well. This may be important to enforce a desired distance (d) and angle of illumination (Φ) of the patient's eye 192, as illustrated in FIG. 16, to properly capture the interference interactions of the specularly reflected light from the patient's tear film at the proper angle of incidence according to Snell's law, since the OSI device 170 is programmed to assume a certain distance and certain angles of incidence. In the OSI device 170 in FIG. 16, the angle of illumination (Φ) of the patient's eye 192 relative to the camera 198 axis is approximately 30 degrees at the center of the illuminator 196 and includes a relatively large range of angles from about 5 to 60 degrees, but any angle may be provided.

System Level

Figure 17:
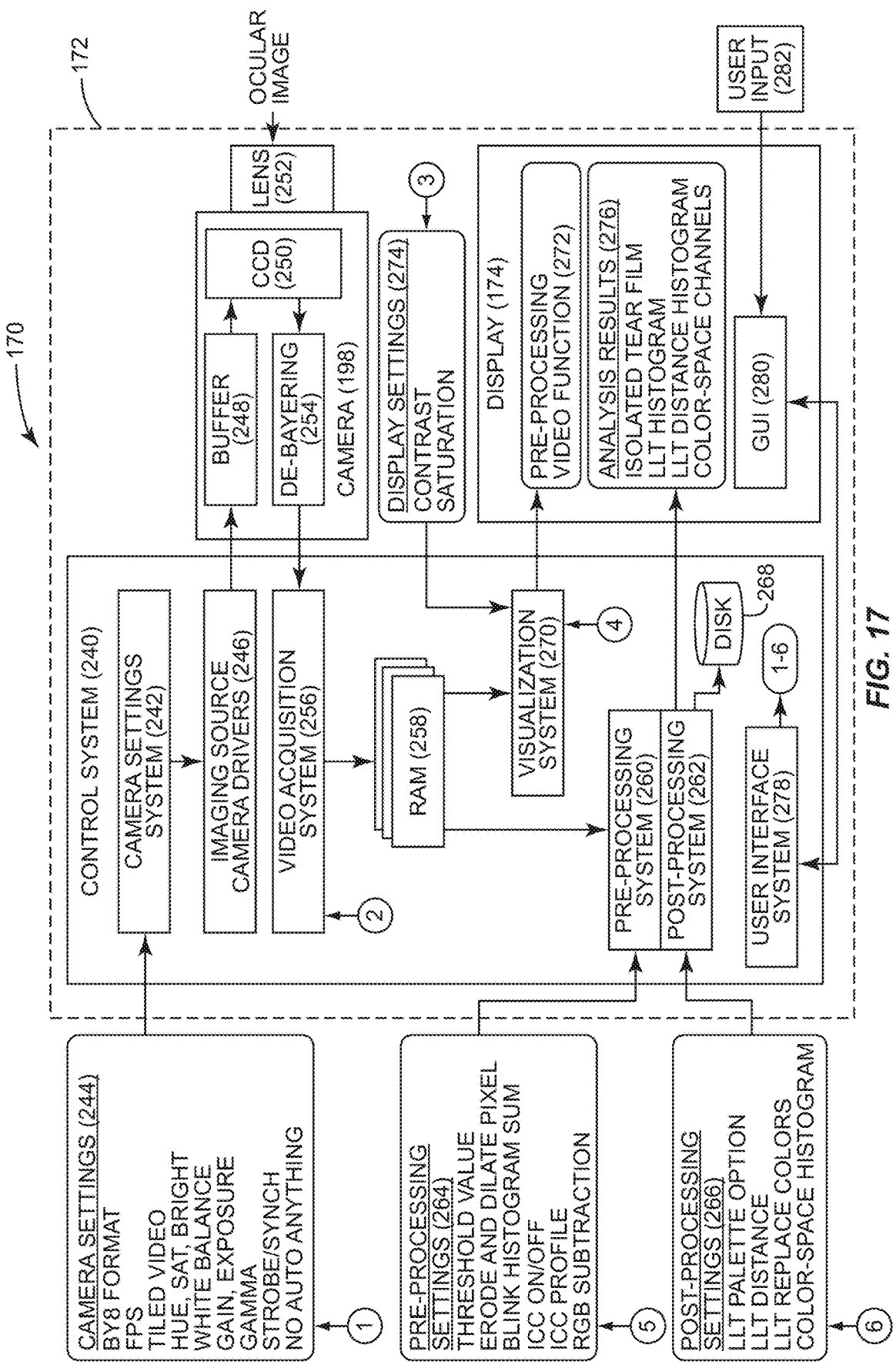
FIG. 17 illustrates an exemplary system diagram of a control system and supporting components in the OSI device of FIG. 14 that allow imaging a patient's tear film during contact lens wear to determine tear film characteristics of the tear film for determining contact lens intolerance of the patient.

Now that the imaging and illumination functions of the OSI device 170 have been described, FIG. 17 illustrates a system level diagram illustrating more detail regarding the control system and other internal components of the OSI device 170 provided inside the housing 172 according to one embodiment to capture images of a patient's tear film and process those images. As illustrated therein, a computer control system 240 is provided that provides the overall control of the OSI device 170. The computer control system 240 may be provided by any microprocessor-based or computer system. The computer control system 240 illustrated in FIG. 17 is provided in a system-level diagram and does not necessarily imply a specific hardware organization and/or structure. As illustrated therein, the computer control system 240 contains several systems. A camera settings system 242 may be provided that accepts camera settings from a clinician user. Exemplary camera settings 244 are illustrated, but may be any type according to the type and model of camera provided in the OSI device 170 as is well understood by one of ordinary skill in the art.

The camera settings 244 may be provided to (The Imaging Source) camera drivers 246, which may then be loaded into the video camera 198 upon initialization of the OSI device 170 for controlling the settings of the video camera 198. The settings and drivers may be provided to a buffer 248 located inside the video camera 198 to store the settings for controlling a CCD 250 for capturing ocular image information from a lens 252. Ocular images captured by the lens 252 and the CCD 250 are provided to a de-Bayering function 254 which contains an algorithm for post-processing of raw data from the CCD 250 as is well known. The ocular images are then provided to a video acquisition system 256 in the computer control system 240 and stored in memory, such as random access memory (RAM) 258. The stored ocular images or signal representations can then be provided to a pre-processing system 260 and a post-processing system 262 to manipulate the ocular images to obtain the interference interactions of the specularly reflected light from the tear film and analyze the information to determine characteristics of the tear film. Pre-processing settings 264 and post-processing settings 266 can be provided to the pre-processing system 260 and post-processing system 262, respectively, to control these functions. These settings 264, 266 will be described in more detail below. The post-processed ocular images and information may also be stored in mass storage, such as disk memory 268, for later retrieval and viewing on the display 174.

The computer control system 240 may also contain a visualization system 270 that provides the ocular images to the display 174 to be displayed in human-perceptible form on the display 174. Before being displayed, the ocular images may have to be pre-processed in a pre-processing video function 272. For example, if the ocular images are provided by a linear camera, non-linearity (i.e. gamma correction) may have to be added in order for the ocular images to be properly displayed on the display 174. Further, contrast and saturation display settings 274, which may be controlled via the display 174 or a device communicating to the display 174, may be provided by a clinician user to control the visualization of ocular images displayed on the display 174. The display 174 is also adapted to display analysis result information 276 regarding the patient's tear film, as will be described in more detail below. The computer control system 240 may also contain a user interface system 278 that drives a graphical user interface (GUI) utility 280 on the display 174 to receive user input 282. The user input 282 can include any of the settings for the OSI device 170, including the camera settings 244, the pre-processing settings 264, the post-processing settings 266, the display settings 274, the visualization system 270 enablement, and video acquisition system 256 enablement, labeled 1-6. The GUI utility 280 may only be accessible by authorized personnel and used for calibration or settings that would normally not be changed during normal operation of the OSI device 170 once configured and calibrated.

Overall Process Flow

Figure 18:
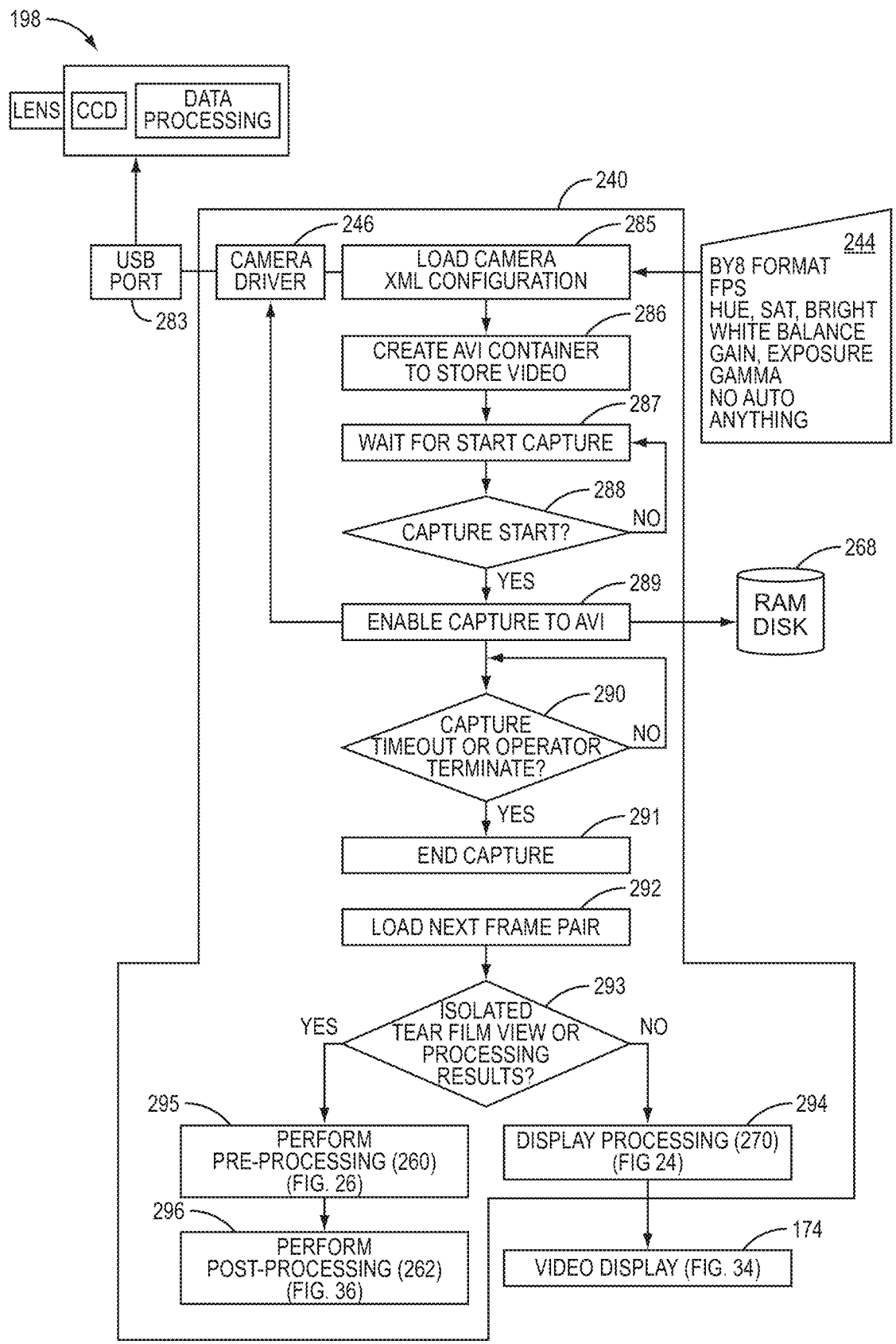
FIG. 18 is a flowchart illustrating an exemplary overall processing flow of the OSI device of FIG. 14 having systems components according to the exemplary system diagram of FIG. 17.

FIG. 18 illustrates an exemplary overall flow process performed by the OSI device 170 for capturing tear film images from a patent and analysis for determining tear film characteristics of a contact lens wearer patient. As illustrated in FIG. 18, the video camera 198 is connected via a USB port 283 to the computer control system 240 (see FIG. 17) for control of the video camera 198 and for transferring images of a patient's tear film taken by the video camera 198 back to the computer control system 240. The computer control system 240 includes a compatible camera driver 246 to provide a transfer interface between the computer control system 240 and the video camera 198. Prior to tear film image capture, the configuration or camera settings 244 are loaded into the video camera 198 over the USB port 283 to prepare the video camera 198 for tear film image capture (block 285). Further, an audio video interleaved (AVI)

container is created by the computer control system 240 to store video of tear film images to be captured by the video camera 198 (block 286). At this point, the video camera 198 and computer control system 240 are ready to capture images of a patient's tear film. The computer control system 240 waits for a user command to initiate capture of a patient's tear film (blocks 287, 288).

Autopositioning and Autofocus

Before the computer control system 240 directs the video camera 198 of the OSI device 170 in FIG. 16 to capture images of the patient's tear film, it may be desired to position and focus the video camera 198 to obtain the most accurate images of the patient's tear film possible for more accurate analysis. Positioning the video camera 198 involves positioning the lens of the video camera 198 in the Y-axis and Z-axis directions, as shown in FIG. 16, to be in the desired alignment with the patient's eye 192 and tear film to capture an image in a region of interest of the patient's tear film. As previously discussed above, it may be desired to position the video camera 198 to capture specularly reflected light from a portion of the tear film that is outside of the pupil area of the patient's eye 192. Focusing the video camera 198 means changing the focal length of the lens of the video camera 198 of the OSI device 170 in the X-axis directions, as shown in FIG. 16. Changing the focus of the video camera 198 changes the point of convergence of the specularly reflected light returned from the tear film of the patient's eye 192. Ideally, for a non-distorted image of the tear film of the patient's eye 192, the focal length should be set for the specularly reflected light returned from the tear film of the patient's eye 192 to converge at an imaging plane of the video camera 198.

The technician can position the video camera 198 in alignment with the patient's eye and tear film to be imaged. However, this introduces human error and/or involves trial and error by the technician, which may be time consuming. Further, as the OSI device 170 is used to image different eyes of the same patient, or a new patient, the video camera 198 may need to be re-positioned each time. Thus, in embodiments disclosed herein, the video camera 198 can be autopositioned by the OSI device 170. In this regard, the computer control system 240 in FIG. 17 can be programmed to autoposition the video camera 198 when desired. For example, it may be desired for the computer control system 240 to be programmed to autoposition the video camera 198 prior to step 287 in FIG. 18, where the video camera 198 and supporting components for storing images of the patient's eye 192 are being configured and initialized.

With reference back to FIG. 18, once image capture is initiated (block 288), the computer control system 240 enables image capture to the AVI container previously setup (block 286) for storage of images captured by the video camera 198 (block 289). The computer control system 240 controls the video camera 198 to capture images of the patient's tear film (block 289) until timeout or the user terminates image capture (block 290) and image capture halts or ends (block 291). Images captured by the video camera 198 and provided to the computer control system 240 over the USB port 283 are stored by the computer control system 240 in RAM 268.

The captured images of the patient's ocular tear film can subsequently be processed and analyzed to determine tear film characteristics of a contact lens wearer patient, as described in more detail below and throughout the remainder of this disclosure. The process in this embodiment involves processing tear film image pairs to perform background subtraction, as previously discussed. For example, image tiling may be performed to provide the tear film image pairs, if desired. The processing can include simply displaying the patient's tear film or determining tear film characteristics of a contact lens wearer patient (block 293). If the display option is selected to allow a technician to visually view the patient's tear film, display processing is performed (block 294) which can be the display processing 270 described in more detail below with regard to FIG. 36. For example, the computer control system 240 can provide a combination of images of the patient's tear film that show the entire region of interest of the tear film on the display 174. The displayed image may include the background signal or may have the background signal subtracted. If determining tear film characteristics of a contact lens wearer patient is desired, the computer control system 240 performs pre-processing of the tear film images for determining tear film characteristics of a contact lens wearer patient (block 295), which can be the pre-processing 260 described in more detail below with regard to FIG. 28. The computer control system 240 also performs post-processing of the tear film images for determining tear film characteristics of a contact lens wearer patient (block 296), which can be the post-processing 262 described in more detail below with regard to FIG. 28.

Pre-Processing

Figure 19:
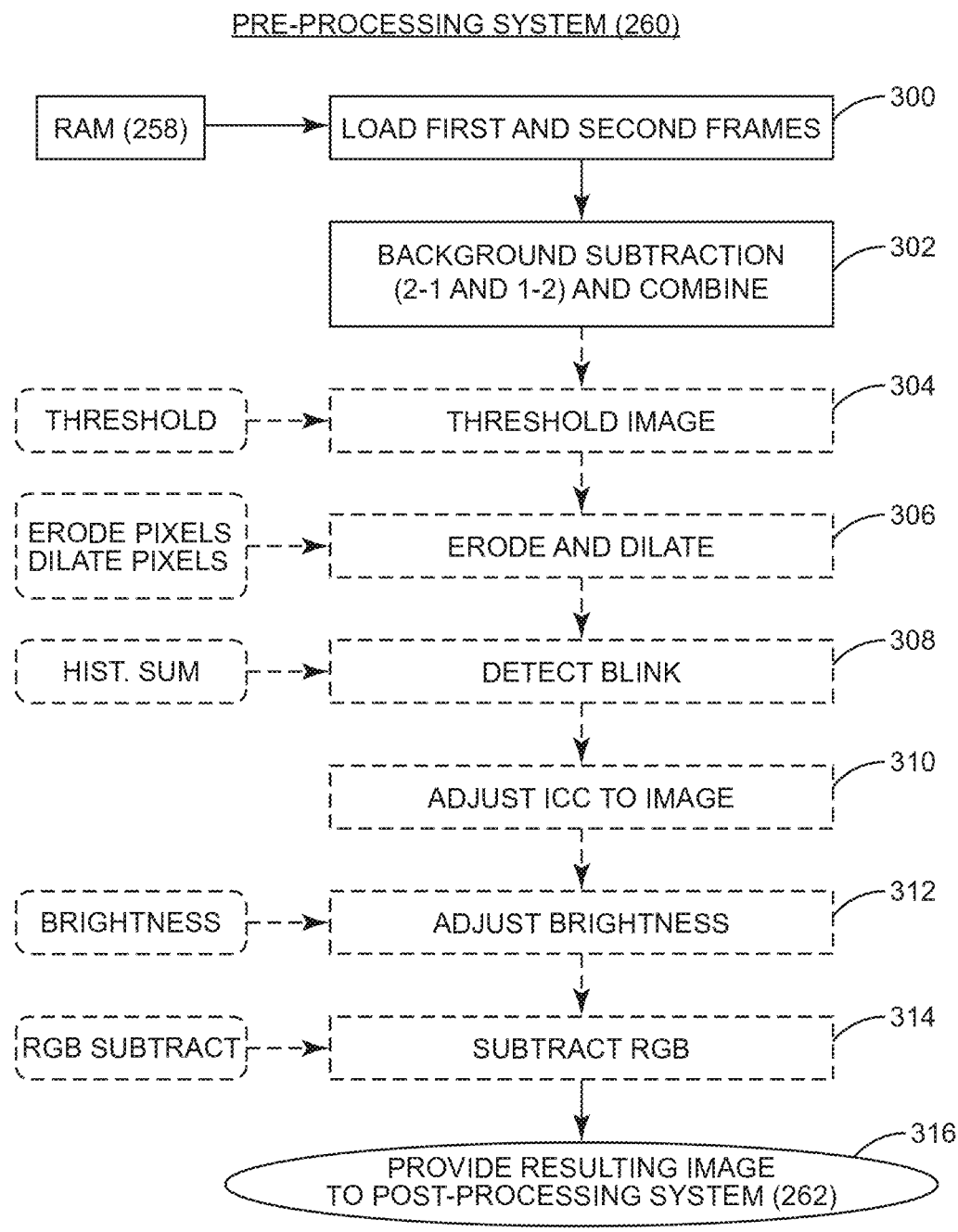
FIG. 19 is a flowchart illustrating exemplary pre-processing steps performed on the combined first and second images of a patient's tear film involving contact lens wear before measuring tear film layer thickness (TFLT)
Figure 20:
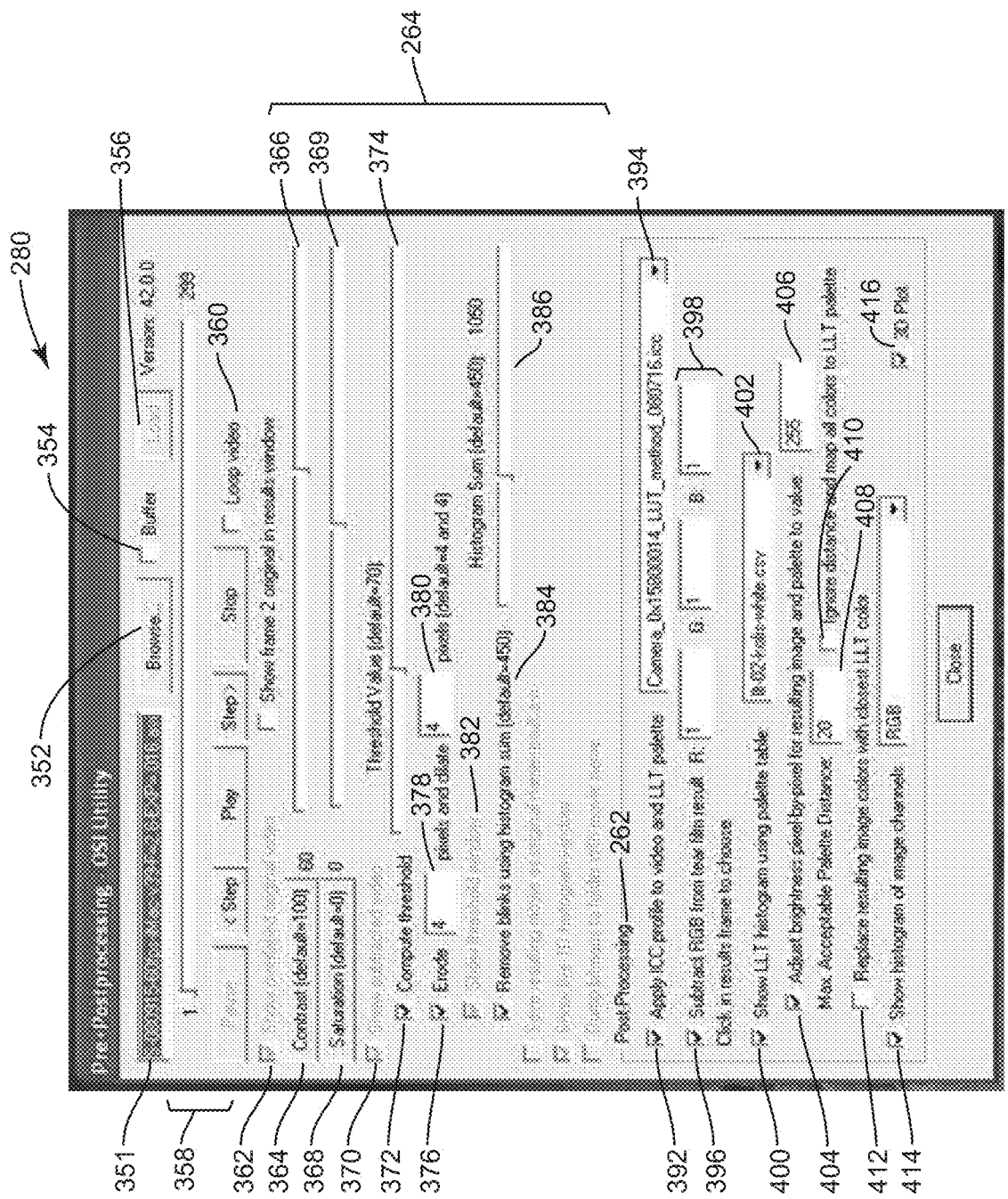
FIG. 20 is an exemplary graphical user interface (GUI) for controlling imaging, pre-processing, and post-processing settings of the OSI device of FIG. 14.

FIG. 19 illustrates an exemplary pre-processing system 260 for pre-processing ocular tear film images captured by the OSI device 170 for eventual analysis and determining tear film characteristics of a contact lens wearer patient. In this system, the video camera 198 has already taken the first and second tiled images of a patient's ocular tear film, as previously illustrated in FIGS. 11-13, and provided the images to the video acquisition system 256. The frames of the first and second images were then loaded into RAM 258 by the video acquisition system 256. Thereafter, as illustrated in FIG. 19, the computer control system 240 commands the pre-processing system 260 to pre-process the first and second images. An exemplary GUI utility 280 is illustrated in FIG. 20 that may be employed by the computer control system 240 to allow a clinician to operate the OSI device 170 and control pre-processing settings 264 and post-processing settings 266, which will be described later in this application. In this regard, the pre-processing system 260 loads the first and second image frames of the ocular tear film from RAM 258 (block 300). The exemplary GUI utility 280 in FIG. 19 allows for a stored image file of previously stored video sequence of first and second image frames captured by the video camera 198 by entering a file name in the file name field 351. A browse button 352 also allows searches of the memory for different video files, which can either be buffered by selecting a buffered box 354 or loaded for pre-processing by selecting the load button 356.

If the loaded first and second image frames of the tear film are buffered, they can be played using display selection buttons 358, which will in turn display the images on the display 174. The images can be played on the display 174 in a looping fashion, if desired, by selecting the loop video selection box 360. A show subtracted video selection box 370 in the GUI utility 280 allows a clinician to show the resulting, subtracted video images of the tear film on the display 174 representative of the resulting signal comprised of the second output signal combined or subtracted from the first output signal, or vice versa. Also, by loading the first and second image frames, the previously described subtraction technique can be used to remove background image from the interference signal representing interference of the specularly reflected light from the tear film, as previously described above and illustrated in FIG. 13 as an example. The first image is subtracted from the second image to subtract or remove the background signal in the portions producing specularly reflected light in the second image, and vice versa, and then combined to produce an interference interaction of the specularly reflected light of the entire area or region of interest of the tear film, as previously illustrated in FIG. 13 (block 302 in FIG. 19). For example, this processing could be performed using the Matlab® function "cvAbsDiff."

Figure 21:
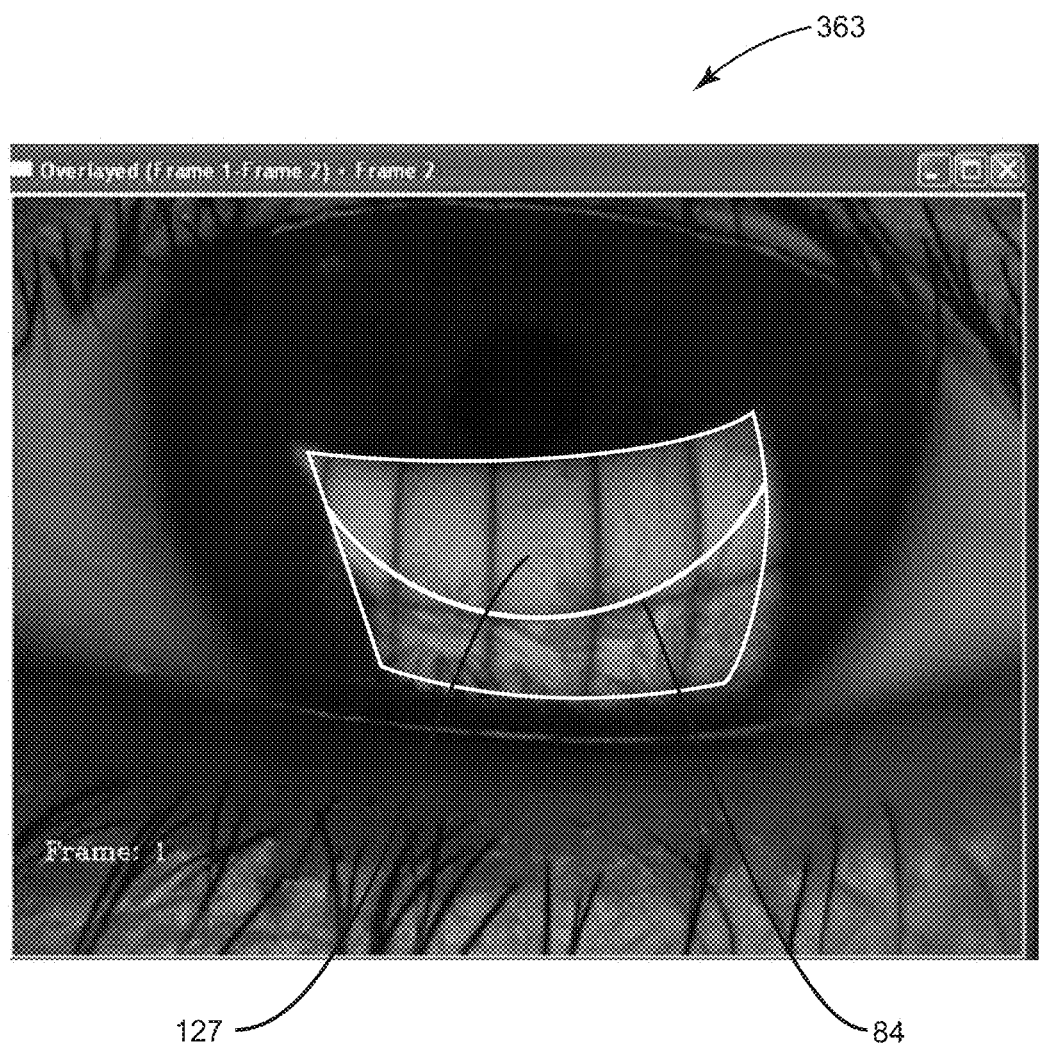
FIG. 21 illustrates an example of a subtracted image in an area or region of interest of a tear film involving contact lens wear that contains specularly reflected light from the tear film overlaid on top of a background image of the tear film.

The subtracted image containing the specularly reflected light from the tear film can also be overlaid on top of the original image capture of the tear film to display an image of the entire eye and the subtracted image in the display 174 by selecting the show overlaid original video selection box 362 in the GUI utility 280 of FIG. 20. An example of an overlaid original video to the subtracted image of specularly reflected light from the tear film is illustrated in the image 363 of FIG. 21. This overlay is provided so that flashing images of specularly reflected light from the tear film are not displayed, which may be unpleasant to visualize. The image 363 of the tear film illustrated in FIG. 21 was obtained with a DBK 21AU04 Bayer VGA (640×480) video camera having a Pentax VS-LD25 Daitron 25-mm fixed focal length lens with maximum aperture at a working distance of 120 mm and having the following settings, as an example:

Gamma=100 (to provide linearity with exposure value)
Exposure=1/16 second
Frame rate=60 fps
Data Format=BY8
Video Format=–uncompressed, RGB 24-bit AVI
Hue=180 (neutral, no manipulation)
Saturation=128 (neutral, no manipulation)
Brightness=0 (neutral, no manipulation)
Gain=260 (minimum available setting in this camera driver)
White balance=B=78; R=20.

Thresholding

Any number of optional pre-processing steps and functions can next be performed on the resulting combined tear film image(s), which will now be described. For example, an optional threshold pre-processing function may be applied to the resulting image or each image in a video of images of the tear film (e.g., FIG. 13) to eliminate pixels that have a subtraction difference signal below a threshold level (block 304 in FIG. 19). Image threshold provides a black and white mask (on/off) that is applied to the tear film image being processed to assist in removing residual information that may not be significant enough to be analyzed and/or may contribute to inaccuracies in analysis of the tear film. The threshold value used may be provided as part of a threshold value setting provided by a clinician as part of the pre-processing settings 264. For example, the GUI utility 280 in FIG. 20 includes a compute threshold selection box 372 that may be selected to perform thresholding, where the threshold brightness level can be selected via the threshold value slide 374. The combined tear film image or the contact lens-based region of interest 127 of FIG. 13 is copied and converted to grayscale. The grayscale image has a threshold applied according to the threshold setting to obtain a binary (black/white) image that will be used to mask the combined tear film image of FIG. 13. After the mask is applied to the combined tear film image of FIG. 13, the new combined tear film image is stored in RAM 258. The areas of the tear film image that do not meet the threshold brightness level are converted to black as a result of the threshold mask.

Figure 22A:
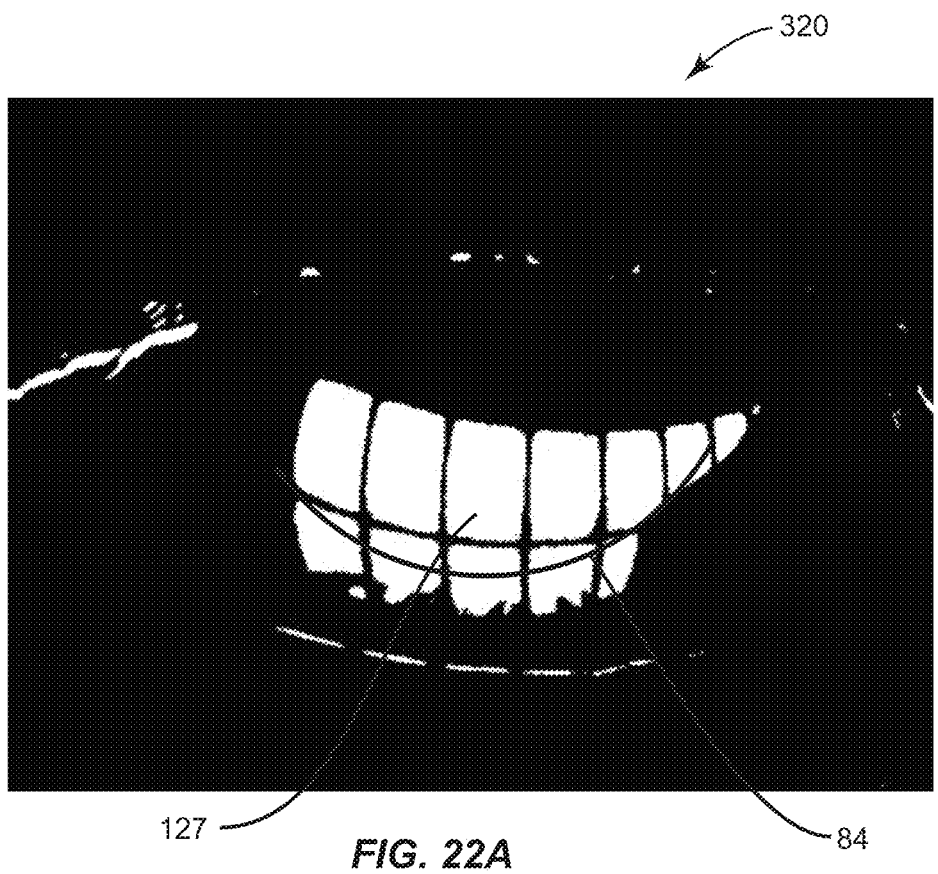
FIGS. 22A and 22B illustrate exemplary threshold masks that may be used to provide a threshold function during pre-processing of a resulting image containing specularly reflected light from a patient's tear film involving contact lens wear.
Figure 22B:
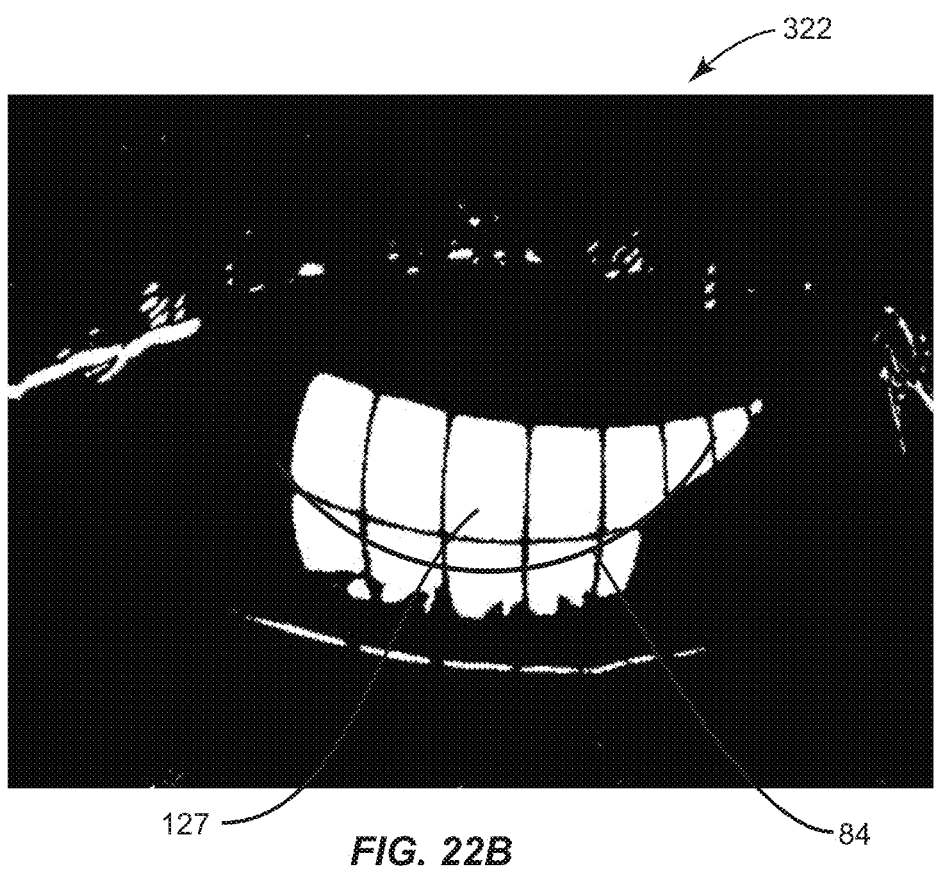
Figure 23:
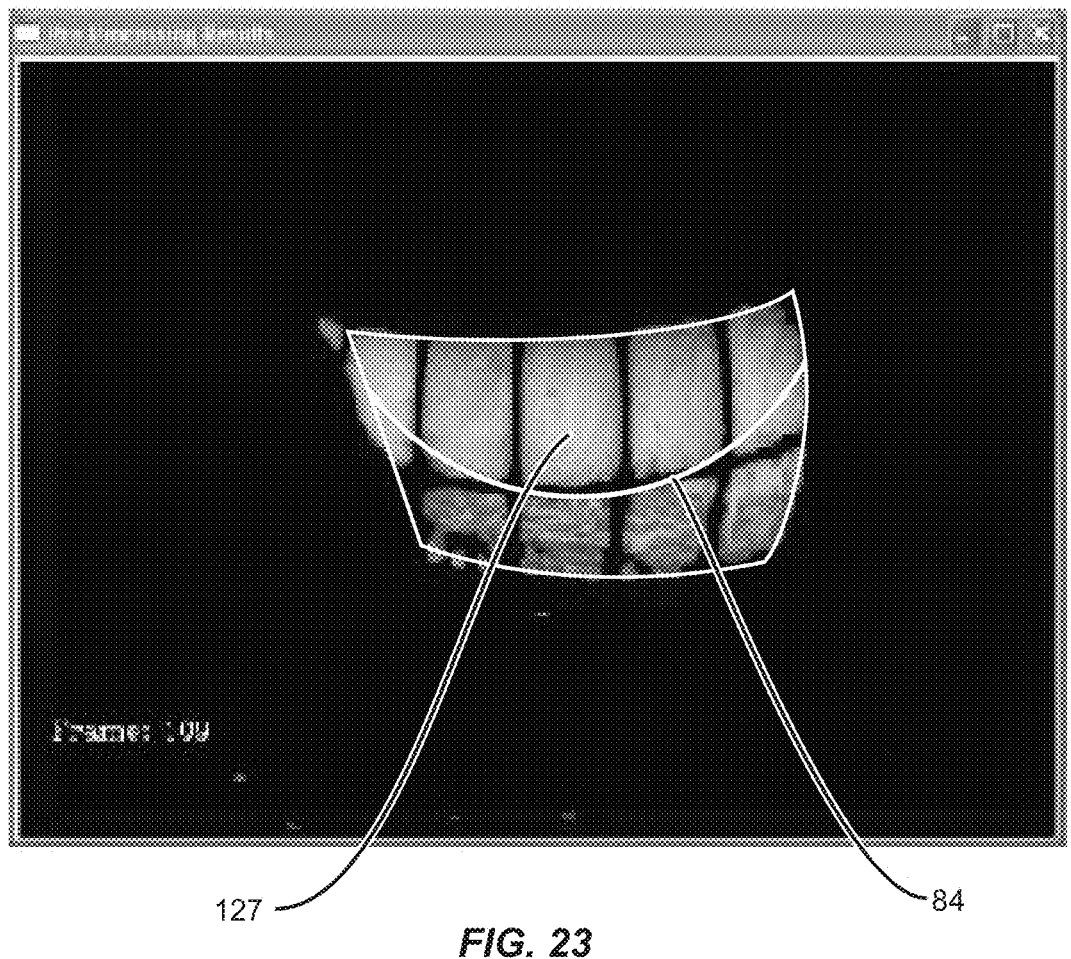
FIG. 23 illustrates an exemplary image of FIG. 21 after a threshold pre-processing function has been performed leaving interference of the specularly reflected light from the patient's tear film involving contact lens wear.

FIGS. 22A and 22B illustrate examples of threshold masks for the combined tear film provided in FIG. 13. FIG. 22A illustrates a threshold mask 320 for a threshold setting of 70 counts out of a full scale level of 255 counts. FIG. 22B illustrates a threshold mask 322 for a threshold setting of 50. Note that the threshold mask 320 in FIG. 22A contains less portions of the combined tear film image, because the threshold setting is higher than for the threshold mask 322 of FIG. 22B. When the threshold mask according to a threshold setting of 70 is applied to the exemplary combined tear film image of FIG. 13, the resulting tear film image is illustrated FIG. 23. Much of the residual subtracted background image that surrounds the area or region of interest has been masked away.

Erode and Dilate

Figure 24:
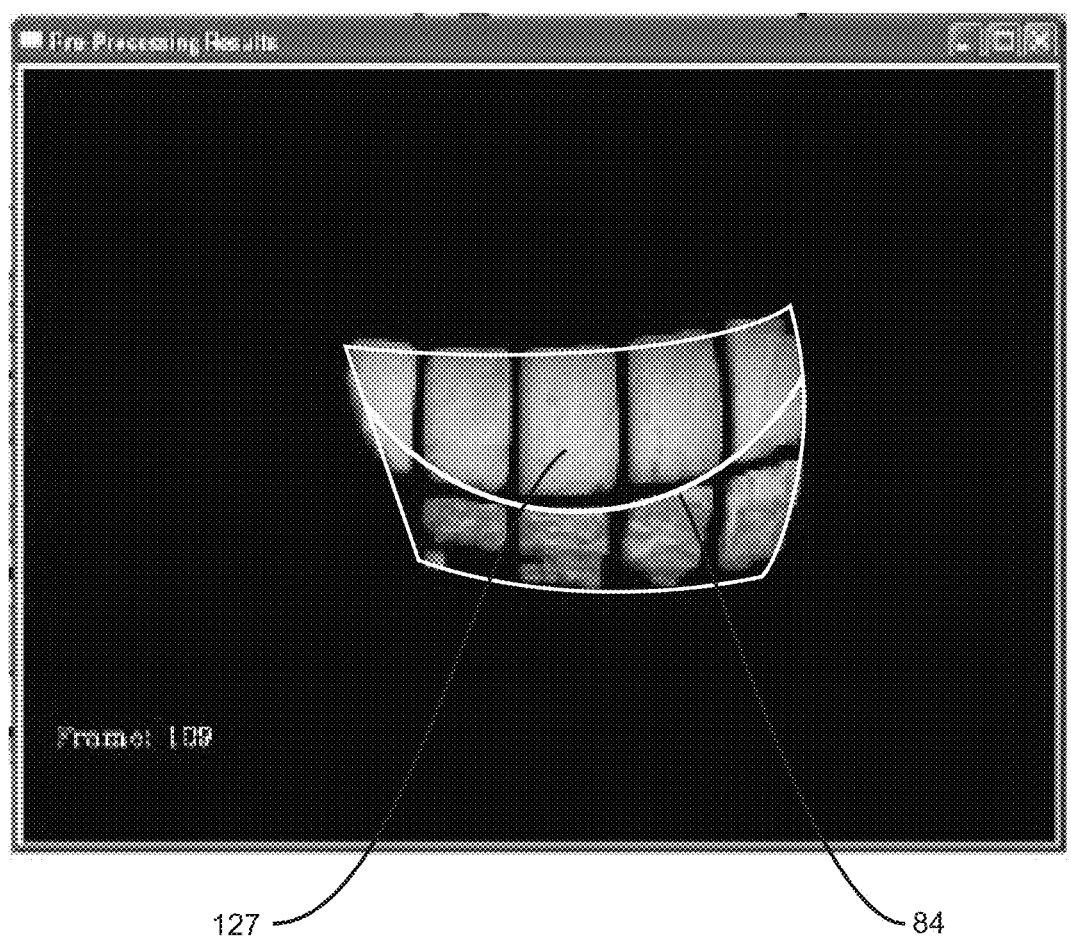
FIG. 24 illustrates an exemplary image of the image of FIG. 23 after erode and dilate pre-processing functions have been performed on the image.

Another optional pre-processing function that may be applied to the resulting image or each image in a video of images of the tear film to correct anomalies in the combined tear film image(s) is the erode and dilate functions (block 306 in FIG. 19). The erode function generally removes small anomaly artifacts by subtracting objects with a radius smaller than an erode setting (which is typically in number of pixels) removing perimeter pixels where interference information may not be as distinct or accurate. The erode function may be selected by a clinician in the GUI utility 280 (see FIG. 20) by selecting the erode selection box 376. If selected, the number of pixels for erode can be provided in an erode pixels text box 378. Dilating generally connects areas that are separated by spaces smaller than a minimum dilate size setting by adding pixels of the eroded pixel data values to the perimeter of each image object remaining after the erode function is applied. The dilate function may be selected by a clinician in the GUI utility 280 (see FIG. 20) by providing the number of pixels for dilating in a dilate pixels text box 380. Erode and dilate can be used to remove small region anomalies in the resulting tear film image prior to analyzing the interference interactions to reduce or avoid inaccuracies. The inaccuracies may include those caused by bad pixels of the video camera 198 or from dust that may get onto a scanned image, or more commonly, spurious specular reflections such as: tear film meniscus at the juncture of the eyelids, glossy eyelash glints, wet skin tissue, etc. FIG. 24 illustrates the resulting tear film image of FIG. 23 after erode and dilate functions have been applied and the resulting tear film image is stored in RAM 258. As illustrated therein, pixels previously included in the tear film image that were not in the tear film area or region of interest are removed. This prevents data in the image outside the area or region of interest from affecting the analysis of the resulting tear film image(s).

Removing Blinks/Other Anomalies

Another optional pre-processing function that may be applied to the resulting image or each image in a video of images of the tear film to correct anomalies in the resulting tear film image is to remove frames from the resulting tear film image that include patient blinks or significant eye movements (block 308 in FIG. 19). As illustrated in FIG. 19, blink detection is shown as being performed after a threshold and erode and dilate functions are performed on the tear film image or video of images. Alternatively, the blink detection could be performed immediately after background subtraction, such that if a blink is detected in a given frame or frames, the image in such frame or frames can be discarded and not pre-processed. Not pre-processing images where blinks are detected may increase the overall speed of pre-processing. The remove blinks or movement pre-processing may be selectable. For example, the GUI utility 280 in FIG. 20 includes a remove blinks selection box 384 to allow a user to control whether blinks and/or eye movements are removed from a resulting image or frames of the patient's tear film prior to analysis. Blinking of the eyelids covers the ocular tear film, and thus does not produce interference signals representing specularly reflected light from the tear film. If frames containing whole or partial blinks obscuring the area or region of interest in the patient's tear film are not removed, it would introduce errors in the analysis of the interference signals to determine characteristics of the patient's ocular tear film involving contact lens wear. Further, frames or data with significant eye movement between sequential images or frames can be removed during the detect blink pre-processing function. Large eye movements could cause inaccuracy in analysis of a patient's tear film or any area of interest when employing subtraction techniques to remove background signal, because subtraction involves subtracting frame-pairs in an image that closely match spatially. Thus, if there is significant eye movement between first and second images that are to be subtracted, frame pairs may not be closely matched spatially thus inaccurately removing background signal, and possibly removing a portion of the interference image of specularly reflected light from the tear film.

Different techniques can be used to determine blinks in an ocular tear film image and remove the frames as a result. For example, in one embodiment, the computer control system 240 directs the pre-processing system 260 to review the stored frames of the resulting images of the tear film to monitor for the presence of an eye pupil using pattern recognition. A Hough Circle Transform may be used to detect the presence of the eye pupil in a given image or frame. If the eye pupil is not detected, it is assembled such that the image or frame contains an eye blink and thus should be removed or ignored during pre-processing from the resulting image or video of images of the tear film. The resulting image or video of images can be stored in RAM 258 for subsequent processing and/or analysis.

In this regard, in one embodiment, detecting eye blinks in an ocular tear film image or frame by detecting the pupil and removing desired blink frames that do not contain an image of the pupil as a result may be performed as follows. First, ocular tear film frame pairs, one containing specularly reflected light and background signal (i.e., frame 1), and the other containing background signal (i.e., frame 2) are added together to provide a resultant image (i.e., frame 1+[frame 2−frame 1]). A grayscale is created of the resultant image, for example using a 8-bit, 255 value scale. Providing a grayscale of the resultant image allows enhanced identification of darker pixels as opposed to lighter pixels, to try to identify pixels associated with the pupil, as a non-limiting example. As discussed above, determining that a pupil is in an ocular tear film image is one direct indication of whether the ocular tear film frame contains a partial or full eye blink. Thereafter in this example, the darkest pixel in resultant grayscale frame is found. Then, all pixels within a given intensity count are found (e.g., within 7). These are the darkest areas of the frame and include the pupil. A binary resultant frame is then created with resultant grayscale frame to transform the darker pixels to white color. That binary resultant frame is then eroded and dilated (similar to as discussed in other examples herein for tear film measurement purposes) using a sample disk. The larger or largest contiguous pixels having white color is found in the resultant binary frame. A check is next made to make sure that larger or largest contiguous pixels having white color contains at least a desired minimum number of pixels (e.g., 3000) and has a desired eccentricity (e.g., 0.8 or lower). If so, this larger or largest contiguous pixels having white color is deemed to be the pupil. If previous frame from the current frame was also deemed to contain the pupil by ensuring the centroid of the larger or largest contiguous pixels did not shift by more than a designated number of pixels (e.g., 50 pixels), then the current frame is deemed to contain the pupil and is not rejected. If the current frame is not deemed to contain the pupil, the frame can be rejected.

In another embodiment, blinks and significant eye movements are detected using a histogram sum of the intensity of pixels in a resulting subtracted image or frame of a first and second image of the tear film. The resulting or subtracted image can be converted to grayscale (i.e., 255 levels) and a histogram generated with the gray levels of the pixels. The total of all the histogram bins are summed. In the case of two identical frames that are subtracted, the histogram sum would be zero. However, even without an eye blink or significant eye movement, two sequentially captured frames of the patient's eye and the interference signals representing the specularly reflected light from the tear film are not identical. However, frame pairs with little movement will have a low histogram sum, while frame pairs with greater movement will yield a larger histogram sum. If the histogram sum is beyond a pre-determined threshold, an eye blink or large eye movement can be assumed and the image or frame removed. For example, the GUI utility 280 illustrated in FIG. 20 includes a histogram sum slide bar 386 that allows a user to set the threshold histogram sum. The threshold histogram sum for determining whether a blink or large eye movement should be assumed and thus the image removes from analysis of the patient's tear film can be determined experimentally, or adaptively over the course of a frame playback, assuming that blinks occur at regular intervals.

An advantage of a histogram sum of intensity method to detect eye blinks or significant eye movements is that the calculations are highly optimized as opposed to pixel-by-pixel analysis, thus assisting with real-time processing capability. Further, there is no need to understand the image structure of the patient's eye, such as the pupil or the iris details. Further, the method can detect both blinks and eye movements.

In this regard, in one embodiment, detecting eye blinks in an ocular tear film image or frame based on an intensity method may be performed as follows. First, the ocular tear film frame pairs, one containing specularly reflected light and background signal (i.e., frame 1), and the other containing background signal (i.e., frame 2) are subtracted from each together to provide a resultant image (i.e., [frame 2−frame 1]). A grayscale is created of the resultant image (e.g., 8-bits, 255 sample levels). A histogram is then calculated for the resultant grayscale image by, for example, dividing intensity in the resultant grayscale image into a desired number of bins (e.g., 64 bins of 4 counts each). The height of the tallest bin is set to a defined level (e.g., 200) and the scale of all other bins adjusted accordingly. All scaled bins are summed and compared to a predefined limit (e.g., 1000). If histogram sum is greater than this predefined limit, the resultant frame is rejected as a frame having a blink.

To remove blink islands, trains or sequences of consecutive non-blink frames bookended by blink frames can be identified. If a train consists of three or fewer non-blink frames, those frames can be rejected as blink frames. The centroid of each resultant subtracted frame is calculated to find the location of each non-blink pixel (e.g., find the average location in X-Y coordinates of center of non-blink pixel). A bounding box of each resultant subtracted frame is also calculated. The average centroid location is calculated for all non-blink frames. The average bounding box location is calculated for all non-blink frames. If the centroid for a given frame deviates from the average centroid location for all frames by more than a defined number of pixels (e.g., 30) up, down, or temporally (from temple or nose of patient), then that frame can be rejected as a blink frame. If top, bottom, or temporal edges of bounding box deviate from the average bounding box location by more than 30 pixels, the frame can be rejected as a blink frame. The blink island removal process can be repeated labeling blink islands as either blink or non-blink islands. Optionally, a first number of frames (e.g., 5) after each blink to allow tear film to stabilize before quantifying lipid layer thickness.

Another alternate technique to detect blinks in the tear film image or video of images for possible removal is to calculate a simple average gray level in an image or video of images. Because the subtracted, resulting images of the tear film subtract background signal, and have been processed using a threshold mask, and erode and dilate functions performed in this example, the resulting images will have a lower average gray level due to black areas present than if a blink is present. A blink contains skin color, which will increase the average gray level of an image containing a blink. A threshold average gray level setting can be provided. If the average gray level of a particular frame is below the threshold, the frame is ignored from further analysis or removed from the resulting video of frames of the tear film.

Another alternate technique to detect blinks in an image or video of images for removal is to calculate the average number of pixels in a given frame that have a gray level value below a threshold gray level value. If the percentage of pixels in a given frame is below a defined threshold percentage, this can be an indication that a blink has occurred in the frame, or that the frame is otherwise unworthy of consideration when analyzing the tear film. Alternatively, a spatial frequency calculation can be performed on a frame to determine the amount of fine detail in a given frame. If the detail present is below a threshold detail level, this may be an indication of a blink or other obscurity of the tear film, since skin from the eyelid coming down and being captured in a frame will have less detail than the subtracted image of the tear film. A histogram can be used to record any of the above-referenced calculations to use in analyzing whether a given frame should be removed from the final pre-processed resulting image or images of the tear film for analysis.

ICC Profiling

Figure 25:
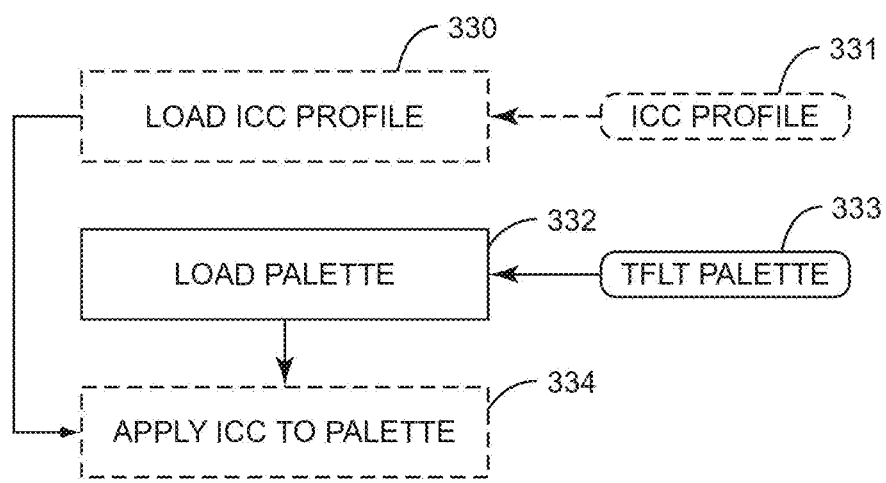
FIG. 25 illustrates an exemplary process for loading an International Colour Consortium (ICC) profile and tear film interference model into the OSI device of FIG. 14.

Pre-processing of the resulting tear film image(s) may also optionally include applying an International Colour Consortium (ICC) profile to the pre-processed interference images of the tear film (block 310, FIG. 19). FIG. 25 illustrates an optional process of loading an ICC profile into an ICC profile 331 in the computer control system 240 (block 330). In this regard, the GUI utility 280 illustrated in FIG. 20 also includes an apply ICC box 392 that can be selected by a clinician to load the ICC profile 331. The ICC profile 331 may be stored in memory in the computer control system 240, including in RAM 258. In this manner, the GUI utility 280 in FIG. 20 also allows for a particular ICC profile 331 to be selected for application in the ICC profile file text box 394. The ICC profile 331 can be used to adjust color reproduction from scanned images from cameras or other devices into a standard red-green-blue (RGB) color space (among other selectable standard color spaces) defined by the ICC and based on a measurement system defined internationally by the Commission Internationale de l'Eclairage (CIE). Adjusting the pre-processed resulting tear film interference images corrects for variations in the camera color response and the light source spectrum and allows the images to be compatibly compared with a tear film layer interference model to measure the thickness of a TFLT, as will be described later in this application. The tear film layers represented in the tear film layer interference model can be LLTs, ALTs, or both, as will be described in more detail below.

In this regard, the ICC profile 331 may have been previously loaded to the OSI device 170 before imaging of a patient's tear film and also applied to a tear film layer interference model when loaded into the OSI device 170 independent of imaging operations and flow. As will be discussed in more detail below, a tear film layer interference model in the form of a TFLT palette 333 containing color values representing interference interactions from specularly reflected light from a tear film for various LLTs and ALTs can also be loaded into the OSI device 170 (block 332 in FIG. 25). The tear film layer interference model 333 contains a series of color values that are assigned LLTs and/or ALTs based on a theoretical tear film layer interference model to be compared against the color value representations of interference interactions in the resulting image(s) of the patient's tear film. When applying the optional ICC profile 331 to the tear film layer interference model 333 (block 334 in FIG. 25), the color values in both the tear film layer interference model and the color values representing interference interactions in the resulting image of the tear film are adjusted for a more accurate comparison between the two to measure LLT and/or ALT.

Brightness

Also as an optional pre-processing step, brightness and red-green-blue (RGB) subtract functions may be applied to the resulting interference signals of the patient's tear film before post-processing for analysis and measuring TFLT is performed (blocks 312 and 314 in FIG. 19). The brightness may be adjusted pixel-by-pixel by selecting the adjust brightness selection box 404 according to a corresponding brightness level value provided in a brightness value box 406, as illustrated in the GUI utility 280 of FIG. 20. When the brightness value box 406 is selected, the brightness of each palette value of the tear film interference model 333 is also adjusted accordingly.

RGB Subtraction (Normalization)

The RGB subtract function subtracts a DC offset from the interference signal in the resulting image(s) of the tear film representing the interference interactions in the interference signal. An RGB subtract setting may be provided from the pre-processing settings 264 to apply to the interference signal in the resulting image of the tear film to normalize against. As an example, the GUI utility 280 in FIG. 20 allows an RGB offset to be supplied by a clinician or other technician for use in the RGB subtract function. As illustrated therein, the subtract RGB function can be activated by selecting the RGB subtract selection box 396. If selected, the individual RGB offsets can be provided in offset value input boxes 398. After pre-processing is performed, if any, on the resulting image, the resulting image can be provided to a post-processing system to measure TFLT (block 316 in FIG. 19), as discussed later below in this application.

Displaying Images

The resulting images of the tear film may also be displayed on the display 174 of the OSI device 170 for human diagnosis of the patient's ocular tear film. The OSI device 170 is configured so that a clinician can display and see the raw captured image of the patient's eye 192 by the video camera 198, the resulting images of the tear film before pre-processing, or the resulting images of the tear film after pre-processing. Displaying images of the tear film on the display 174 may entail different settings and steps. For example, if the video camera 198 provides linear images of the patient's tear film, the linear images must be converted into a non-linear format to be properly displayed on the display 174. In this regard, a process that is performed by the visualization system 270 according to one embodiment is illustrated in FIG. 26.

Figure 26:
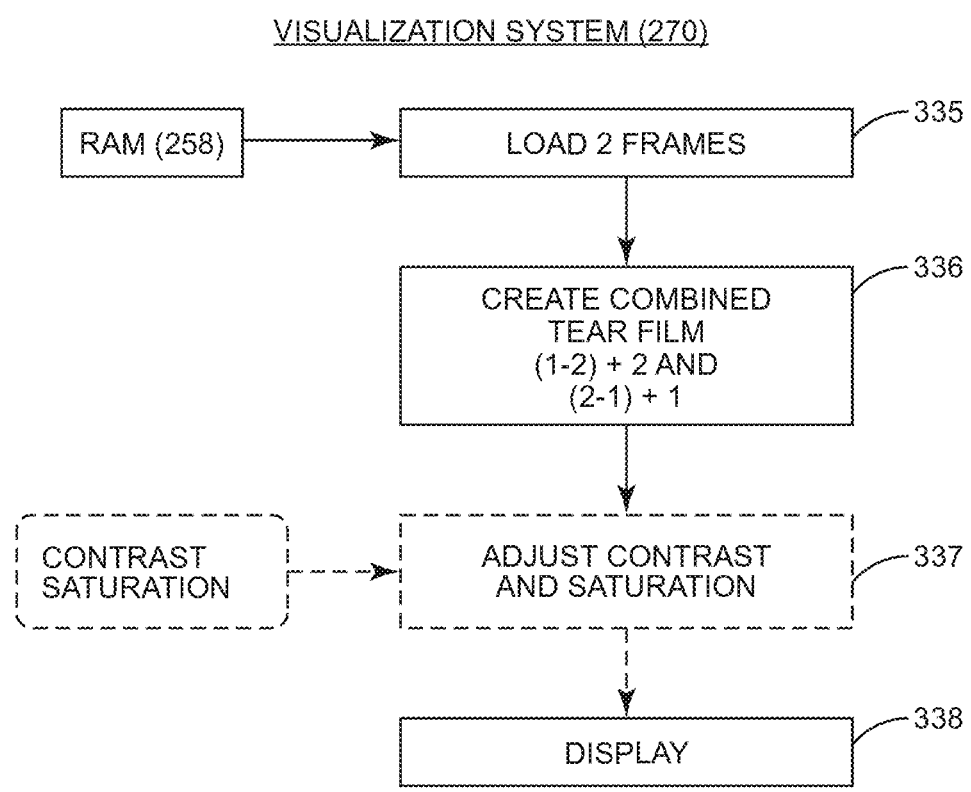
FIG. 26 illustrates a flowchart providing an exemplary visualization system process for displaying images of a patient's tear film involving contact lens wear on a display in the OSI device of FIG. 14.

As illustrated in FIG. 26, the video camera 198 has already taken the first and second tiled images of a patient's ocular tear film as previously illustrated in FIGS. 11-13, and provided the images to the video acquisition system 256. The frames of the first and second images were then loaded into RAM 258 by the video acquisition system 256. Thereafter, as illustrated in FIG. 26, the computer control system 240 commands the visualization system 270 to process the first and second images to prepare them for being displayed on the display 174, 338. In this regard, the visualization system 270 loads the first and second image frames of the ocular tear film from RAM 258 (block 335). The previously described subtraction technique is used to remove background signal from the interference interactions of the specularly reflected light from the tear film, as previously described above and illustrated in FIG. 13. The first image(s) is subtracted from the second image(s) to remove background signal in the illuminated portions of the first image(s), and vice versa, and the subtracted images are then combined to produce an interference interaction of the specularly reflected light of the entire area or region of interest of the tear film, as previously discussed and illustrated in FIG. 13 (block 336 in FIG. 26).

Again, for example, this processing could be performed using the Matlab® function "cvAbsDiff." Before being displayed, the contrast and saturation levels for the resulting images can be adjusted according to contrast and saturation settings provided by a clinician via the user interface system 278 and/or programmed into the visualization system 270 (block 337). For example, the GUI utility 280 in FIG. 20 provides an apply contrast button 364 and a contrast setting slide 366 to allow the clinician to set the contrast setting in the display settings 274 for display of images on the display 174. The GUI utility 280 also provides an apply saturation button 368 and a saturation setting slide 369 to allow a clinician to set the saturation setting in the display settings 274 for the display of images on the display 174. The images can then be provided by the visualization system 270 to the display 174 for displaying (block 338 in FIG. 26). Also, any of the resulting images after pre-processing steps in the pre-processing system 260 can be provided to the display 174 for processing.

Figure 27A:
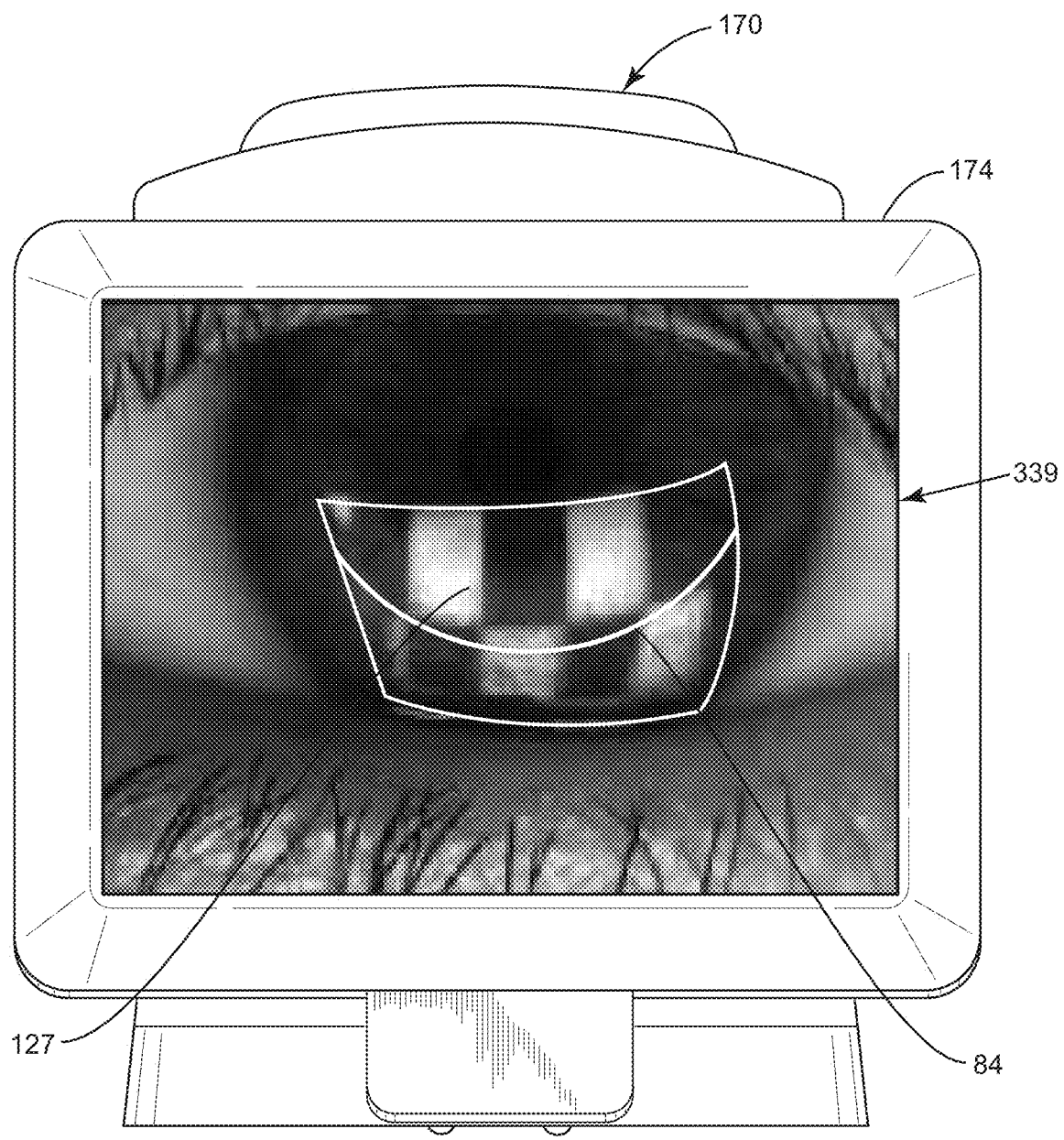
FIGS. 27A-27C illustrate exemplary images of a patient's tear film involving contact lens wear with a tiled pattern of interference interactions from specularly reflected light from the tear film displayed on a display.
Figure 27B:
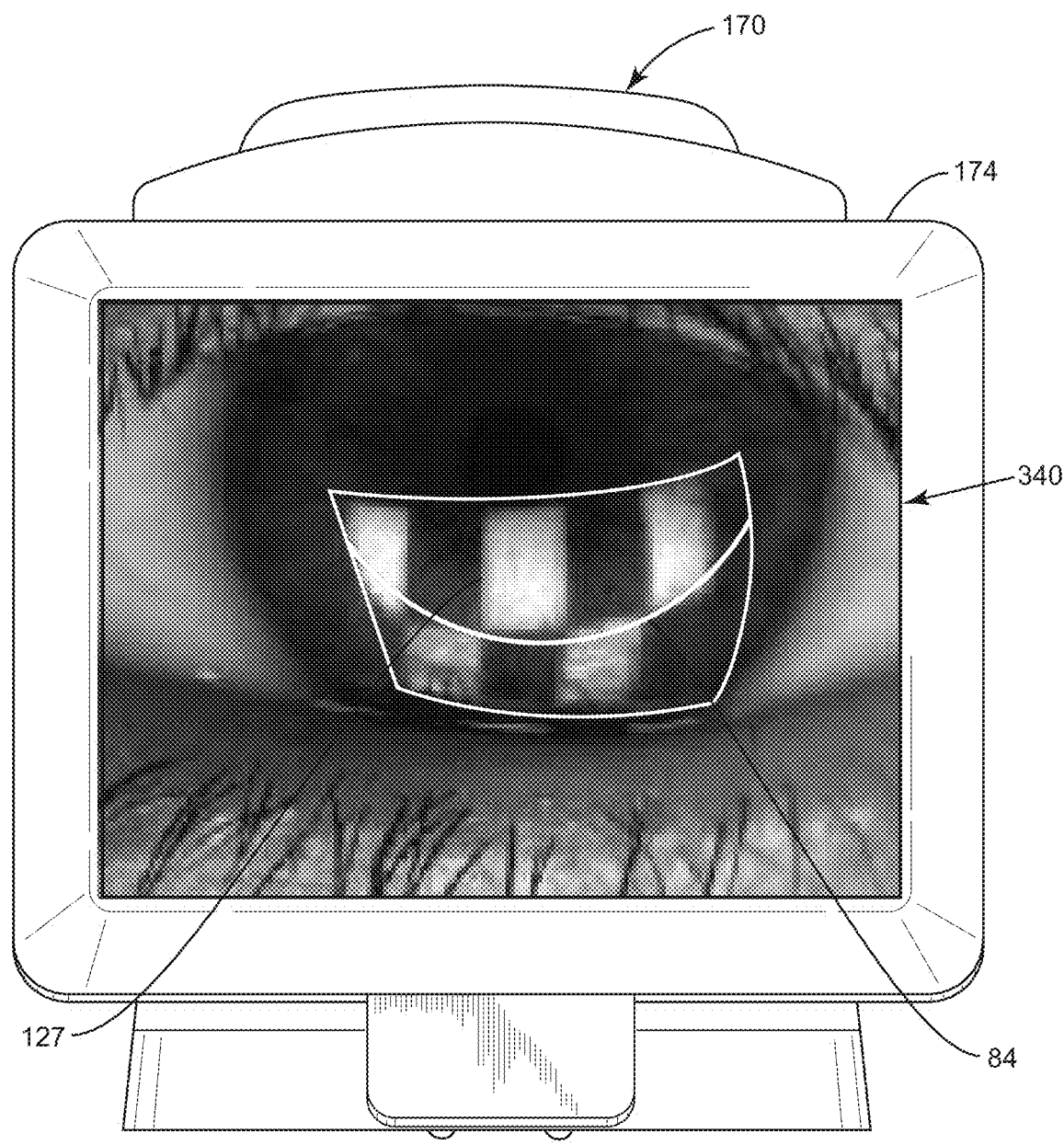
Figure 27C:
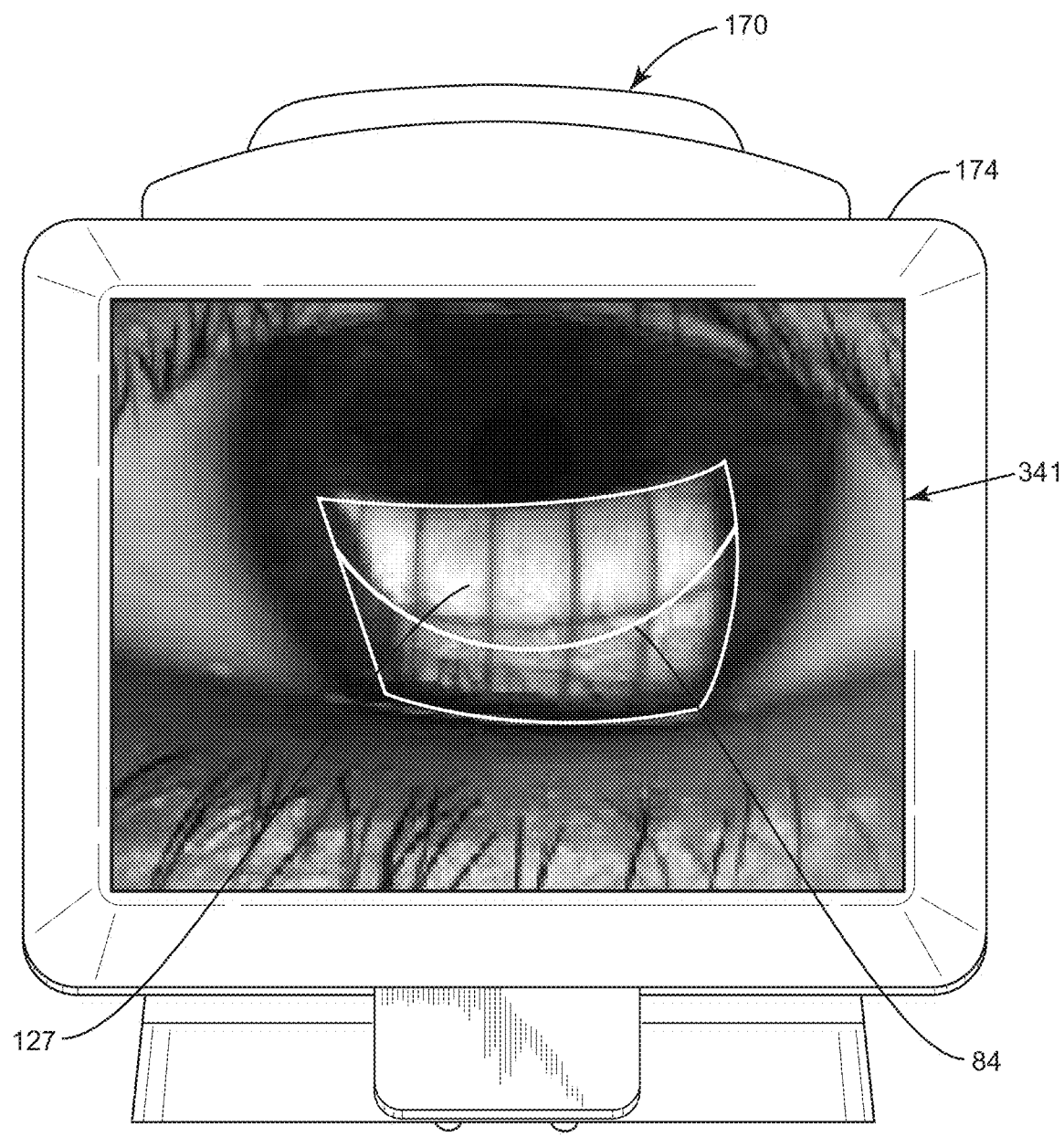

FIGS. 27A-27C illustrate examples of different tear film images that are displayed on the display 174 of the OSI device 170. FIG. 27A illustrates a first image 339 of the patient's tear film showing the tiled pattern captured by the video camera 198. This image is the same image as illustrated in FIG. 11 and previously described above, but processed from a linear output from the video camera 198 to be properly displayed on the display 174. FIG. 27B illustrates a second image 340 of the patient's tear film illustrated in FIG. 12 and previously described above. FIG. 27C illustrates a resulting "overlaid" image 341 of the first and second images 339, 340 of the patient's tear film and to provide interference interactions of the specularly reflected light from the tear film over the entire area or region of interest. This is the same image as illustrated in FIG. 13 and previously described above.

In this example, the original number of frames of the patient's tear film captured can be reduced by half due to the combination of the first and second tiled pattern image(s). Further, if frames in the subtracted image frames capture blinks or erratic movements, and these frames are eliminated in pre-processing, a further reduction in frames will occur during pre-processing from the number of images raw captured in images of the patient's tear film. Although these frames are eliminated from being further processed, they can be retained for visualization rendering a realistic and natural video playback. Further, by applying a thresholding function and erode and dilating functions, the number of non-black pixels which contain TFLT interference information is substantially reduced as well. Thus, the amount of pixel information that is processed by the post-processing system 262 is reduced, and may be on the order of 70% less information to process than the raw image capture information, thereby pre-filtering for the desired interference ROI and reducing or elimination potentially erroneous information as well as allowing for faster analysis due to the reduction in information.

At this point, the resulting images of the tear film have been pre-processed by the pre-processing system 260 according to whatever pre-processing settings 264 and pre-processing steps have been selected or implemented by the computer control system 240. The resulting images of the tear film are ready to be processed for determining tear film characteristics of a contact lens wearer patient, including the process described above in FIG. 6 and other exemplary processes described below. An embodiment of the post-processing performed by the post-processing system 262 is illustrated in the flowchart of FIG. 28.

Tear Film Interference Models

Figure 28:
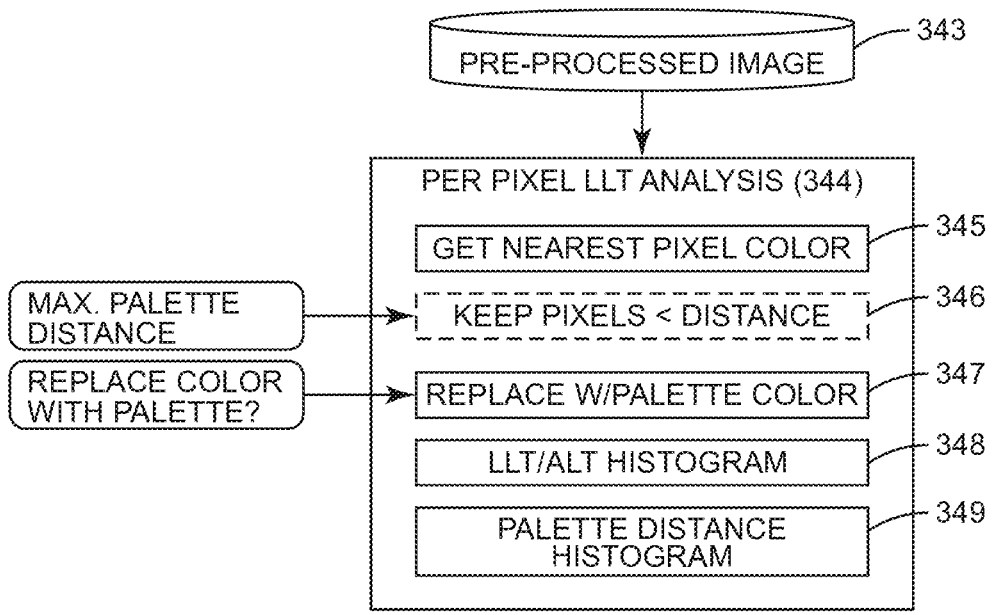
FIG. 28 illustrates an exemplary post-processing system that may be provided in the OSI device of FIG. 14.

As illustrated in FIG. 28, pre-processed images 343 of the resulting images of the tear film are retrieved from RAM 258 where they were previously stored by the pre-processing system 260. Before discussing the particular embodiment of the post-processing system 262 in FIG. 28, in general, to determining tear film characteristics of a contact lens wearer patient, the RGB color values of the pixels in the resulting images of the tear film are compared against color values stored in a lipid layer—contact lens layer interference model that has been previously loaded into the OSI device 170 (see FIG. 25). The lipid layer—contact lens layer interference model is based on a tear film interference model, but altered with an index of refraction of an expected or specific contact lens used in place of the aqueous layer. The lipid layer—contact lens layer interference model and/or a tear film interference model may be stored as a TFLT palette 333 containing RGB values representing interference colors for given LLTs and/or ALTs. The TFLT palette contains interference color values that represent TFLTs based on a theoretical tear film interference model in this embodiment. Depending on the TFLT palette provided, the interference color values represented therein may represent LLTs, ALTs, or both. An estimation of TFLT for each ROI pixel is based on this comparison. This estimate of TFLT is then provided to the clinician via the display 174 and/or recorded in memory to assist in diagnosing DES.

Before discussing embodiments of how the TFLTs as one type of tear film characteristic are estimated from the pre-processed resulting image colored interference interactions resulting from specularly reflected light from the tear film, tear film interference modeling is first discussed. Tear film interference modeling can be used to determine an interference color value for a given TFLT to measure TFLT, which can include both LLT and/or ALT.

Although the interference signals representing specularly reflected light from the tear film are influenced by all layers in the tear film, the analysis of interference interactions due to the specularly reflected light can be analyzed under a 2-wave tear film model (i.e., two reflections) to measure LLT. A 2-wave tear film model is based on a first light wave(s) specularly reflecting from the air-to-lipid layer transition of a tear film and a second light wave specularly reflecting from the lipid layer-to-aqueous layer transition of the tear film. In the 2-wave model, the aqueous layer is effective ignored and treated to be of infinite thickness. To measure LLT using a 2-wave model, a 2-wave tear film model was developed wherein the light source and lipid layers of varying thicknesses were modeled mathematically. To model the tear-film interference portion, commercially available software, such as that available by FilmStar and Zemax as examples, allows image simulation of thin films for modeling. Relevant effects that can be considered in the simulation include refraction, reflection, phase difference, polarization, angle of incidence, and refractive index wavelength dispersion. For example, a lipid layer could be modeled as having an index of refraction of 1.48 or as a fused silica substrate ($SiO_2$) having a 1.46 index of refraction. A back material, such as Magnesium Flouride ($MgF_2$) having an index of refraction of 1.38 may be used to provide a 2-wave model of air/$SiO_2$/$MgF_2$ (1.0/1.46/1.38) for a tear film interference model or the index of refraction of a contact lens in place of 1.38. To obtain more accurate modeling results, the model can include the refractive index and wavelength dispersion values of biological lipid material and biological aqueous material, found from the literature, thus to provide a precise two-wave model of air/lipid/aqueous layers. Thus, a 2-wave tear film interference model allows measurement of LLT regardless of ALT.

Simulations can be mathematically performed by varying the LLT between 10 to 300 nm. As a second step, the RGB color values of the resulting interference signals from the modeled light source causing the modeled lipid layer to specularly reflected light and received by the modeled camera were determined for each of the modeled LLT. These RGB color values representing interference interactions in specularly reflected light from the modeled tear film were used to form a 2-wave model LLT palette, wherein each RGB color value is assigned a different LLT. The resulting subtracted image of the first and second images from the patient's tear film containing interference signals representing specularly reflected light are compared to the RGB color values in the 2-wave model LLT palette to measure LLT.

In another embodiment, a 3-wave tear film interference model may be employed to estimate LLT. A 3-wave tear film interference model does not assume that the aqueous layer is infinite in thickness. In an actual patient's tear film, the aqueous layer is not infinite. The 3-wave tear film interference model is based on both the first and second reflected light waves of the 2-wave model and additionally light wave(s) specularly reflecting from the aqueous-to-mucin layer and/or cornea transitions. Thus, a 3-wave tear film interference model recognizes the contribution of specularly reflected light from the aqueous-to-mucin layer and/or cornea transition that the 2-wave tear film interference model does not. To estimate LLT using a 3-wave tear film interference model, a 3-wave tear film model was previously constructed wherein the light source and a tear film of varying lipid and aqueous layer thicknesses were mathematically modeled. For example, a lipid layer could be mathematically modeled as a material having an index of refraction of 1.48 or as fused silica substrate ($SiO_2$), which has a 1.46 index of refraction. Different thicknesses of the lipid layer can be simulated. A fixed thickness aqueous layer (e.g., >=2 µm) could be mathematically modeled as Magnesium Flouride ($MgF_2$) having an index of refraction of 1.38, or for a lipid layer—contact lens layer interference model, an index of refraction for a contact lens. A biological cornea could be mathematically modeled as fused silica with no dispersion, thereby resulting in a 3-wave model of air/$SiO_2$/$MgF_2$/$SiO_2$ (i.e., 1.0/1.46/1.38/1.46 with no dispersion). As before, accurate results are obtained if the model can include the refractive index and wavelength dispersion values of biological lipid material, biological aqueous material, and cornea tissue, found from the literature, thus to provide a precise two-wave model of air/lipid/aqueous/cornea layers. The resulting interference interactions of specularly reflected light from the various LLT values and with a fixed ALT value are recorded in the model and, when combined with modeling of the light source and the camera, will be used to compare against interference from specularly reflected light from an actual tear film to measure LLT and/or ALT.

In another embodiment of the OSI device 170 and the post-processing system 262 in particular, a 3-wave tear film interference model is employed to estimate both LLT and ALT. In this regard, instead of providing either a 2-wave theoretical tear film interference model that assumes an infinite aqueous layer thickness or a 3-wave model that assumes a fixed or minimum aqueous layer thickness (e.g., ≥2 µm), a 3-wave theoretical tear film interference model is developed that provides variances in both LLT and ALT in the mathematical model of the tear film. Again, the lipid layer in the tear film model could be modeled mathematically as a material having an index of refraction of 1.48 or as fused silica substrate ($SiO_2$) having a 1.46 index of refraction. The aqueous layer could be modeled mathematically as Magnesium Flouride ($MgF_2$) having an index of refraction of 1.38, or an index of refraction of a contact lens for a lipid layer—contact lens layer interference model. A biological cornea could be modeled as fused silica with no dispersion, thereby resulting in a 3-wave model of air/$SiO_2$/$MgF_2$/$SiO_2$ (no dispersion). Once again, the most accurate results are obtained if the model can include the refractive index and wavelength dispersion values of biological lipid material, biological aqueous material, and cornea tissue, found from the literature, thus to provide a precise two-wave model of air/lipid/aqueous/cornea layers. Thus, a two-dimensional (2D) TFLT palette 430 (FIG. 29A) is produced for analysis of interference interactions from specularly reflected light from the tear film. One dimension of the TFLT palette 430 represents a range of RGB color values each representing a given theoretical LLT calculated by mathematically modeling the light source and the camera and calculating the interference interactions from specularly reflected light from the tear film model for each variation in LLT 434 in the tear film interference model. A second dimension of the TFLT palette 430 represents ALT also calculated by mathematically modeling the light source and the camera and calculating the interference interactions from specularly reflected light from the tear film interference model for each variation in ALT 432 at each LLT value 434 in the tear film interference model.

Post-Processing/TFLT Measurement

Figure 29A:
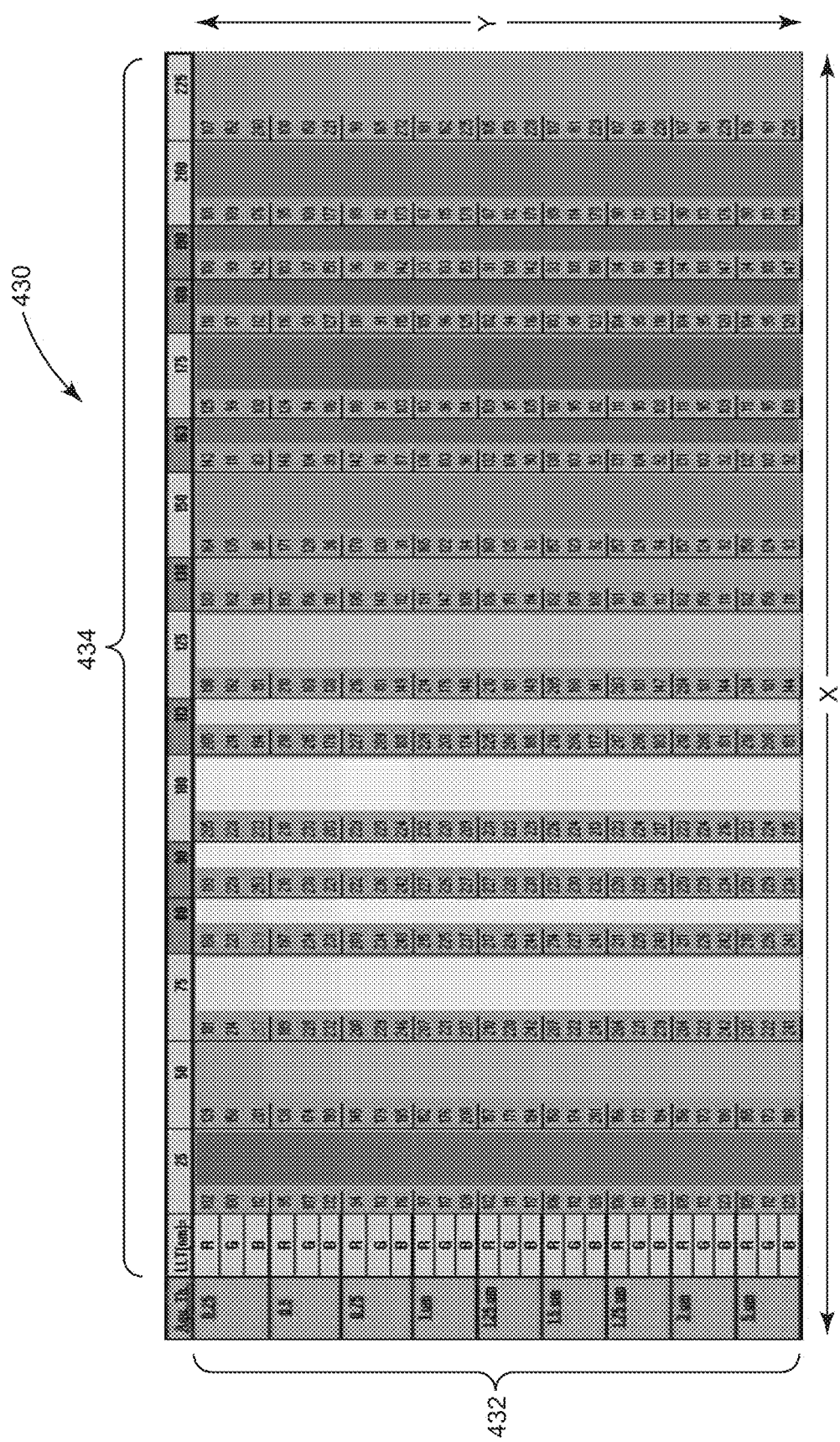
FIG. 29A illustrates an exemplary 3-wave tear film interference model based on a 3-wave theoretical tear film model to correlate different observed interference color with different lipid layer thicknesses (LLTs) and aqueous layer thicknesses (ALTs)
Figure 29B:
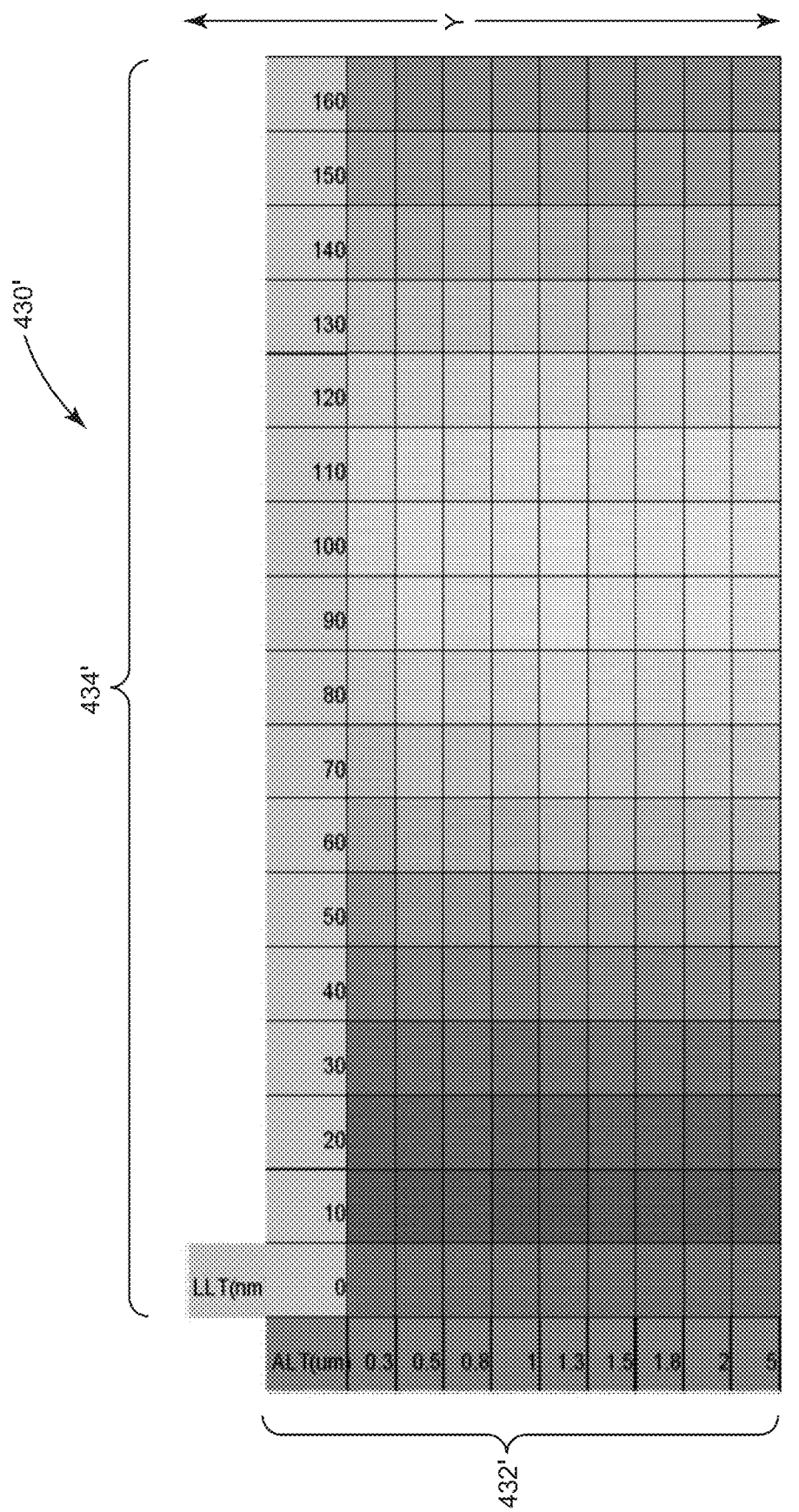
FIG. 29B illustrates another exemplary 3-wave tear film interference model based on a 3-wave theoretical tear film model to correlate different observed interference color with different lipid layer thicknesses (LLTs) and aqueous layer thicknesses (ALTs)

To measure TFLT, a spectral analysis of the resulting interference signal or image is performed during post-processing to calculate a TFLT. In one embodiment, the spectral analysis is performed by performing a look-up in a tear film interference model to compare one or more interference interactions present in the resulting interference signal representing specularly reflected light from the tear film to the RGB color values in the tear film interference model. In this regard, FIGS. 29A and 29B illustrate two examples of palette models for use in post-processing of the resulting image having interference interactions from specularly reflected light from the tear film using a 3-wave theoretical tear film interference model developed using a 3-wave theoretical tear film model, but such could also be used as a theoretical lipid layer—contact lens layer model if adjusted using an index of refraction of a contact lens. In general, an RGB numerical value color scheme is employed in this embodiment, wherein the RGB value of a given pixel from a resulting pre-processed tear film image of a patient is compared to RGB values in the 3-wave tear film interference model representing color values for various LLTs and ALTs in a 3-wave modeled theoretical tear film. The closest matching RGB color is used to determine the LLT and/or ALT for each pixel in the resulting signal or image. All pixels for a given resulting frame containing the resulting interference signal are analyzed in the same manner on a pixel-by-pixel basis. A histogram of the LLT and ALT occurrences is then developed for all pixels for all frames and the average LLT and ALT determined from the histogram (block 348 in FIG. 28).

FIG. 29A illustrates an exemplary TFLT palette 430 in the form of colors representing the included RGB color values representing interference of specularly reflected light from a 3-wave theoretical tear film model used to compared colors from the resulting image of the patient's tear film to estimate LLT and ALT. FIG. 29B illustrates an alternative example of a TFLT palette 430' in the form of colors representing the included RGB color values representing interference of specularly reflected light from a 3-wave theoretical tear film model used to compare colors from the resulting image of the patient's tear film to estimate LLT and ALT. As illustrated in FIG. 29A, the TFLT palette 430 contains a plurality of hue colors arranged in a series of rows 432 and columns 434. In this example, there are 144 color hue entries in the palette 430, with nine (9) different ALTs and sixteen (16) different LLTs in the illustrated TFLT palette 430, although another embodiment includes thirty (30) different LLTs. Providing any number of LLT and TFLT increments is theoretically possible. The columns 434 in the TFLT palette 430 contain a series of LLTs in ascending order of thickness from left to right. The rows 432 in the TFLT palette 430 contain a series of ALTs in ascending order of thickness from top to bottom. The sixteen (16) LLT increments provided in the columns 434 in the TFLT palette 430 are 25, 50, 75, 80, 90, 100, 113, 125, 138, 150, 163, 175, 180, 190, 200, and 225 nanometers (nm). The nine (9) ALT increments provided in the rows 432 in the TFLT palette 430 are 0.25, 0.5, 0.75, 1.0, 1.25, 1.5, 1.75, 3.0 and 6.0 µm. As another example, as illustrated in FIG. 29B, the LLTs in the columns 434' in the TFLT palette 430' are provided in increments of 10 nm between 0 nm and 160 nm. The nine (9) ALT increments provided in the rows 432' in the TFLT palette 430 are 0.3, 0.5, 0.75, 0.08, 1.0, 1.3, 1.5, 1.8, 2.0 and 5.0 µm.

Figure 30:
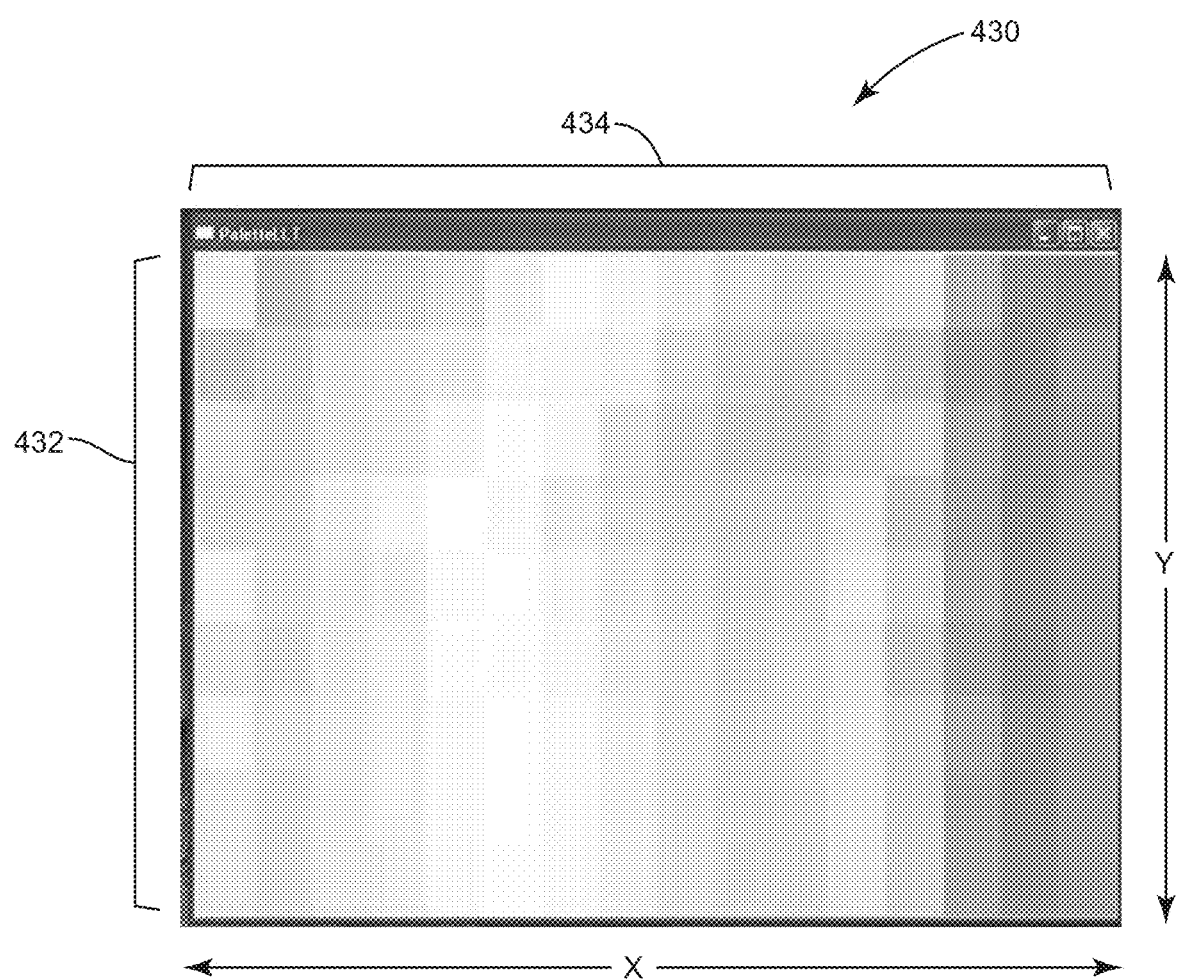
FIG. 30 is another representation of the 3-wave tear film interference model of FIG. 27A and/or FIG. 27B with normalization applied to each red-green-blue (RGB) color value individually.

As part of a per pixel LLT analysis 344 provided in the post-processing system 262 in FIG. 28, for each pixel in each of the pre-processed resulting images of the area or region of interest in the tear film, a closest match determination is made between the RGB color of the pixel to the nearest RGB color in the TFLT palette 430 (block 345 in FIG. 28). The ALTs and LLTs for that pixel are determined by the corresponding ALT thickness in the y-axis of the TFLT palette 430, and the corresponding LLT thickness in the x-axis of the TFLT palette 430. As illustrated in FIGS. 29A and 29B, the TFLT palette 430 colors are actually represented by RGB values. The pixels in each of the pre-processed resulting images of the tear film are also converted and stored as RGB values, although any other color representation can be used as desired, as long as the palette and the image pixel data use the same representational color space. FIG. 30 illustrates the TFLT palette 430 in color pattern form with normalization applied to each red-green-blue (RGB) color value individually. Normalizing a TFLT palette is optional. The TFLT palette 430 in FIG. 30 is displayed using brightness control (i.e., normalization, as previously described) and without the RGB values included, which may be more visually pleasing to a clinician if displayed on the display 174. The GUI utility 280 allows selection of different palettes by selecting a file in the palette file drop down 402, as illustrated in FIG. 20, each palette being specific to the choice of 2-wave vs. 3-wave mode, the chosen source's spectrum, and the chosen camera's RGB spectral responses. To determine the closest pixel color in the TFLT palette 430, a Euclidean distance color difference equation is employed to calculate the distance in color between the RGB value of a pixel from the pre-processed resulting image of the patient's tear film and RGB values in the TFLT palette 430 as follows below, although the present invention is not so limited:

$$\text{Diff.} = \sqrt{((R\text{pixel} - R\text{palette})^{2} + (G\text{pixel} - G\text{palette})^{2} + (B\text{pixel} - B\text{palette})^{2})}$$

Thus, the color difference is calculated for all palette entries in the TFLT palette 430. The corresponding LLT and ALT values are determined from the color hue in the TFLT palette 430 having the least difference from each pixel in each frame of the pre-processed resulting images of the tear film. The results can be stored in RAM 258 or any other convenient storage medium. To prevent pixels without a close match to a color in the TFLT palette 430 from being included in a processed result of LLT and ALT, a setting can be made to discard pixels from the results if the distance between the color of a given pixel is not within the entered acceptable distance of a color value in the TFLT palette 430 (block 346 in FIG. 28).

Figure 31:
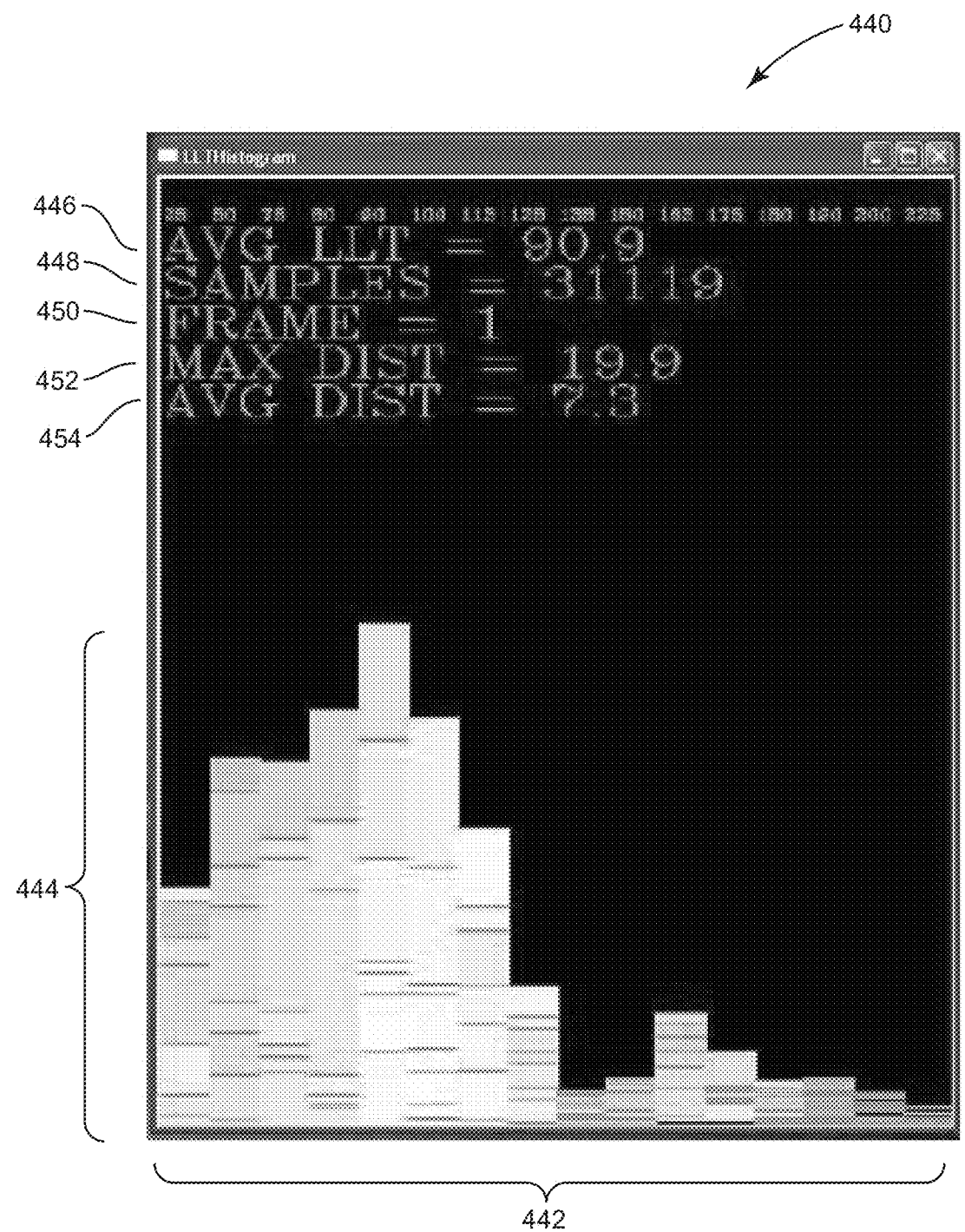
FIG. 31 is an exemplary histogram illustrating results of a comparison of interference interactions from the interference signal of specularly reflected light from a patient's tear film involving contact lens wear to the 3-wave tear film interference model of FIGS. 29A, 29B, and 30 for measuring TFLT of a patient's tear film involving contact lens wear as a tear film characteristic.

Each LLT and ALT determined for each pixel from a comparison in the TFLT palette 430 via the closest matching color that is within a given distance (if that post-processing setting 266 is set) or for all LLT and ALT determined values are then used to build a TFLT histogram. The TFLT histogram is used to determine a weighted average of the LLT and ALT values for each pixel in the resulting image(s) of the patient's tear film to provide an overall estimate of the patient's LLT and ALT. FIG. 31 illustrates an example of such a TFLT histogram 460. This TFLT histogram 440 may be displayed as a result of the shown LLT histogram selection box 400 being selected in the GUI utility 280 of FIG. 20. As illustrated therein, for each pixel within an acceptable distance, the TFLT histogram 440 is built in a stacked fashion with determined ALT values 444 stacked for each determined LLT value 442 (block 349 in FIG. 28). Thus, the TFLT histogram 440 represents LLT and ALT values for each pixel. A horizontal line separates each stacked ALT value 444 within each LLT bar.

Figure 32:
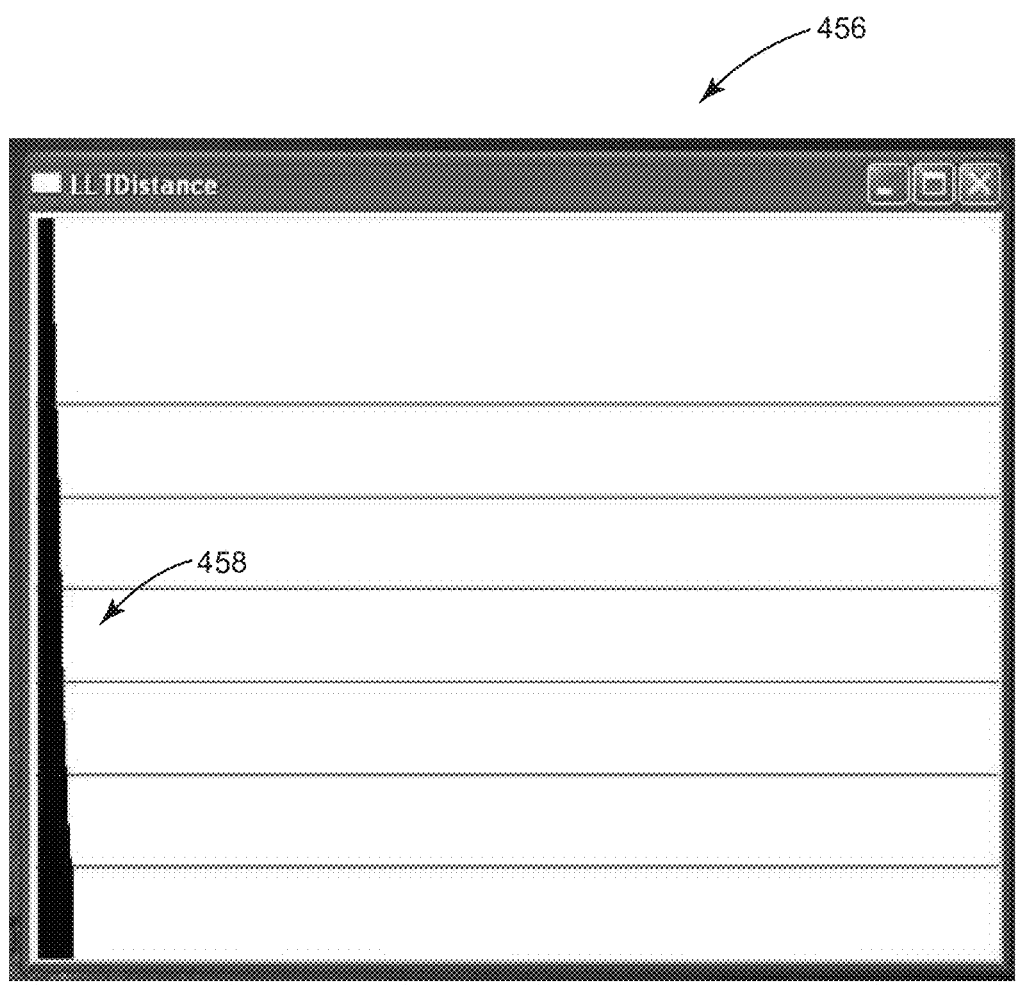
FIG. 32 is an exemplary histogram plot of distances in pixels between RGB color value representation of interference interactions from the interference signal of specularly reflected light from a patient's tear film involving contact lens wear and the nearest distance RGB color value in the 3-wave tear film interference model of FIGS. 29A, 29B, and 30.

One convenient way to determine the final LLT and ALT estimates is with a simple weighted average of the LLT and ALT values 442, 444 in the TFLT histogram 440. In the example of the TFLT histogram 440 in FIG. 31, the average LLT value 446 was determined to be 90.9 nm. The number of samples 448 (i.e., pixels) included in the TFLT histogram 440 was 31,119. The frame number 450 indicates which frame of the resulting video image is being processed, since the TFLT histogram 440 represents a single frame result, or the first of a frame pair in the case of background subtraction. The maximum distance 452 between the color of any given pixel among the 31,119 pixels and a color in the TFLT palette 430 was 19.9, 20 may have been the set limit (Maximum Acceptable Palette Distance) for inclusion of any matches. The average distance 454 between the color of each of the 31,119 pixels and its matching color in the TFLT palette 430 was 7.8. The maximum distance 452 and average distance 454 values provide an indication of how well the color values of the pixels in the interference signal of the specularly reflected light from the patient's tear film match the color values in the TFLT palette 430. The smaller the distance, the closer the matches. The TFLT histogram 440 can be displayed on the display 174 to allow a clinician to review this information graphically as well as numerically. If either the maximum distance 452 or average distance 454 values are too high, this may be an indication that the measured LLT and ALT values may be inaccurate, or that the image normalization is not of the correct value. Further imaging of the patient's eye and tear film, or system recalibration can be performed to attempt to improve the results. Also, a histogram 456 of the LLT distances 458 between the pixels and the colors in the TFLT palette 430 can be displayed as illustrated in FIG. 32 to show the distribution of the distance differences to further assist a clinician in judgment of the results.

Figure 33:
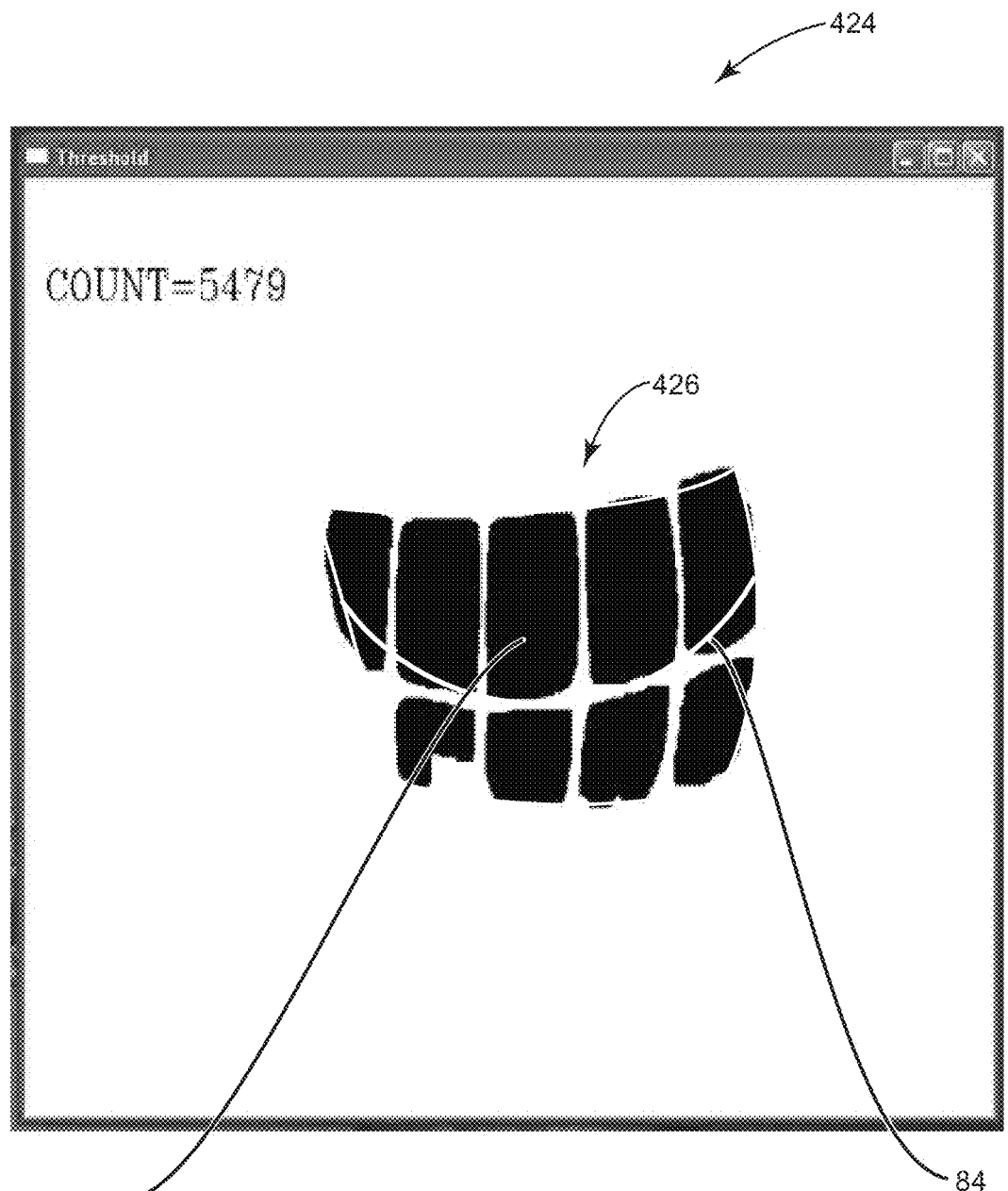
FIG. 33 is an exemplary threshold mask used during pre-processing of the tear film images involving contact lens wear.

Other results can be displayed on the display 174 of the OSI device 170 that may be used by a physician or technician to judge the LLT and/or ALT measurement results. For example, FIG. 33 illustrates a threshold window 424 illustrating a (inverse) threshold mask 426 that was used during pre-processing of the tear film images. In this example, the threshold window 424 was generated as a result of the show threshold window selection box 382 being selected in the GUI utility 280 of FIG. 20. This may be used by a clinician to humanly evaluate whether the threshold mask looks abnormal. If so, this may have caused the LLT and ALT estimates to be inaccurate and may cause the clinician to discard the results and image the patient's tear film again. The maximum distance between the color of any given pixel among the 31,119 pixels and a color in the palette 430 was 19.9 in this example.

Figure 34:
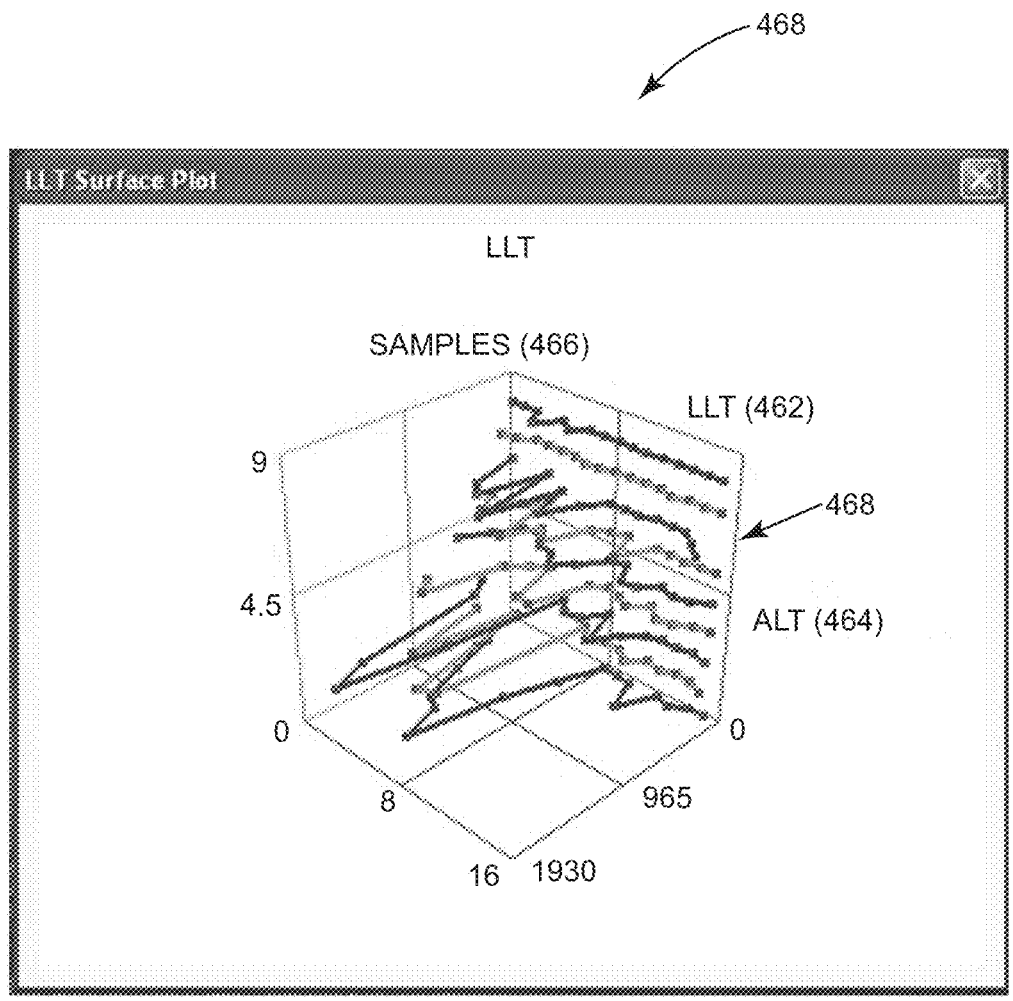
FIG. 34 is an exemplary three-dimensional (3D) surface plot of the measured LLT and ALT thicknesses of a patient's tear film involving contact lens wear.

FIG. 34 illustrates another histogram that may be displayed on the display 174 and may be useful to a clinician. As illustrated therein, a three-dimensional (3D) histogram plot 460 is illustrated. The 3D histogram plot 460 is simply another way to graphically display the fit of the processed pixels from the pre-processed images of the tear film to the TFLT palette 430. The plane defined by the LLT 462 and ALT 464 axes represents the TFLT palette 430. The axis labeled "Samples" 466 is the number of pixels that match a particular color in the TFLT palette 430.

Figure 35:
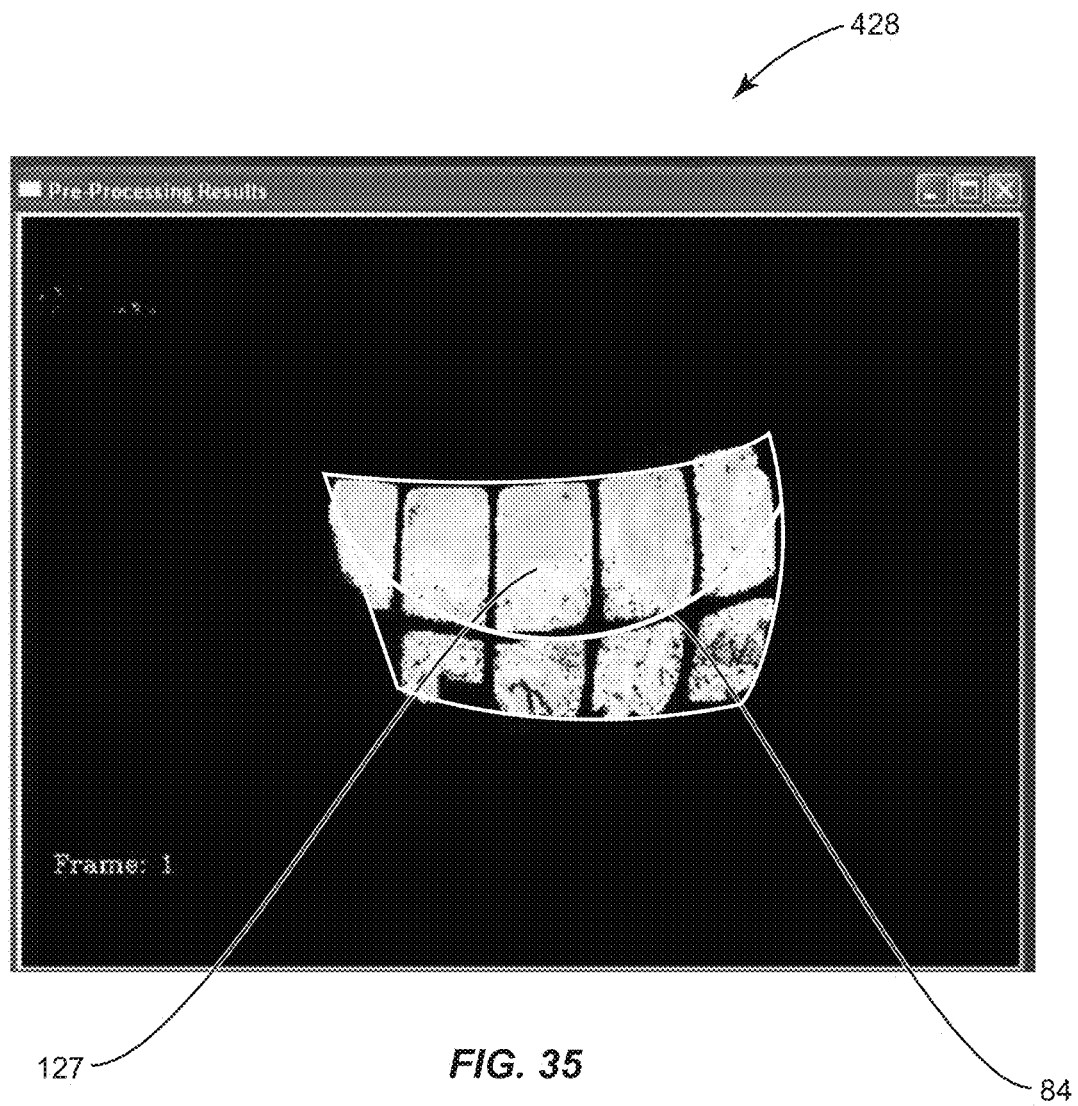
FIG. 35 is an exemplary image representing interference interactions of specularly reflected light from a patient's tear film involving contact lens wear results window based on replacing a pixel in the tear film image with the closest matching RGB color value in the normalized 3-wave tear film interference model of FIG. 30.

FIG. 35 illustrates a result image 428 of the specularly reflected light from a patient's tear film. However, the actual pixel value for a given area on the tear film is replaced with the determined closest matching color value representation in the TFLT palette 430 to a given pixel for that pixel location in the resulting image of the patient's tear film (block 347 in FIG. 28). Visually displaying interference interactions representing the closest matching color value to the interference interactions in the interference signal of the specularly reflected light from a patient's tear film in this manner may be helpful to determine how closely the tear film interference model matches the actual color value representing the resulting image (or pixels in the image).

Ambiguities can arise when calculating the nearest distance between an RGB value of a pixel from a tear film image and RGB values in a TFLT palette, such as TFLT palettes 430 and 430' in FIGS. 29A and 29B as examples. This is because when the theoretical LLT of the TFLT palette is plotted in RGB space for a given ALT in three-dimensional (3D) space, the TFLT palette 469 is a locus that resembles a pretzel like curve, as illustrated with a 2-D representation in the exemplary TFLT palette locus 470 in FIG. 36. Ambiguities can arise when a tear film image RGB pixel value has close matches to the TFLT palette locus 470 at significantly different LLT levels. For example, as illustrated in the TFLT palette locus 470 in FIG. 36, there are three (3) areas of close intersection 472, 474, 476 between RGB values in the TFLT palette locus 470 even though these areas of close intersection 472, 474, 476 represent substantially different LLTs on the TFLT palette locus 470. This is due to the cyclical phenomenon caused by increasing orders of optical wave interference, and in particular, first order versus second order interference for the LLT range in the tear films. Thus, if an RGB value of a tear film image pixel is sufficiently close to two different LLT points in the TFLT palette locus 470, the closest RGB match may be difficult to match. The closest RGB match may be to an incorrect LLT in the TFLT palette locus 470 due to error in the camera and translation of received light to RGB values. Thus, it may be desired to provide further processing when determining the closest RGB value in the TFLT palette locus 470 to RGB values of tear film image pixel values when measuring TFLT.

Figure 36:
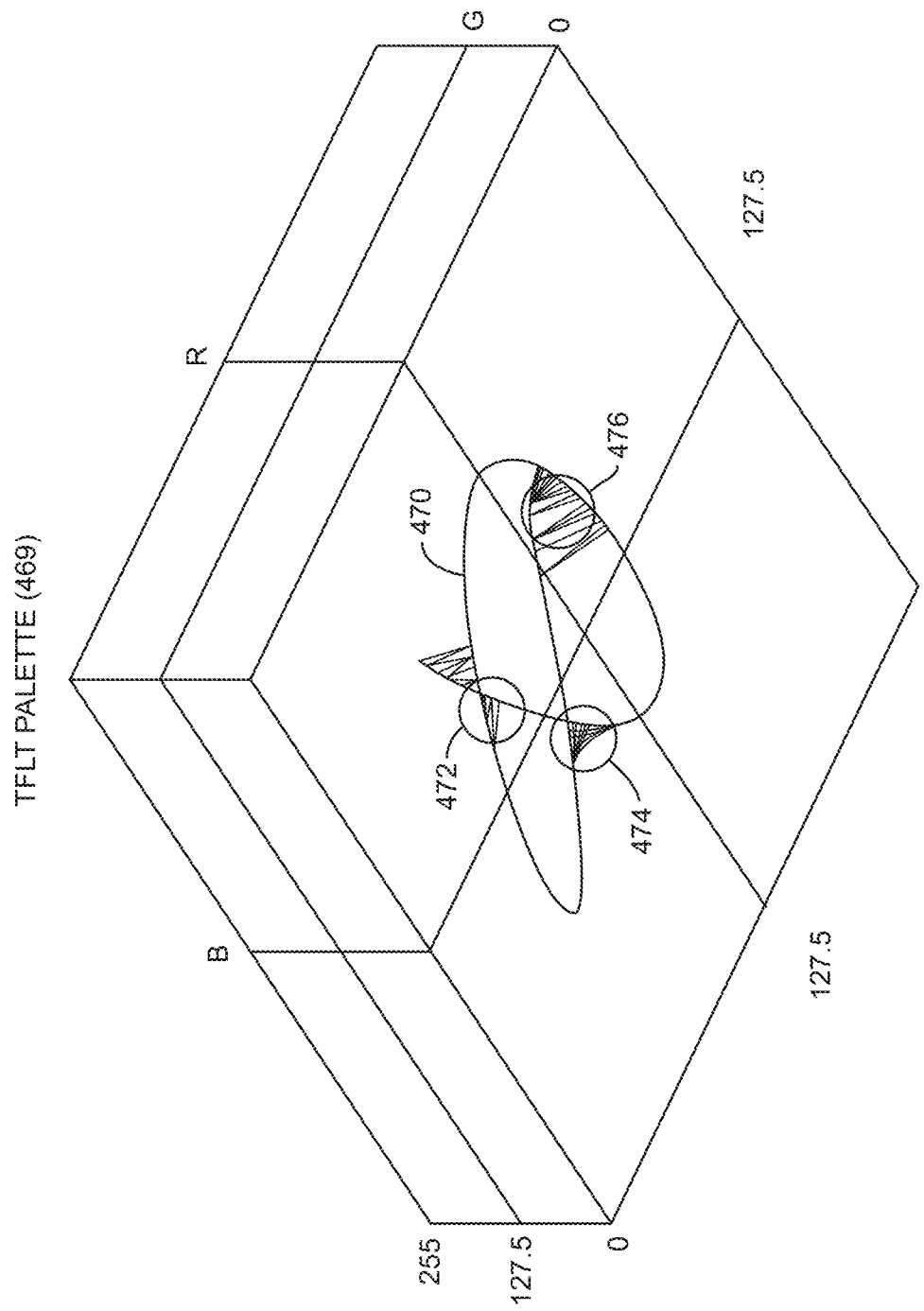
FIG. 36 is an exemplary TFLT palette curve for a TFLT palette of LLTs plotted in RGB space for a given ALT in three-dimensional (3D) space.

In this regard, there are several possibilities that can be employed to avoid ambiguous RGB matches in a TFLT palette. For example, the maximum LLT values in a TFLT palette may be limited. For example, the TFLT palette locus 470 in FIG. 36 includes LLTs between 10 nm and 300 nm. If the TFLT palette locus 470 was limited in LLT range, such as 240 nm as illustrated in the TFLT palette locus 478 in FIG. 37, two areas of close intersection 474 and 476 in the TFLT palette 469 in FIG. 36 are avoided in the TFLT palette 469 of FIG. 37. This restriction of the LLT ranges may be acceptable based on clinical experience since most patients do not exhibit tear film colors above the 240 nm range and dry eye symptoms are more problematic at thinner LLTs. In this scenario, the limited TFLT palette 469 of FIG. 37 would be used as the TFLT palette in the post-processing system 262 in FIG. 28, as an example.

Figure 37:
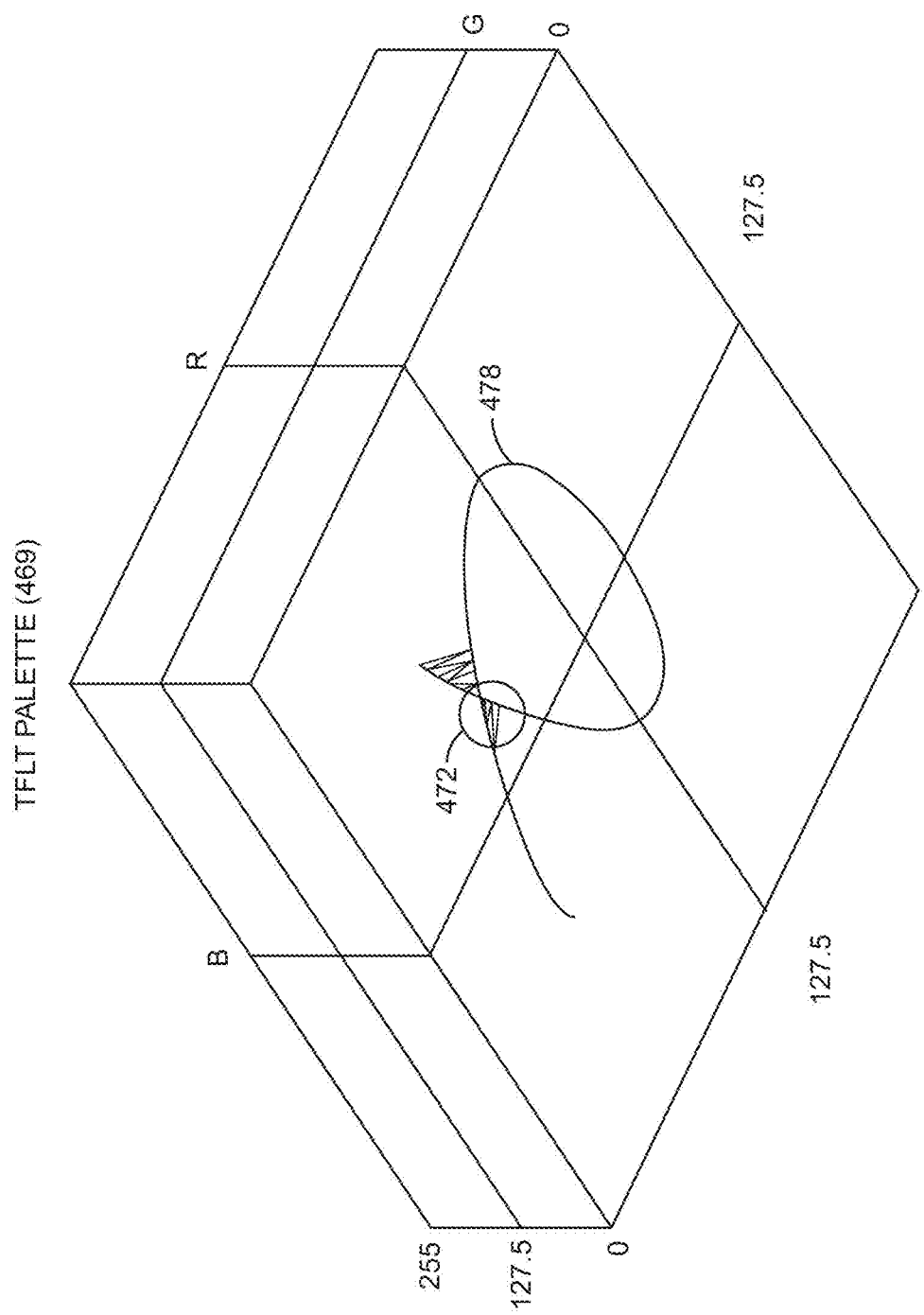
FIG. 37 is an exemplary TFLT palette curve for the TFLT palette of FIG. 36 with LLTs limited to a maximum LLT of 240 nm plotted in RGB space for a given ALT in three-dimensional (3D) space.

Even by eliminating two areas of close intersection 474, 476 in the TFLT palette 469, as illustrated in FIG. 37, the area of close intersection 472 still remains in the TFLT palette locus 478. In this embodiment, the area of close intersection 472 is for LLT values near 20 nm versus 180 nm. In these regions, the maximum distance allowed for a valid RGB match is restricted to a value of about half the distance of the TFLT palette's 469 nearing ambiguity distance. In this regard, RGB values for tear film pixels with match distances exceeding the specified values can be further excluded from the TFLT calculation to avoid tear film pixels having ambiguous corresponding LLT values for a given RGB value to avoid error in TFLT measurement as a result.

Figure 38:
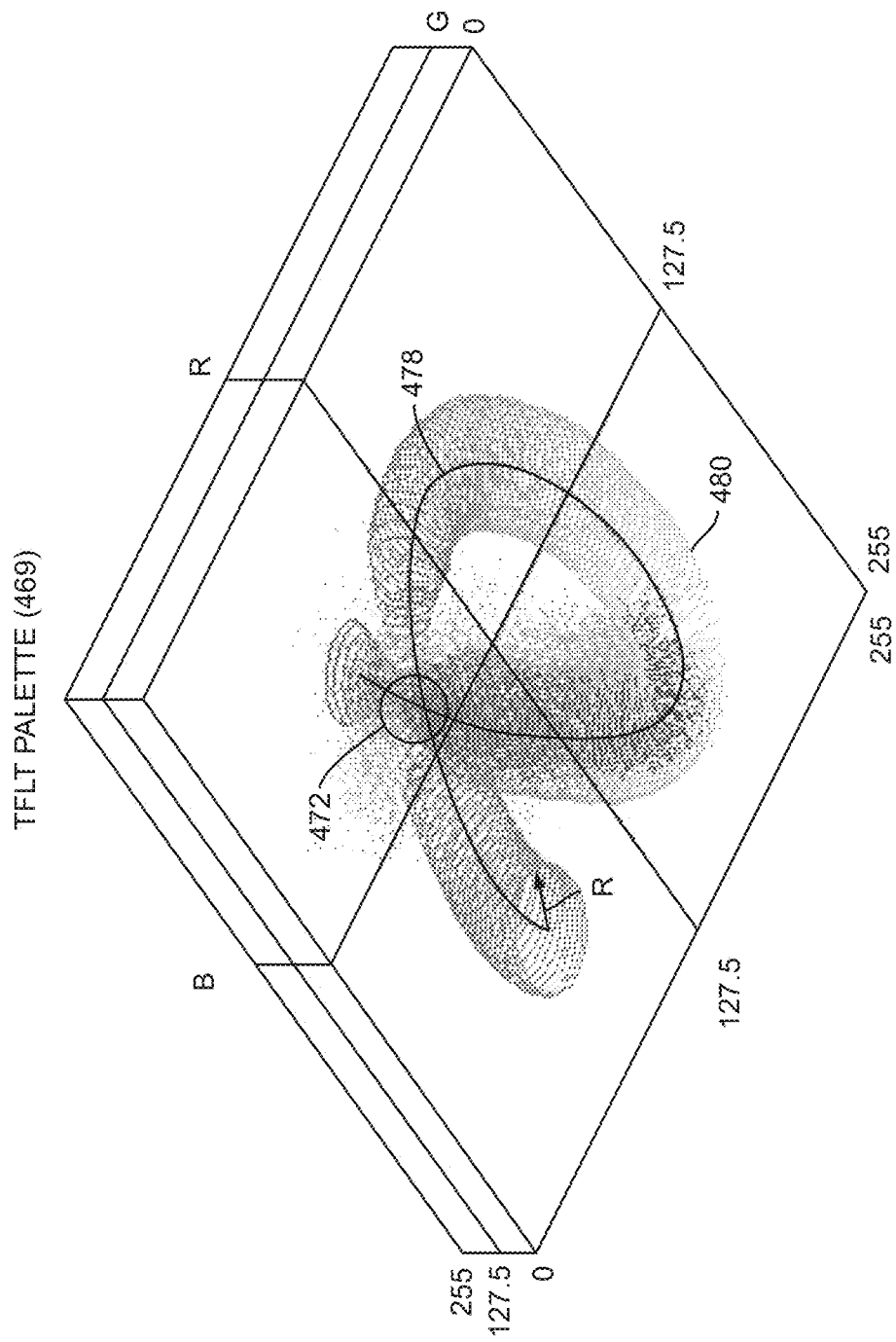
FIG. 38 illustrates the TFLT palette curve of FIG. 37 with an acceptable distance to palette (ADP) filter shown to determine tear film pixel values having RGB values that correspond to ambiguous LLTs.

In this regard, FIG. 38 illustrates the TFLT palette locus 478 in FIG. 37, but with a circle of radius R swept along the path of the TFLT palette locus 478 in a cylinder or pipe 480 of radius R. Radius R is the acceptable distance to palette (ADP), which can be configured in the computer control system 240. When visualized as a swept volume inside the cylinder or pipe 480, RGB values of tear film image pixels that fall within those intersecting volumes may be considered ambiguous and thus not used in calculating TFLT, including the average TFLT. The smaller the ADP is set, the more poorly matching tear film image pixels that may be excluded in TFLT measurement, but less pixels are available for use in calculation of TFLT. The larger the ADP is set, the less tear film image pixels that may be excluded in TFLT measurement, but it is more possible that incorrect LLTs are included in the TFLT measurement. The ADP can be set to any value desired. Thus, the ADP acts effectively as a filter to filter out RGB values for tear film images that are deemed a poor match and those that may be ambiguous according to the ADP setting. This filtering can be included in the post-processing system 262 in FIG. 28, as an example, and in step 346 therein, as an example.

TFT/Blink Stabilization

Figure 39:
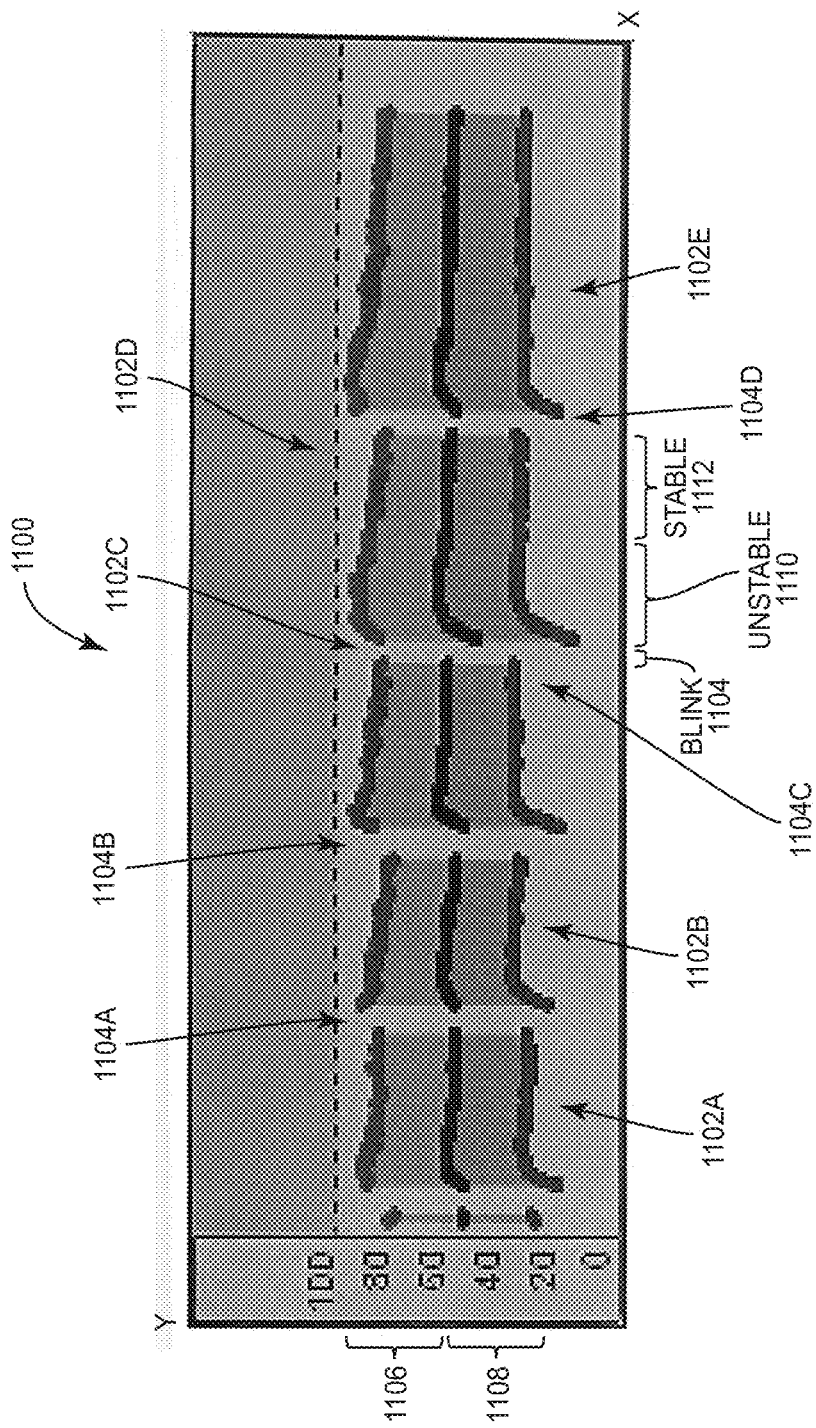
FIG. 39 is an exemplary graph that can be displayed on the display of the OSI device in FIG. 14 representing a patient's tear film movement stabilization during contact lens wear following eye blinks.

A contact lens wearing patient's tear film being stable or unstable between eye blinks can be another tear film characteristic that may be important in determining contact lens intolerance of the patient. For example, regions of the patient's tear film may have high peak LLTs during the course of an interblink, but it may be desired to know if these LLTs are present during short or longer periods of time on a patient's tear film during blinks. In other words, it may be desired to know how stable or unstable a patient's tear film is over an interblink period. In this regard, FIG. 39 is an exemplary tear film stabilization graph 1100 that can be processed by the computer control system 240, using the contact lens-based region of interest 127 in FIG. 13 for example, and displayed on the display of the OSI device 170 in FIG. 16 to represent a contact lens wearing patient's tear film thickness stabilization between eye blinks. In this regard, the graph 1100 contains two axis. The X-axis is time. The Y-axis is thickness measurements in micrometers (μm). A series of tear film stability images 1102A-1102E are shown, with represent tear film stability of the patient's tear film between blinks 1104A-1104D, which are represented by areas of void where no tear film stability information is present. Each tear film stability image 1102A-1102E contains a lipid layer portion 1106 and aqueous portion 1108 representing LLT and ALT of the patient's tear film over time between blinks, respectively. As illustrated in the legend below tear film stability image 1102D, the blink portion 1104 is a period of time in which tear film information is not present, due to blink removal. The unstable portion 1110 of the tear film stability image 1102D is the period of time between blinks where the LLT and ALT of the patient's tear film is changing significantly and thus is unstable. The stable portion 1112 of the tear film stability image 1102D is the period of time between blinks where the LLT and ALT of the patient's tear film is not changing significantly and thus is stable.

Figure 40:
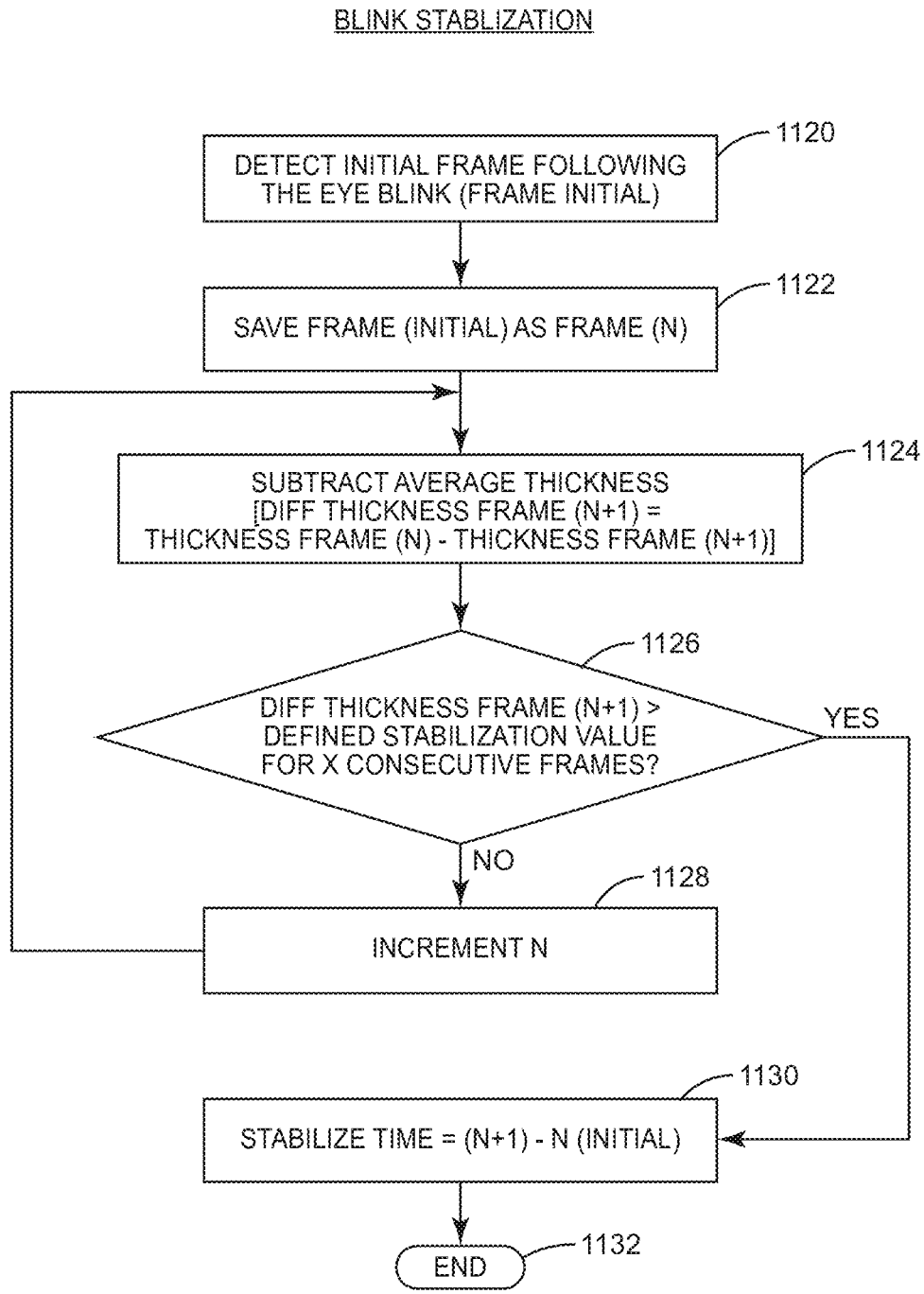
FIG. 40 is a flowchart illustrating an exemplary process for determining a patient's tear film movement during contact lens wear following eye blinks indicative of a patient's tear film thickness stabilization following eye blink during contact lens wear.

FIG. 40 is a flowchart illustrating an exemplary process for determining a movement of a patient's tear film following eye blinks indicative of a contact lens wearer patient's tear film thickness stabilization following eye blink in this example by analyzing the isolated contact-lens based region of interest and processing same using a lipid layer—contact lens layer interference model (e.g., see FIGS. 6 and 127 in FIG. 13). In this regard, the computer control system 240 in the OSI device 170 in FIG. 16 detects an initial frame captured by the video camera 198 of the patient's tear film following a detected eye blink (block 1120). The computer control system 240 saves the initial frame as frame N (block 1122). The computer control system 240 then subtracts the average LLT and ALT between the current frame N and a subsequent frame in a series of captured images of the patient's tear film (block 1124). This difference in average LLT and ALT in the consecutive images is then compared to a predefined stablization value. The computer control system 240 determines if the difference in average LLT and ALT in the consecutive images is greater than the predefined stablization value for a defined number of consecutive frames (block 1126). If not, the computer control system 240 processes the next image in the series of captured images of the patient's tear film before the next blink (blocks 1128-1126). If the computer control system 240 determines the difference in average LLT and ALT in the consecutive images is greater than the predefined stabilization value for a defined number of consecutive frames in block 1126, the computer control system 240 sets the stabilization time of the patient's tear film as the difference between the average LLT and ALT between images in which the difference in average LLT and ALT in consecutive images is greater than the predefined stabilization value (block 1130), and the process ends (block 1132). These stabilization times can be used as stabilization values to be represented in the tear film stabilization graph 1100 in FIG. 40.

Velocity Vector Map

Figure 41:
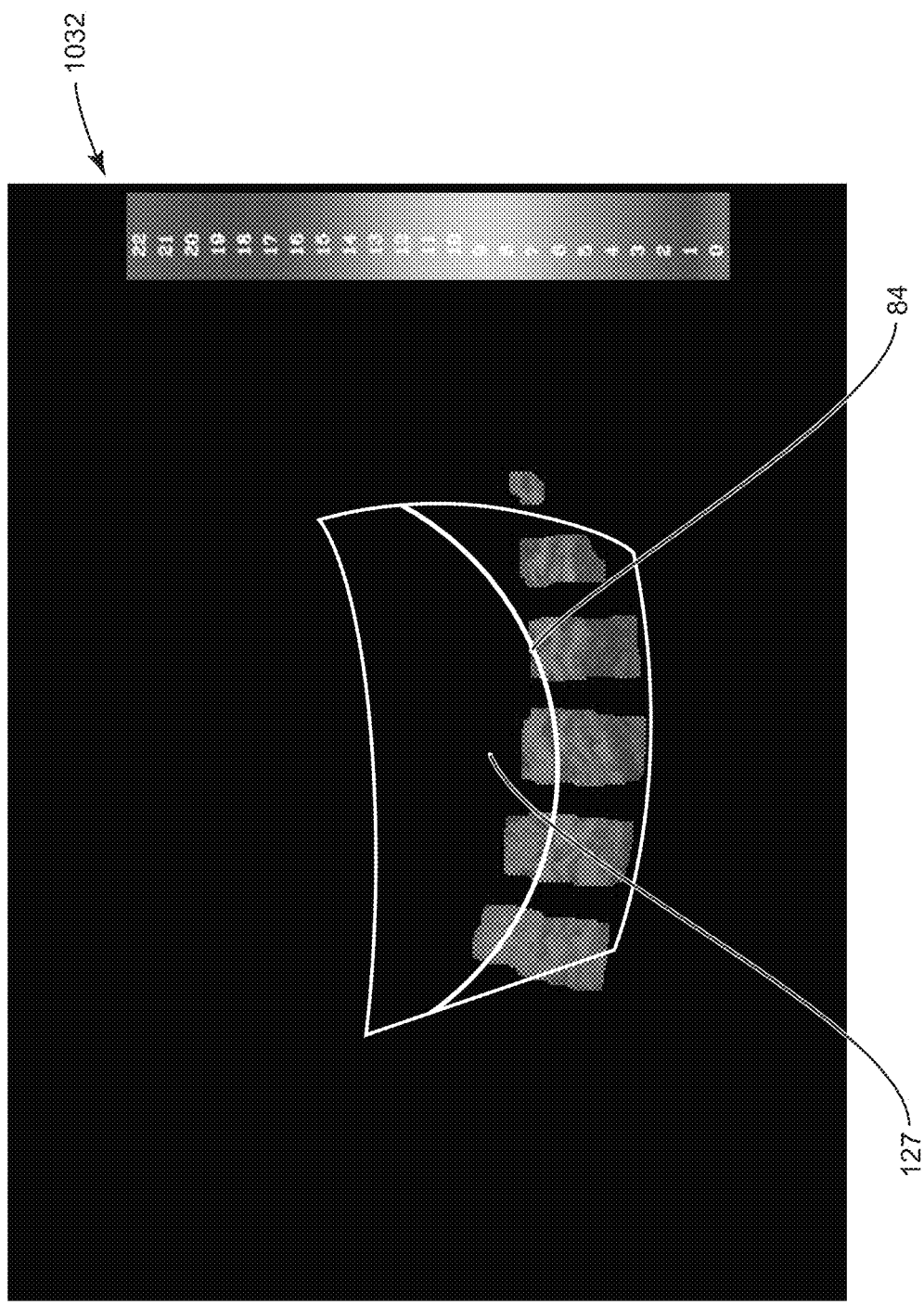
FIG. 41 is an exemplary velocity vector image representing interference interactions of specularly reflected light from a contact lens wearer patient's tear film.

It may also be desired provide a method for a technician to determine the direction of movement of a patient's tear film between eye blinks as another method to determine characteristics of the patient's tear film. The movement of tear film may help characterize the speed, break up, or disappearance of tear film, and the spread, coverage and consistency of TFLT within an area of interest. Understanding the direction of movement of the tear film, including the lipid layer, may assist in understanding how the tear film is distributed across the patient's eye. In this regard, a velocity vector image representing interference interactions of specularly reflected light from a patient's tear film, such as image 1032 in FIG. 41, can be provided, but with additional velocity vector information 1142 superimposed on the image. The velocity vectors show the direction and magnitude of velocity of the patient's tear film over a defined period of time, such as between eye blinks. The length of the velocity vector represents magnitude of velocity. The direction of the velocity vector represents the direction of movement of the patient's tear film over the defined period of time. In other words, the velocity vector information provides a "wind map" of the patient's tear film that can be used to visualize direction and amplitude of movement of the patient's tear film.

Meniscus Height

Other methods may be employed to determine tear film characteristics of a contact lens wearer patient's tear film. Tear film on top of the contact lens 84 can also be analyzed but of particular interest is the tear film build-up on the edge of the contact lens 84. Due to wetting properties and surface tension of tear film, a build-up or meniscus 1150 (shown in FIG. 42) of tear film on the peripheral edge of the contact lens 84 is present. Evaluating the depth, slope, and amount of tear film at this edge surface on the eye surface immediately adjacent the contact lens 84 can provide an indication of tear film quality and quantity throughout the eye and under the contact lens 84. This area of interest becomes a unique measurement, since the tear film will have a nonplanar shape at the edge of the contact lens 84. The density of lipids at this location will indicate how well lubricated with lipids the tear film is and the surface of the eye 11 is directly adjacent to the contact lens 84. These values—thickness, slope, density—can be a predictor of contact lens intolerance.

Figure 1:
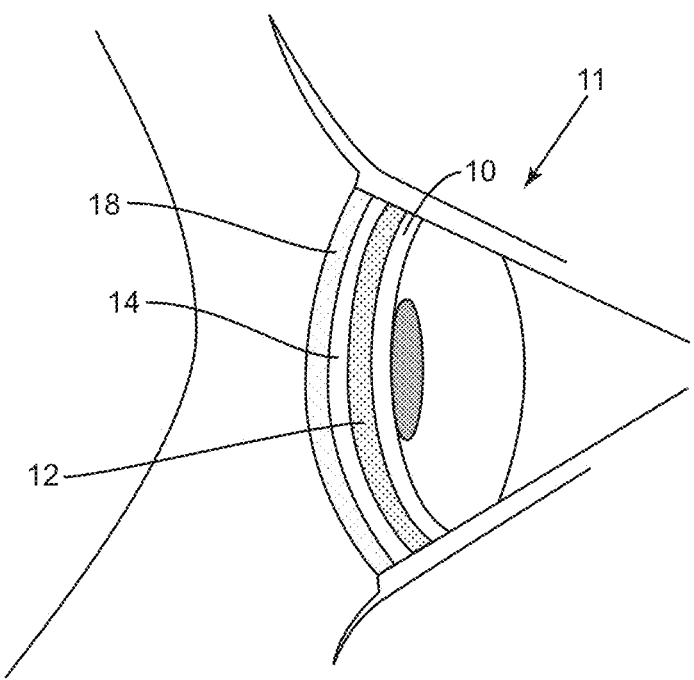
FIG. 1 is a side view of an exemplary eye showing the three layers of the tear film in exaggerated form.
Figure 2A:
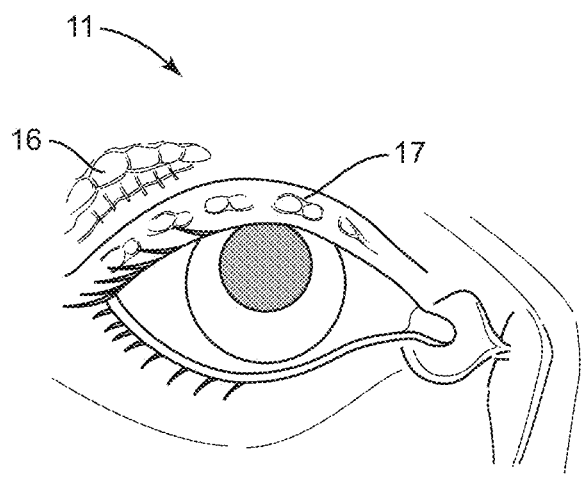
FIG. 2A is a front view of an exemplary eye showing the lacrimal and accessory tear glands that produce aqueous in the eye.
Figure 2B:
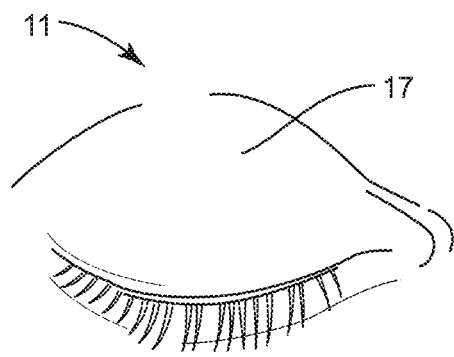
FIG. 2B is a front view of an exemplary eye in FIG. 2A during a blink.
Figure 3:
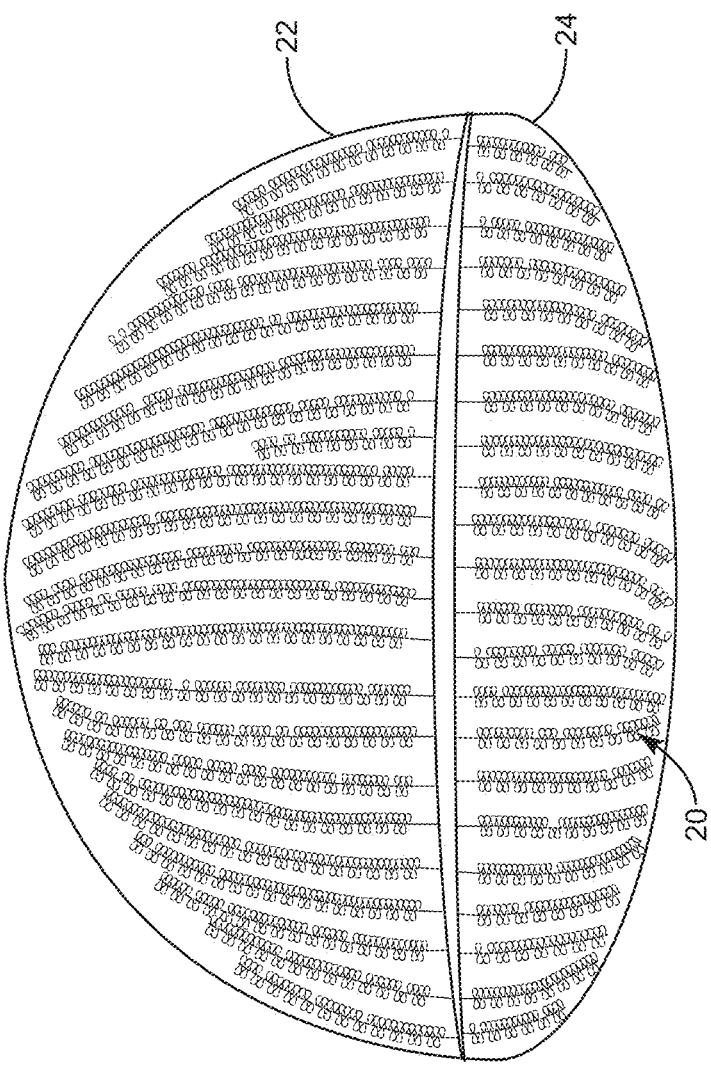
FIG. 3 illustrates exemplary upper and lower eyelids showing the meibomian glands contained therein.
Figure 42:
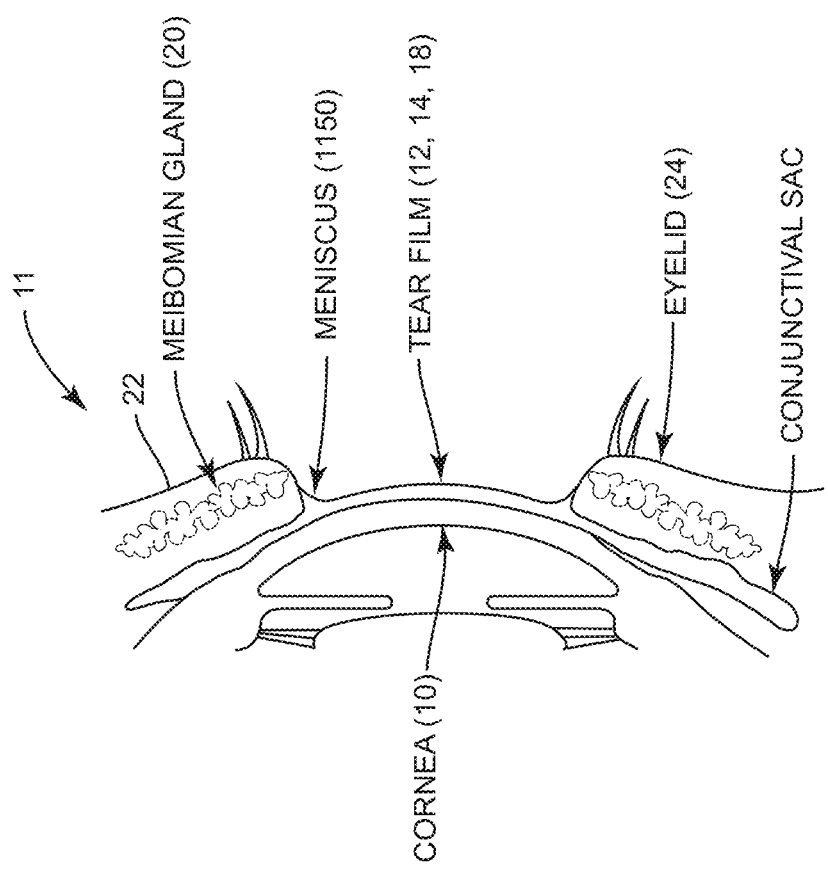
FIG. 42 is a close up side view of a patient's cornea during contact lens wear and a tear film disposed on top of the patient's contact lens, and determining tear film characteristics of the patient's tear film as the slope of the meniscus.

In this regard, the OSI device 170 in FIG. 16 could also be used to measure the height and/or slop of the meniscus of a patient's eye 11 to be used to approximate the ALT of the patient's tear film. For example, FIG. 42 illustrates a side view of a patient's eye 11 in FIGS. 1-3 described above. Common element numbers are shown to include common features. The meniscus 1150 of the eye 11 is shown therein. The video camera 198 of the OSI device 170 in FIG. 16 could be used to image the meniscus 1150. The interference interactions of specularly reflected light from the meniscus 1150 may be correlated to a tear volume, which may be correlated to an ALT of the aqueous layer 14 of the patient's tear film.

In the process described above in FIG. 6 and discussed thereafter, the contact lens-based region of interest of an image of a contact lens wearing patient's tear film was analyzed to determine tear film characteristics indicative of contact lens intolerance. Because the contact lens-based region of interest was analyzed, a lipid layer—contact lens layer interference model was used in examples discussed above since the lipid layer of the patient's tear film was disposed on top of a contact lens, which was thus modeled with its index of refraction as an aqueous layer in the interference model. However, such is not limiting. It may also be desired to analyze the patient's tear film in non-contact lens-based regions of interest to determine tear film characteristics of the patient's tear film during contact lens wear. For example, areas at the interface of the contact lens may be of interest. Further, the patient's tear film could be analyzed in non-contact lens-based regions of interest during contact lens wear and then in the entire regions of interest, including where the contact lens was disposed on the cornea, after the contact lens is removed to determine the difference in tear film characteristics as a result of contact wear and no contact wear.

Figure 43:
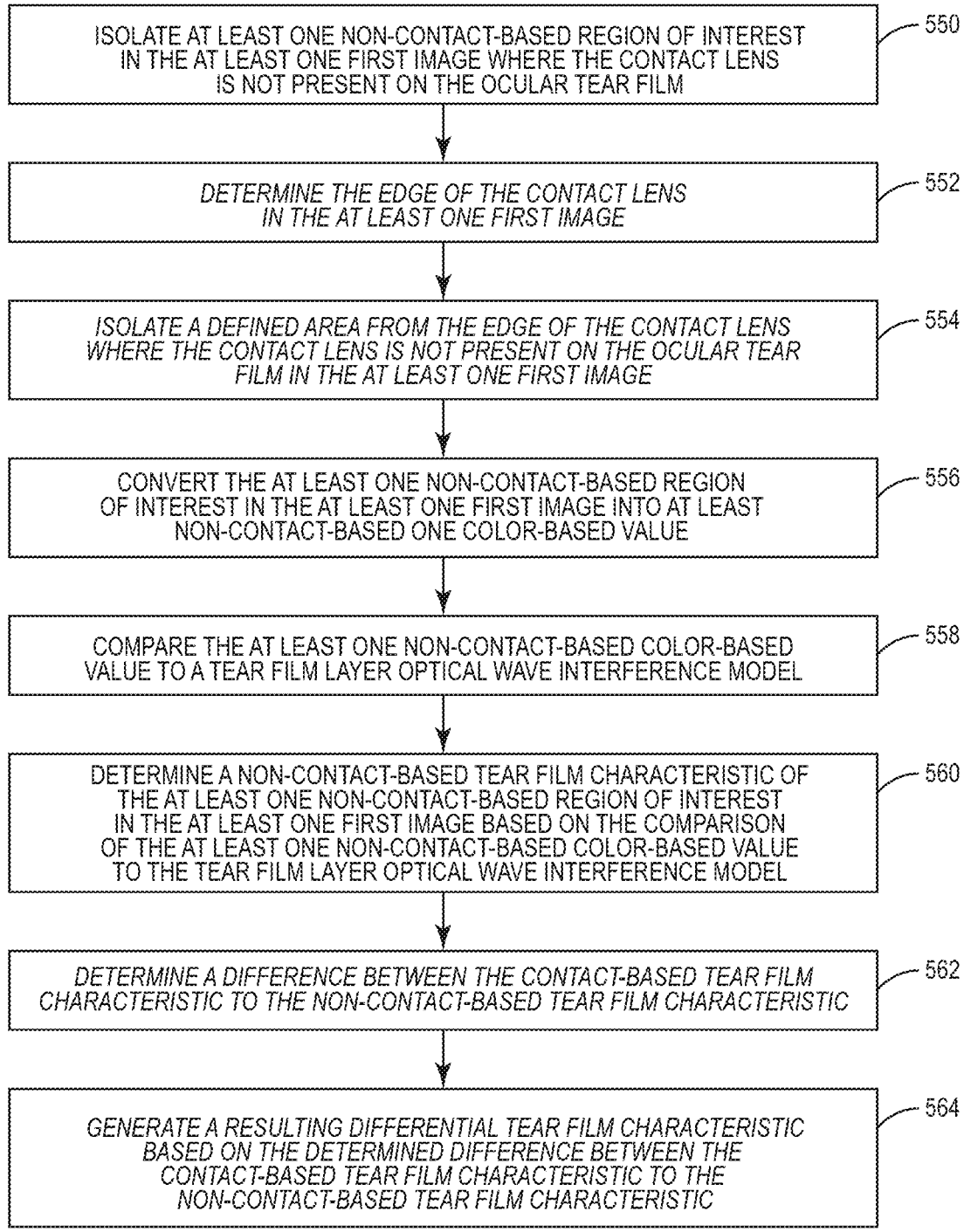
FIG. 43 is a flowchart of an exemplary process for determining tear film characteristics of a patient's ocular tear film based on analysis of imaged optical wave interference of specularly reflected light from a non-contact lens-based region of interest of the patient's tear film during contact lens wear, to determine the patient's intolerance to contact lens wear.

In this regard, FIG. 43 is a flowchart of an exemplary process for determining tear film characteristics of a patient's ocular tear film based on analysis of imaged optical wave interference of specularly reflected light from a non-contact lens-based region of interest of the patient's tear film during contact lens wear, to determine the patient's intolerance to contact lens wear. After the ocular tear film is imaged by the imaging device 40 in the OSI device 30 in FIG. 4A14, the computer control system 240 can isolate a non-contact lens-based region of interest in the first image or resulting image of a contact lens wearing patient's tear film where the contact lens is not present (block 550 in FIG. 43). For example, the computer control system 240 may determine the edge of the contact lens 84 on the ocular tear film to determine the non-contact lens-based regions of interest in the captured image of the ocular tear film (block 552) and isolate the contact lens-based region of interest from the image to be processed (block 554). The edge of the contact lens 84 may be determined, for example, by a user indicating on the GUI 280 of the OSI device 30, where the contact lens appears in the captured image of the patient's tear film during contact wear. Or, the computer control system 240 may analyze the pixels of a captured image(s) from the patient's ocular tear film to find a circular edge pattern therein to determine the location of the contact lens in the capture image.

With continuing reference to FIG. 43, the computer control system 240 can then process the non-contact lens-based region of interest according to any of the processing techniques described above to then convert the non-contact lens-based region of interest to at least one color-based value (block 556). The color-based value can then be compared to a tear film interference model that is not altered based on the index of refraction of a contact lens, as described above (block 558). The computer control system 240 can then determine a tear film characteristic above the non-contact lens-based region of interest of the patient's tear film based on a comparison of the color-based value to the tear film interference model (block 560). As additional optional steps, the patient could be asked to remove their contact lens and another image of the patient's tear film be captured, wherein the difference between the tear film characteristics between the same non-contact lens-based regions of interest in images with contact lens present due to contact lens wear and without a contact lens wear present, be determined (block 562), and a result generated based on the difference for analysis (block 564).

As discussed above, there is a theoretical wavelength that will result from constructive and destructive interference of reflected light from the tear film of a mammalian eye at the point of capture in an imaging device. The theoretical wavelength is based upon factors such as the index of refraction of the lipid layer and the index of refraction of the aqueous layer for a tear film interference model, or a contact lens for a lipid layer—contact lens layer interference model. As a result, there should be theoretical and predictable wavelengths that can then be represented as RGB values in the computer control system. Therefore, the RGB values can be correlated to tear film measurements. However, there may be factors that can cause the theoretical wavelength RGB values to deviate slightly without necessarily invalidating the above described tear film measurement approach, but it might be able to be improved upon. Thus, it may be desirable to provide an optical phantom to mimic or substantially mimic an ocular tear film for calibration purposes. For example, the optical phantoms of the present disclosure are constructed such that light rays emitted from a light source are specularly reflected from the optical phantoms and undergo constructive and destructive optical wave interference interactions that mimic or substantially mimic characteristics of light specularly reflected from ocular tear films. Ideal optical phantoms should be optically equivalent to a biological tear film. The optical phantoms should include two layers, one layer with an index of refraction equal to that of meibomian lipid (1.4770 at 589 nm) on top of a substrate having an index of refraction equal to that of an aqueous layer (1.33698 at 589 nm)

However, attempts to find optical materials with indices of refraction identical to the biological indices have been difficult. No exact matches for the two refractive indices were found. Fortunately, a previously unknown and breakthrough discovery made by the inventors of the present application was that if an optical phantom were manufactured with materials that include the same or substantially the same ratio of indices of refraction as an ocular tear film, the phantom would mimic or substantially mimic the specularly reflective characteristics of an ocular tear film. The materials provided in one example include a coating of magnesium oxide (MgO), which has a refractive index of 1.68 at 589 nm, atop a preferred substrate of silicon optical crown glass, which has a refractive index of 1.517 at 589 nm. The ratio of the indices of refraction is 1.107 for the phantom materials is extremely close to 1.105, which is the ratio between the lipid and aqueous refractive indices.

Using an optical phantom with the same or substantially the same ratio of indices as the lipid and aqueous layers will produce a color palette with the same or substantially the same hue as the biological model, but with a different lightness and chroma. The difference in lightness is caused by a difference in reflection intensity of white light at the air/lipid/aqueous boundary versus the air/optical film/substrate coating boundary. This is easily compensated for by using a neutral density filter 629 (shown in FIG. 44) in the imaging path of the imaging device 194 to reduce the lightness of the incident light. The difference in chroma results from the interference between the recombination of reflected and refracted rays of different magnitudes compared to the biological model. This effect is compensated after the data is acquired.

Even though the thickness of optical coating which provides reflected light of a given hue will be different than the corresponding thickness of meibum that produces light of the same or substantially the same hue, this effect can be readily compensated for by normalizing the lightness and chroma based on the calculated differences between the biological model and the optical phantom. The optical path length is the same or substantially the same for both the phantom and the biological model to ensure that the phase shift is identical and light is modulated proportionately.

The reflected (double pass) optical path length is equal to:

$$\Gamma = 2nt * \cos\left(\sin^{-1}\left(\frac{\sin(\theta_i)}{n}\right)\right)$$

Where $\Gamma$ is the optical path length, n is the index of refraction of the medium, t is the physical thickness of the medium, and $\theta_i$ is the angle of incidence. This assumes the angle of incidence, as measured from the surface normal, is in a medium with index of refraction equal to one.

Figure 44:
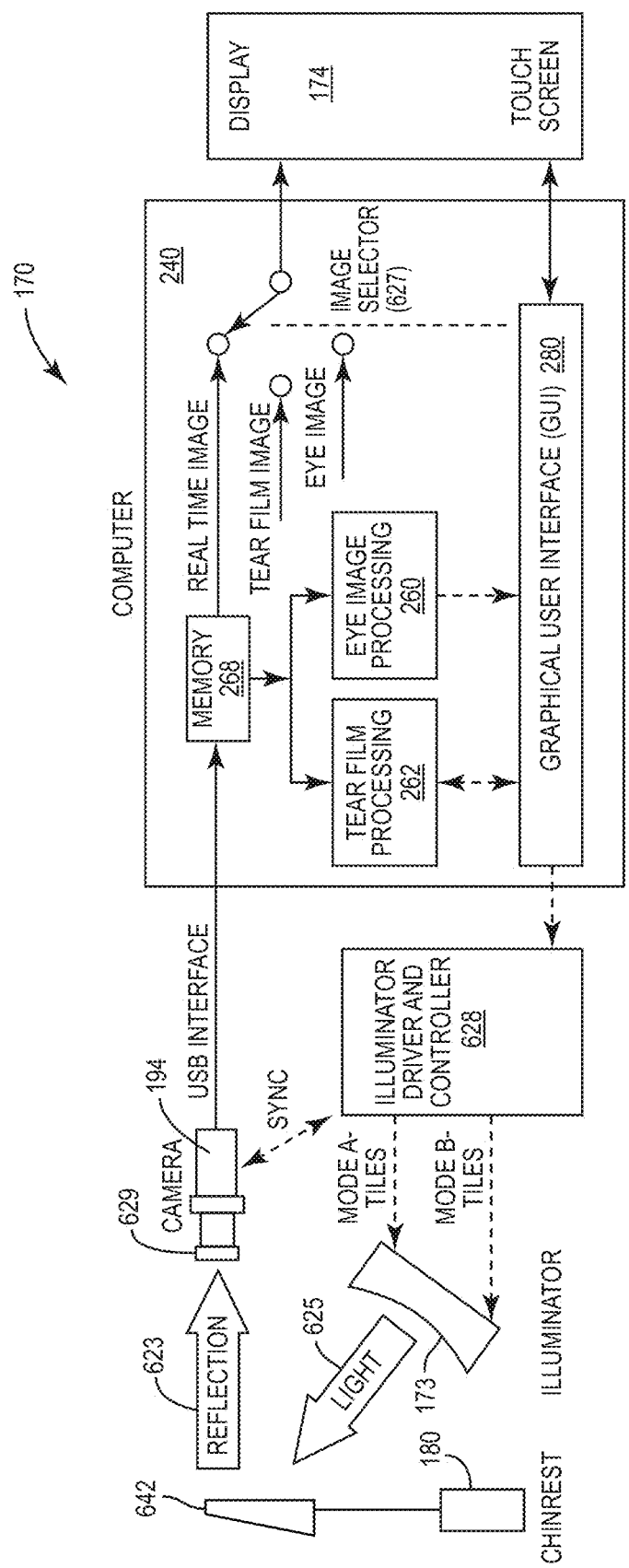
FIG. 44 is a block diagram of the OSI device configured to calibrate the OSI device to make accurate tear film measurements.
Figure 45:
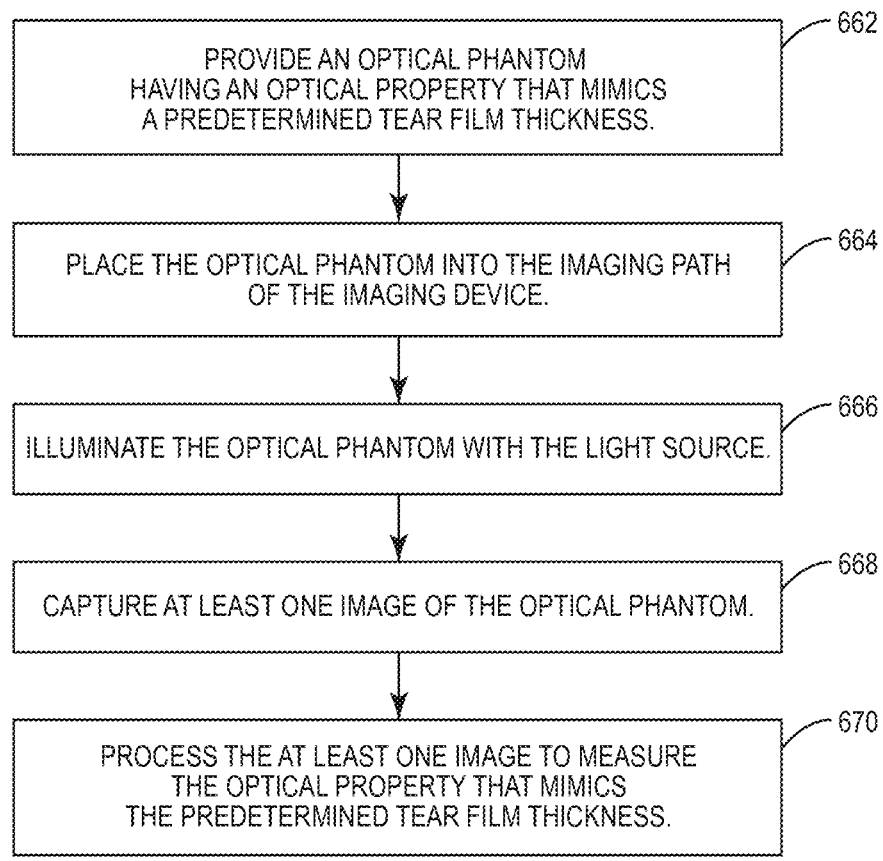
FIG. 45 is a flowchart of an exemplary procedure for calibrating the OSI device to make tear film measurements.

FIG. 44 is a block diagram of the OSI device 170 in FIG. 14, but additionally configured to calibrate the OSI device to make accurate tear film measurements. FIG. 45 is a flowchart of an exemplary procedure for calibrating the OSI device to make tear film measurements. The procedure begins by providing a wedge shaped optical phantom 642 having an optical property that mimics or substantially mimics a predetermined tear film thickness (block 662). Next, the wedge shaped optical phantom 642 is placed within the imaging path of the imaging device 194 (block 664). Then the illuminator 173 (i.e., a light source) is energized to illuminate the wedge shaped optical phantom 642 (block 666). Once the wedge shaped optical phantom 642 is illuminated, the imaging device 194 is commanded via the illuminator driver and controller 628 to capture at least one image of the wedge shaped optical phantom 642 (block 668). The at least one image is then processed by the computer/computer control system 240 to measure the optical property that mimics or substantially mimics the predetermined tear film thickness (block 670). After a desired number of images of the wedge shaped optical phantom 642 is taken, another wedge shaped optical phantom 642 having a different thin film material thickness may be placed in the imaging path of the imaging device 194, and the steps of blocks 664 through 670 are repeated.

Selecting Thicknesses of Optical Phantom Coating

Figure 46:
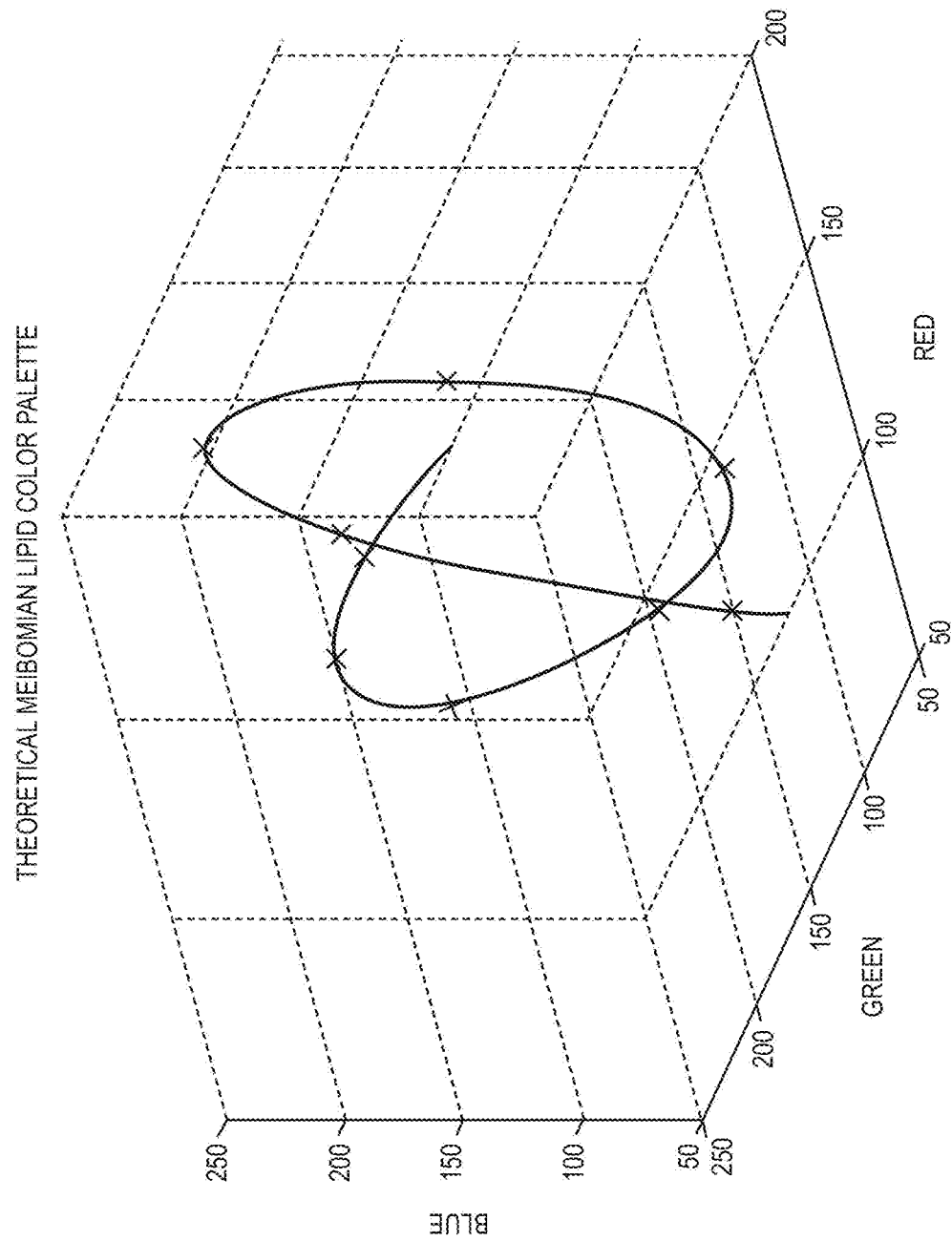
FIG. 46 is an exemplary RGB plot of an exemplary theoretical lipid color palette with points selected for optical phantoms.

FIG. 46 is an exemplary RGB plot of an exemplary theoretical lipid color palette with points selected for phantoms. The palette is plotted for a lipid layer thickness ranging from 10 to 300 nm, for the illuminator 173 and the imaging device 194. The solid curving line shows the color palette predicted by a theoretical analysis given the measured optical parameters of the imaging device 194 and the illuminator 173 and using the lipid and aqueous optical parameters from literature. The cross-markers indicate the targeted LLT points on the palette for which corresponding phantoms were fabricated. These targeted LLT points are selected to encompass the full range of the palette and to quantify the major inflection points along the solid curving line representing the theoretical lipid color palette. The lipid layer thicknesses of the selected points are shown in the table of FIG. 47, along with their corresponding optical pathlengths and phantom thicknesses.

Figure 48:
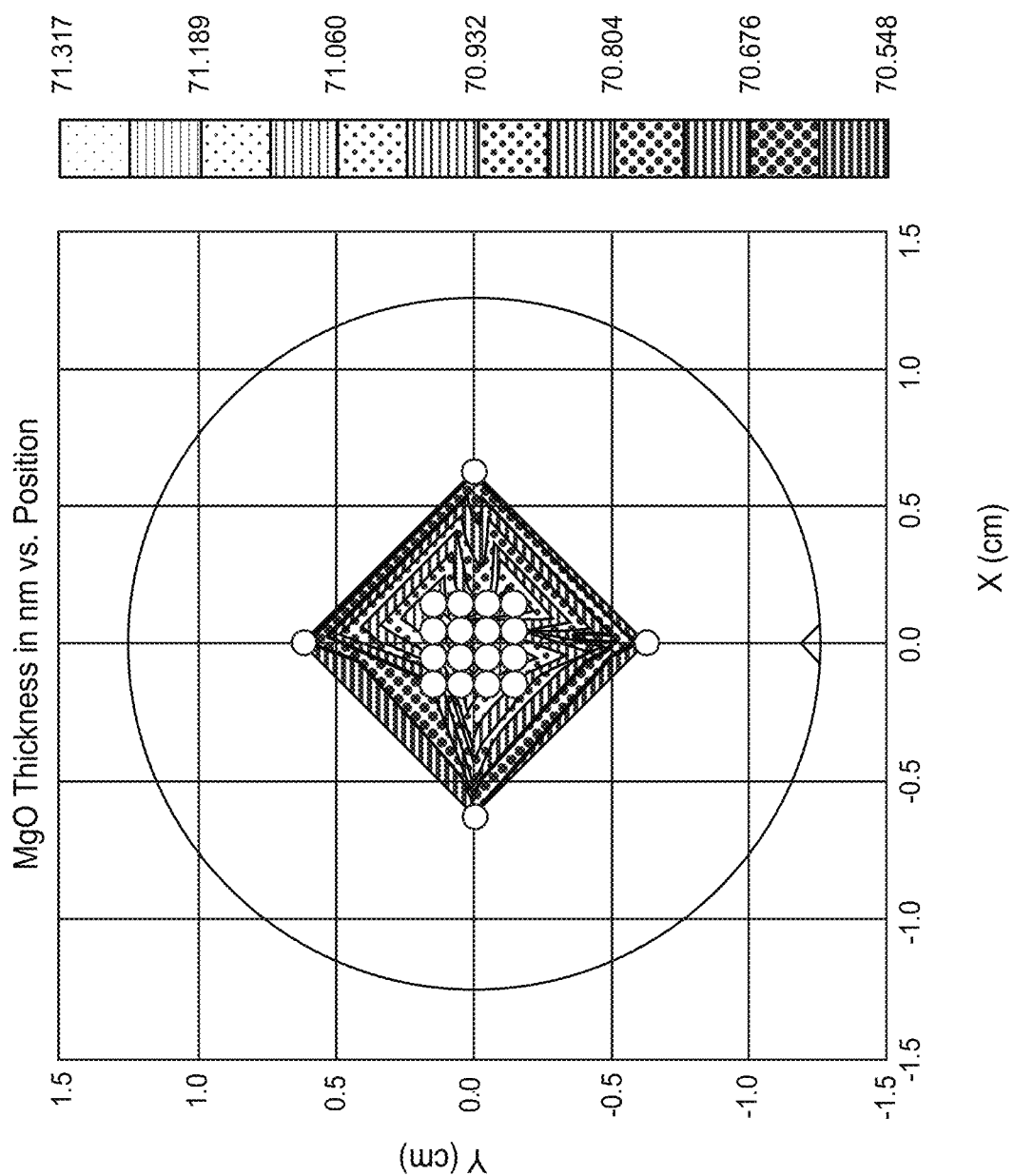
FIG. 48 is a diagram that illustrates exemplary wedge phantom ellipsometry measurement points.

FIG. 48 is a diagram that illustrates exemplary wedge phantom ellipsometry measurement points. In particular, the graph depicts magnesium oxide (MgO) thickness in nm versus x-coordinates and y-coordinates of the wedge shaped phantom front surface 644 coated with MgO. An ellipsometry analysis by an independent third-party provides confirmation of the thickness of the MgO coating for each optical phantom fabricated as well as the index of refraction and dispersion of the MgO coating. Dispersion is the phenomenon in which the index of refraction of a material is dependent on the wavelength of light. The ellipsometry measurements determine the refractive index at various wavelengths, thereby quantifying the dispersion. A measurement of thickness and refractive index is typically taken at twenty individual points for each of the phantoms to be measured. Usually, sixteen (16) measurement points are within 2 mm of the center of the face and four points offset 6 mm radially from center, with each point 90° apart. The measurement pattern shown in FIG. 48 is represented by sixteen (16) black dots arrayed in the center of the wedge phantom diagram and four points radially offset from the center.

FIG. 49 is a table listing exemplary phantom lipid layer thicknesses for nine sample wedge shaped optical phantoms 642 measured using exemplary ellipsometry along with corresponding biological lipid layer thicknesses. All measurements are recorded in nm, and include expected phantom thickness and optical path length. The thickness results were averaged for each wedge shaped optical phantom 642 to provide an average phantom thickness for each wedge shaped optical phantom 642. All index of refraction results were averaged to provide a global index of refraction for all the wedge shaped optical phantoms 642. Since the index of refraction is dependent on the material used and the processing parameters, no significant variability is expected from wedge to wedge. The phantom thickness measurements are shown in the table of FIG. 49. These phantom thicknesses were then converted back to lipid thicknesses using an optical path length method. The average measured index of refraction of the MgO layer was 1.711 for light of 589 nm wavelength, somewhat different than the expected value of 1.68 nm. Consistent measurement data for a phantom having a 52 nm MgO coating was not available due to physical limitations of ellipsometry when measuring relatively thin layers. Another complication that limits measurement consistency is variability in coating thickness over the front surface 644 of the wedge shaped optical phantom 642. However, since other measured phantom thicknesses were similar to expected thickness for other phantoms, an expected value is assumed to be accurate for the wedge shaped optical phantom 642 having the 52 nm MgO coating.

FIG. 50 is a table that presents a comparison of expected exemplary interference colors from optical phantoms and a theoretical model. Using the measured thickness and index of refraction data, the color expected to be returned by each of the phantoms when imaged by the OSI device was calculated. Values for the colors calculated are shown in the table of FIG. 50 using an 8-bit RGB format as well as a hue, chroma, and lightness format. The RGB values assume that the intensity of the incident light has been reduced to 55 percent of the intensity output by the illuminator under normal operation using the neutral density filter 629 (as shown in FIG. 44). The intensity adjustment was made to avoid saturation with the phantoms, since the amount of light returned from the phantoms is significantly higher in intensity than from a biological model. The intensity of the incident light does not affect hue. An intensity effect on chroma and lightness is accounted for in subsequent analysis.

Figure 51:
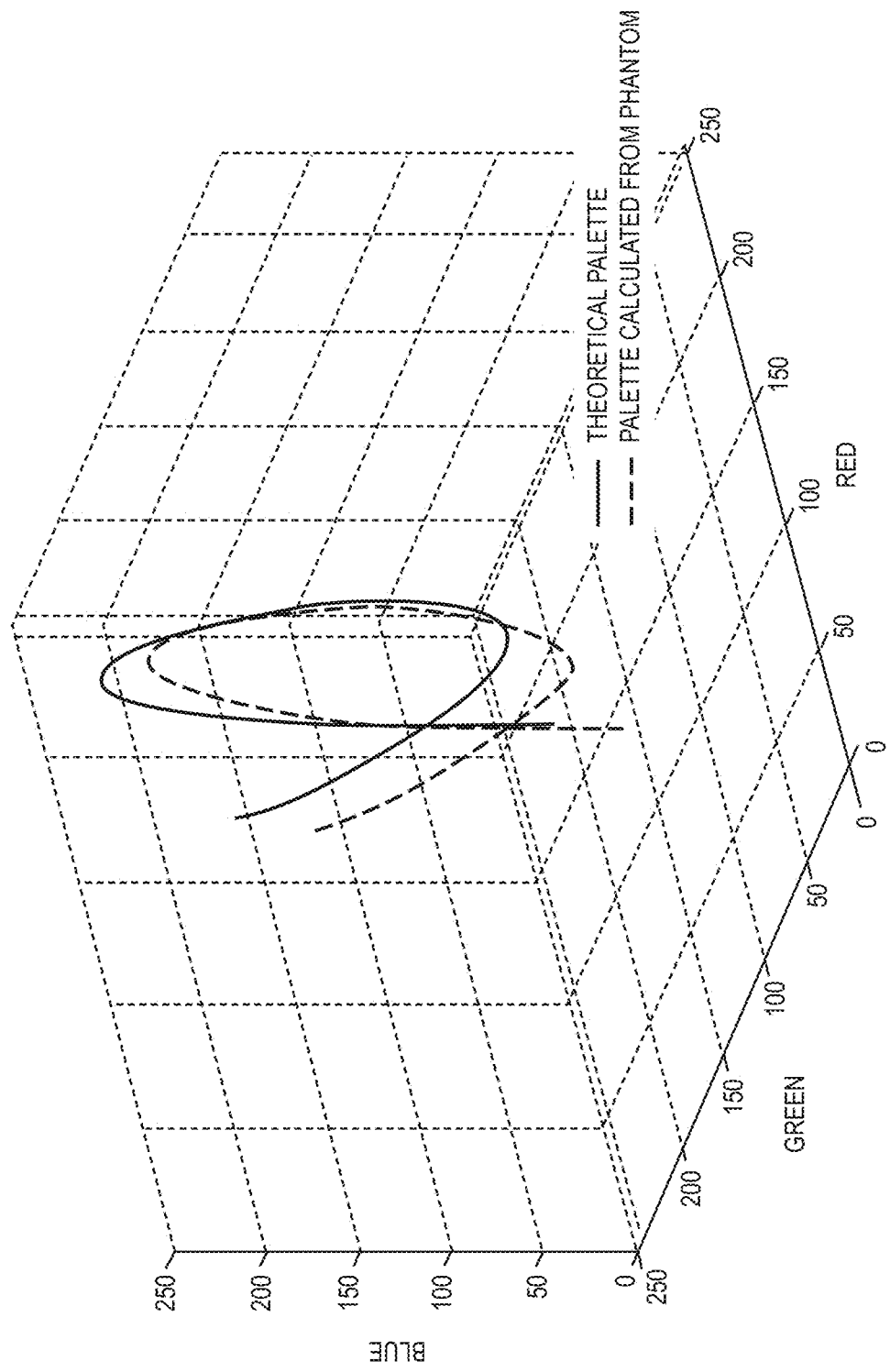
FIG. 51 is a graph that compares an original exemplary lipid color palette with a new exemplary lipid color palette based on the phantom measurements.

Colorimetric Analysis of Optical Phantom Measurements Recorded Using an OSI System One phantom of each thickness is placed in the imaging path of the imaging device 194 of the OSI device 170 (FIG. 44). A video is recorded for each phantom thickness and exported from the OSI device 170 in a multimedia container format such as an audio video interleave (avi) format. The videos are then imported into a numerical computing environment such as Matlab®, which is executed by the OSI device to perform frame subtraction and erode/dilate algorithms. A frame is isolated from each video and a region of interest is selected for each frame. A region of interest is located near the center of an illuminator tile to avoid any edge non-uniformity, and an attempt should be made to avoid any blemishes in the phantom coating. The average RGB values are then determined within the region of interest for a phantom of each thickness. A full color palette may then be created from 10 nm to 240 nm in 2 nm increments by fitting a cubic spline to the nine calculated lipid color values. FIG. 51 is a graph that compares an original lipid color palette with a new exemplary lipid color palette based on the phantom measurements listed in the table of FIG. 50.

The performances of the original exemplary palette and the new palette calculated from the optical phantoms were compared by analyzing sixty-one (61) videos captured using an OSI device like the OSI device 170. One frame was selected from each video and analyzed using both the theoretical palette and the phantom-derived palette. A conformance factor that is the ratio of pixels that were matched to the palette and the average distance between a matched pixel and the palette were computed for each of the frames using a software utility that includes a matching algorithm. The maximum acceptable distance between a pixel and the nearest location on the palette that was considered a match was 30 (in 8-bit RGB color space) for all points along both palettes. For the theoretical palette, the average conformance factor for the sixty-one (61) frames was 0.916, while the average distance to the palette was 15.05. For the phantom-derived palette, the average conformance factor was 0.995 while the average distance to the palette was 10.63. Using either metric, the phantom-derived palette demonstrated a relatively large improvement over the theoretical palette.

A set of optical phantoms using a convex lens substrate was made at the same time as the wedge shaped optical phantoms 642. A quality control procedure has been added to the OSI assembly process, wherein videos of convex shaped optical phantoms 652 having different thin film material thicknesses are captured. These videos are analyzed using the OSI device 170 to compare the captured images to the results obtained from the wedge shaped optical phantoms 642. The measured thickness is required to match the expected thickness to within 10 nm. This check ensures that both the optical and software systems of each OSI device 170 are operating correctly in conjunction with one another prior to shipment to customers. This test also conclusively demonstrates that the interferometric measurements provided by the OSI device 170 correlate to actual biological tear film thickness.

Although by example only a two wave model for an optical phantom such as the wedge shaped optical phantom 642 is described above, it should be understood that the optical phantoms of the present disclosure may be extended to a three wave model by adding another material layer. The added material layer for the three wave model would mimic or substantially mimic the lipid layer and aqueous layer interface.

Figure 52:
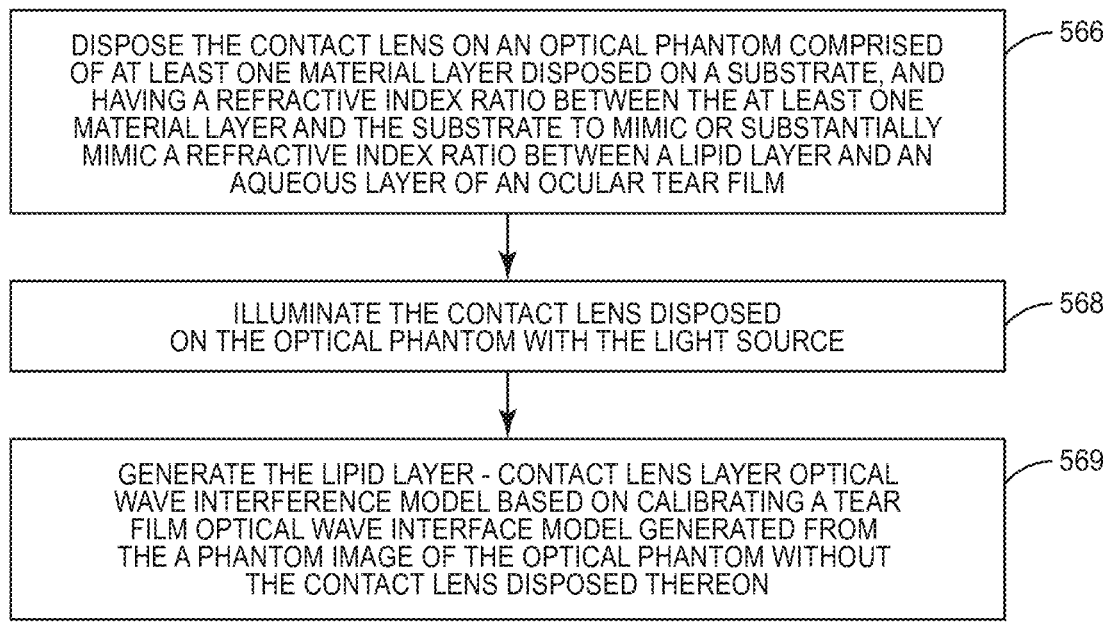
FIG. 52 is a flowchart of an exemplary process for determining a lipid-layer contact lens layer optical wave interference model based on calibrating a tear film optical wave interference model based on imaging a contact lens disposed on an optical phantom with the OSI device in FIG. 14 and analyzing the optical wave interference in the specularly reflected light returned from the contact lens disposed on the optical phantom.

Because the embodiments disclosed herein involve use of a lipid layer—contact lens layer interference model, it may be desired to employ the calibration techniques described above with regard to optical phantoms to calibrate a tear film interference model into a lipid layer—contact lens layer interference model instead of relying on a theoretical lipid layer—contact lens layer interference model. In this regard, FIG. 52 is a flowchart of an exemplary process for determining a lipid-layer—contact lens layer optical wave interference model based on calibrating a tear film optical wave interference model. The process is based on imaging a contact lens disposed on an optical phantom with the OSI device in FIG. 44 and analyzing the optical wave interference in the specularly reflected light returned from the contact lens disposed on the optical phantom. This also allows the lipid layer—contact lens layer optical wave interference model to be based specifically on the exact contact lens worn by the patient.

Figure 53:
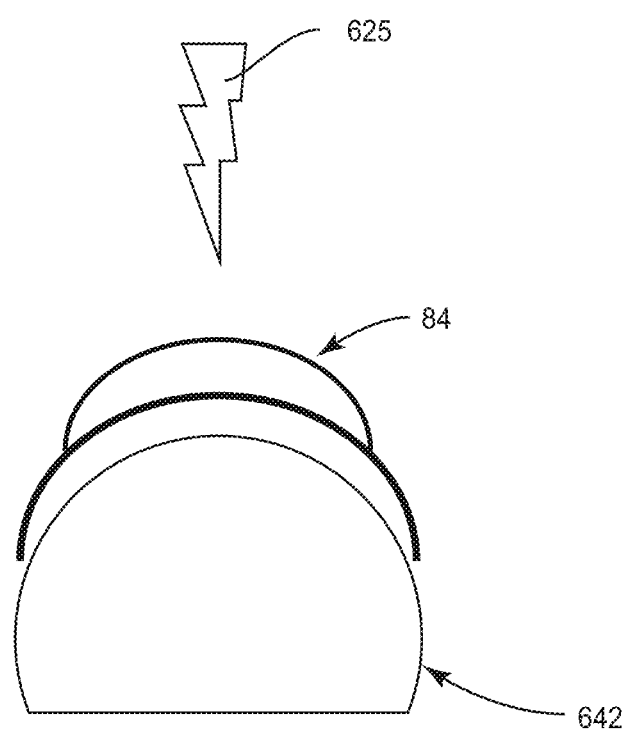
FIG. 53 is a schematic diagram of a contact lens disposed on an optical phantom.

In this regard, as illustrated in FIG. 52, the contact lens 84 that is worn by the patient is disposed on an optical phantom 642 (block 566), as shown in FIG. 53. The contact lens 84 may be rinsed to remove all lipids that may be present from previous wear by a patient prior to disposing on the optical phantom 642. FIG. 53 references elements in the OSI device 170 and calibration system in FIG. 44, previously described above. With the contact lens 84 disposed on the optical phantom 642 and in the optical path of the illuminator 173 of the OSI device 170, the contact lens 84 is illuminated by light 625 (see FIG. 44) (block 568 in FIG. 52). An image is obtained of the contact lens 84 and optical phantom 642 with no lipids present, which will produce a certain brightness due to the index or refraction and thickness of the contact lens 84 and optical phantom 642. The computer control system 240 can then generate a lipid layer—contact lens layer interference model based on the returned specularly reflected light versus what was expected for the tear film interference model. These differences can be used to generate the lipid-layer—contact lens layer interference by making changes to the index or refraction used for the aqueous layer in a tear film interference model (e.g., in the tear film interference model described above) that was calibrated based on the optical phantom 642 without the contact lens 84 disposed thereon, to adjust the color scale therein (block 569). Alternatively, each different contact lens 84 and variation may be stored in the OSI device 170, which can be selected if worn by a patient to generate the lipid layer—contact lens layer interference model to be used by the OSI device 170.

Figure 54:
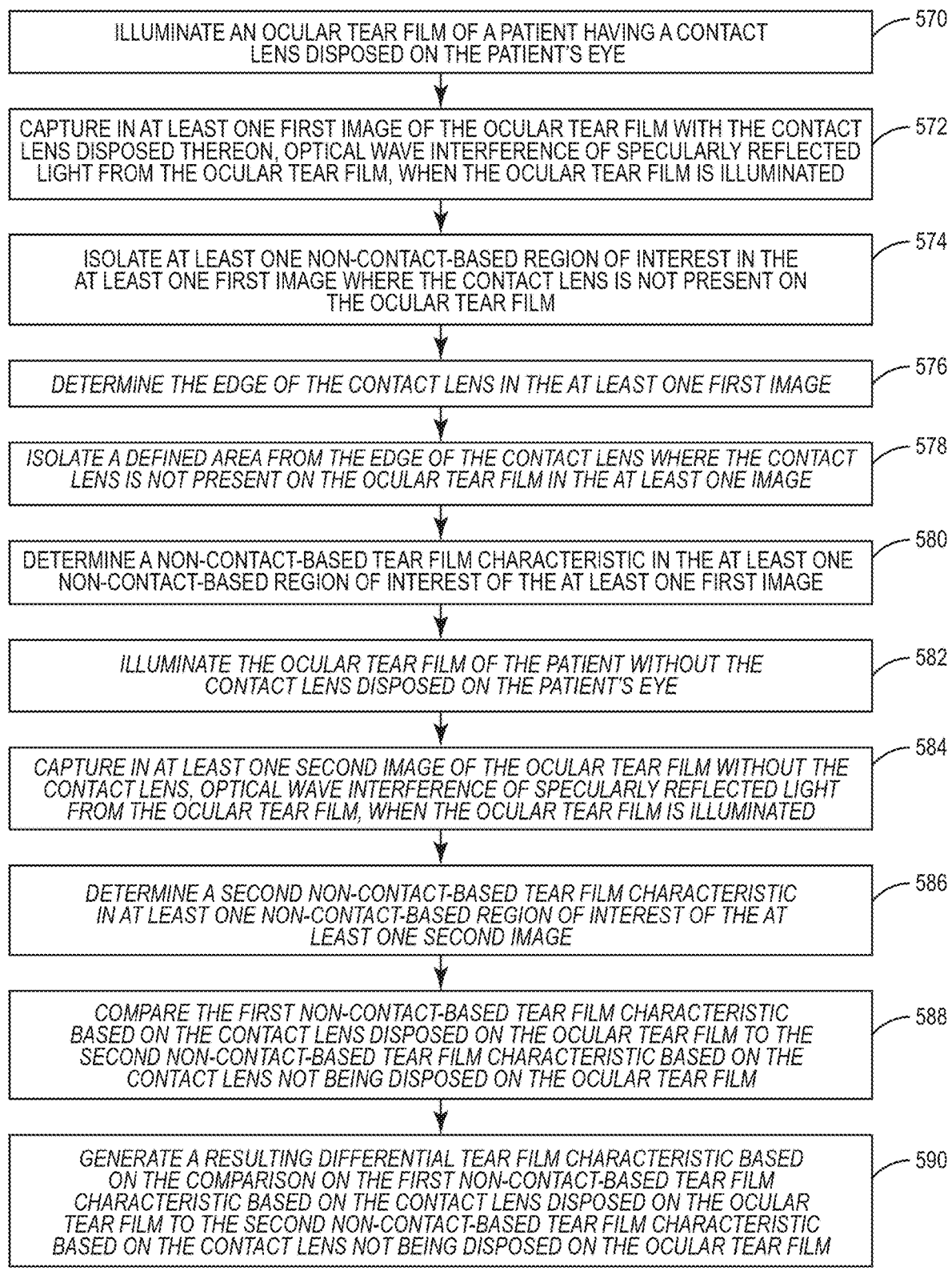
FIG. 54 is a flowchart of an exemplary process for determining tear film characteristics of a patient's ocular tear film based on analysis of a non-contact lens-based region of interest of an image of a patient's tear film during contact lens wear, to determine the patient's intolerance to contact lens wear.

Other processes for determining tear film characteristics of a contact lens wearing patient's tear film can be provided that do not require color-based analysis. For example, FIG. 54 is a flowchart of an exemplary process for determining tear film characteristics of a patient's ocular tear film based on analysis of a non-contact lens-based region of interest of an image of a patient's tear film during contact lens wear, to determine the patient's intolerance to contact lens wear. In this regard, in a first step, the patient's ocular tear film having a contact lens 84 disposed on the patient's eye is performed by the OSI device 30 in FIG. 14 (block 570). The imaging device in the OSI device 340 captures in at least one first image of the ocular tear film with the contact lens 84 disposed thereon, optical wave interference of specularly reflected light from the ocular tear film, when the ocular tear film is illuminated by the illuminator 36 (block 572). The computer control system 240 then isolates at least one non-contact lens-based region of interest in the at least one first image where the contact lens 84 is not present on the ocular tear film (block 574). As examples, as described above, the computer control system 240 may use edge analysis to determine the edge of the contact lens 84 in the at least one first image (block 576) and isolate a defined area from the edge of the contact lens 84 where the contact lens 84 is not present on the ocular tear film in the at least one image (block 578). For example, with a contact lens 84 in place, a tear film build up on the surface of the schlera or eye surface immediately adjacent to the contact lens 84 may occur and be detectable in the captured image of the tear film. The computer control system 240 can then determine a non-contact lens-based tear film characteristic in the at least one non-contact lens-based region of interest of the at least one first image (block 580). Note that the tear film characteristic does not have to be limited to obtaining a color-based value of the tear film in the captured image.

With continuing reference to FIG. 54, additional optical steps can be performed. In this regard, the patient may be instructed to remove the contact lens 84 from their eye to obtain an image of the ocular tear film without the contact lens 84 for comparison purposes. In this regard, the computer controls system 240 causes the illuminator 173 in the OSI device 170 to illuminate the ocular tear film of the patient without the contact lens 84 disposed on the patient's eye (block 582). The imaging device 40 captures in at least one second image of the ocular tear film without the contact lens 84, optical wave interference of specularly reflected light from the ocular tear film, when the ocular tear film is illuminated (block 584). The computer control system 240 then determines a second non-contact lens-based tear film characteristic in at least one non-contact lens-based region of interest of the at least one second image (block 586). The computer control system 240 then can compare the first non-contact lens-based tear film characteristic based on the contact lens 84 disposed on the ocular tear film to the second non-contact lens-based tear film characteristic based on the contact lens 84 not being disposed on the ocular tear film (block 588). The computer control system 240 can then generate a resulting differential tear film characteristic based on the comparison of the first non-contact lens-based tear film characteristic based on the contact lens 84 disposed on the ocular tear film to the second non-contact lens-based tear film characteristic based on the contact lens 84 not being disposed on the ocular tear film (block 590).

Further, a contact lens wearing patient's tear film without a contact lens described above can be analyzed immediately after the imaging of the patient's tear film with the contact lens disposed on the eye, or after a period of time, for example 1 to 8 hours later. The imaging of the patient's tear film with and/or without contact lens wear can be performed over a period of time with blinking involved, where the blinking images can be removed if desired, as discussed above. The patient may be informed to conduct a series of forceful blinks to stabilize the tear film before imaging of the tear film is performed and/or wear the contact lens in the office for a prescribed period of time before imaging occurs. This amount of time can be as short as 2 minutes and as long as 30 minutes as non-limiting examples. The OSI device can be used to determine the change in tear film characteristics during the session and over time, with and without contact lens wear to determine the patient's tolerance or intolerance to contact lens wear as such pertains to tear film.

Tear film characteristics of a contact lens wearing patient can be stored and sorted in a database, when desired, in the OSI device 30 over a period of times and analysis sessions to determine the change in tear film characteristics and for further analysis. Changes may occur due to increased contact lens wear or reduced contact lens wear, as examples.

Many modifications and other embodiments of the disclosure set forth herein will come to mind to one skilled in the art to which the disclosure pertains having the benefit of the teachings presented in the foregoing descriptions and the associated drawings. These modifications include, but are not limited to, the type of light source or illuminator, the number of tiling groups and modes, the arrangement of tile groups, the type of imaging device, image device settings, the relationship between the illuminator and an imaging device, the control system, the type of tear film interference model, and the type of electronics or software employed therein, the display, the data storage associated with the OSI device for storing information, which may also be stored separately in a local or remotely located remote server or database from the OSI device, any input or output devices, settings, including pre-processing and post-processing settings, materials selected for phantoms, etc. . . . . . Note that subtracting the second image from the first image as disclosed herein includes combining the first and second images, wherein like signals present in the first and second images are cancelled when combined. Further, the present disclosure is not limited to illumination of any particular area on the patient's tear film or use of any particular color value representation scheme.

Therefore, it is to be understood that the disclosure is not to be limited to the specific embodiments disclosed and that modifications and other embodiments are intended to be included within the scope of the appended claims. It is intended that the present disclosure cover the modifications and variations of this disclosure provided they come within the scope of the appended claims and their equivalents. Although specific terms are employed herein, they are used in a generic and descriptive sense only and not for purposes of limitation.

We claim:
1. An apparatus for diagnosing contact lens intolerance on an ocular tear film of a patient, comprising:
    a light source configured to illuminate the ocular tear film of the patient with a contact lens disposed on a patient's eye;
    an imaging device configured to capture in at least one first image of the ocular tear film with the contact lens disposed on the patient's eye, optical wave interference of specularly reflected light from the ocular tear film, when the ocular tear film is illuminated with the light source; and a computer control system configured to:
isolate at least one contact lens-based region of interest in the at least one first image where the contact lens is present on the ocular tear film;
convert the at least one contact lens-based region of interest in the at least one first image into at least one contact lens-based color-based value;
compare the at least one contact lens-based color-based value to a lipid layer—contact lens layer optical wave interference model; and
determine a contact lens-based tear film characteristic of the at least one contact lens-based region of interest of the ocular tear film based on the comparison of the at least one contact lens-based color-based value to the lipid layer—contact lens layer optical wave interference model,
wherein the computer control system is configured to determine the contact lens-based tear film characteristic by being configured to measure a tear film layer thickness of the at least one contact lens-based region of interest in the at least one first image based on the comparison of the at least one contact lens-based color-based value to the lipid layer—contact lens layer optical wave interference model.

2. The apparatus of claim 1, wherein the computer control system is further configured to:
isolate at least one non-contact lens-based region of interest in the at least one first image where the contact lens is not present on the ocular tear film;
convert the at least one non-contact lens-based region of interest in the at least one first image into at least one first non-contact lens-based color-based value;
compare the at least one first non-contact lens-based color-based value to a tear film layer optical wave interference model; and
determine a non-contact lens-based tear film characteristic of the at least one non-contact lens-based region of interest in the at least one first image based on the comparison of the at least one first non-contact lens-based color-based value to the tear film layer optical wave interference model.

3. The apparatus of claim 2, further comprising a visual display configured to display the at least one non-contact lens-based region of interest in the at least one first image where the contact lens is present on the ocular tear film.

4. The apparatus of claim 2, wherein the computer control system is further configured to:
determine a difference between the contact lens-based tear film characteristic to the non-contact lens-based tear film characteristic; and
generate a resulting differential tear film characteristic based on the determined difference between the contact lens-based tear film characteristic to the non-contact lens-based tear film characteristic.

5. The apparatus of claim 2, wherein the computer control system is configured to isolate the at least one non-contact lens-based region of interest in the at least one first image where the contact lens is not present by being configured to:
determine an edge of the contact lens in the at least one first image; and
isolate a defined area from the edge of the contact lens where the contact lens is not present on the ocular tear film in the at least one first image.

6. The apparatus of claim 5, wherein the computer control system is further configured to determine a slope of a meniscus of the ocular tear film in the at least one contact lens-based region of interest of the ocular tear film based on the comparison of the at least one contact lens-based color-based value to the lipid layer—contact lens layer optical wave interference model.

7. The apparatus of claim 1, wherein the computer control system is further configured to determine a viscosity of the ocular tear film in the at least one contact lens-based region of interest in the at least one first image based on the comparison of the at least one contact lens-based color-based value to the lipid layer—contact lens layer optical wave interference model.

8. The apparatus of claim 1, wherein the computer control system is further configured to determine a movement rate of the ocular tear film in the at least one contact lens-based region of interest in the at least one first image based on the comparison of the at least one contact lens-based color-based value to the lipid layer—contact lens layer optical wave interference model.

9. The apparatus of claim 1, wherein the computer control system is further configured to determine at least one of a size, a shape, a breakup, a breakup time, or a disappearance of the ocular tear film in the at least one contact lens-based region of interest in the at least one first image based on the comparison of the at least one contact lens-based color-based value to the lipid layer—contact lens layer optical wave interference model.

10. The apparatus of claim 1, wherein the computer control system is further configured to:
determine a type of contact lens disposed on the patient's eye; and
generate the lipid layer—contact lens layer optical wave interference model based on the determined type of contact lens.

11. The apparatus of claim 10, wherein the contact lens is disposed on an optical phantom comprised of at least one material layer disposed on a substrate, and having a refractive index ratio between the at least one material layer and the substrate to mimic or substantially mimic a refractive index ratio between a lipid layer and an aqueous layer of the ocular tear film;
wherein the computer control system is further configured to:
illuminate the contact lens disposed on the optical phantom with the light source; and
generate the lipid layer—contact lens layer optical wave interference model based on calibrating a tear film optical wave interface model generated from a phantom image of the optical phantom without the contact lens disposed thereon.

12. The apparatus of claim 1, wherein the light source is comprised of a multi-wavelength Lambertian light source.

13. The apparatus of claim 1, wherein the light source is comprised of a mono-chromatic light source.

14. The apparatus of claim 1, further comprising a visual display configured to display the at least one first image.

15. The apparatus of claim 1, further comprising a visual display configured to display the at least one contact lens-based region of interest in the at least one first image where the contact lens is present on the ocular tear film.

16. The apparatus of claim 1, wherein:
the light source is further configured to illuminate the ocular tear film of the patient without a contact lens disposed on the patient's eye;
the imaging device is further configured to capture in at least one second image of the ocular tear film without the contact lens disposed on the patient's eye, optical wave interference of specularly reflected light from the ocular tear film, when the ocular tear film is illuminated with the light source; and the computer control system is further configured to compare the at least one first image and the at least one second image to determine a difference in a tear film characteristic based on whether the contact lens is disposed on the patient's eye.

17. An apparatus for diagnosing contact lens intolerance on an ocular tear film of a patient, comprising:

a light source configured to illuminate the ocular tear film of the patient without a contact lens disposed on a patient's eye;

an imaging device configured to:
capture in at least one first image of the ocular tear film without the contact lens disposed on the patient's eye, optical wave interference of specularly reflected light from the ocular tear film, when the ocular tear film is illuminated with the light source; and capture a background signal from the ocular tear film with the contact lens disposed on the patient's eye in at least one background image; and a computer control system configured to:
subtract the at least one background image from the at least one first image to generate at least one resulting image containing the optical wave interference of specularly reflected light from the ocular tear film with the background signal removed or reduced;

isolate at least one contact lens-based region of interest in the at least one resulting image where the contact lens is present on the ocular tear film;

convert the at least one contact lens-based region of interest in the at least one resulting image into at least one contact lens-based color-based value;

compare the at least one contact lens-based color-based value to a lipid layer —contact lens layer optical wave interference model; and determine a contact lens-based tear film characteristic of the at least one contact lens-based region of interest of the ocular tear film based on the comparison of the at least one contact lens-based color-based value to the lipid layer—contact lens layer optical wave interference model.

18. The apparatus of claim 17, wherein the imaging device is further configured to capture the at least one background image when the light source is not illuminating the ocular tear film.

19. The apparatus of claim 17, wherein the imaging device is further configured to capture the at least one background image when the light source is illuminating the ocular tear film.

20. The apparatus of claim 17, wherein the imaging device is further configured to capture the background signal from the ocular tear film in the at least one background image and not capture specularly reflected light from the ocular tear film.

21. An apparatus for diagnosing contact lens intolerance in a patient, comprising:

an illuminator configured to illuminate an ocular tear film of the patient having a contact lens disposed on a patient's eye;

an imaging device configured to capture in at least one first image of the ocular tear film with the contact lens disposed on the patient's eye, optical wave interference of specularly reflected light from the ocular tear film, when the ocular tear film is illuminated; and a computer control system configured to:
isolate at least one non-contact lens-based region of interest in the at least one first image where the contact lens is not present on the ocular tear film; and determine a non-contact lens-based tear film characteristic in the at least one non-contact lens-based region of interest of the at least one first image, wherein the computer control system is configured to isolate the at least one non-contact lens-based region of interest in the at least one first image where the contact lens is not present on the ocular tear film by being configured to:

determine an edge of the contact lens in the at least one first image; and isolate a defined area from the edge of the contact lens where the contact lens is not present on the ocular tear film in the at least one first image.

22. The apparatus of claim 21, wherein the computer control system is further configured to determine a slope of a meniscus of the ocular tear film in the at least one non-contact lens-based region of interest of the ocular tear film.

23. The apparatus of claim 22, wherein the computer control system is further configured to:
convert the at least one non-contact lens-based region of interest in the at least one first image into at least one first non-contact lens-based color-based value; and compare the at least one first non-contact lens-based color-based value to a tear film layer optical wave interference model.

24. The apparatus of claim 21, wherein:
the illuminator is configured to illuminate the ocular tear film of the patient without the contact lens disposed on the patient's eye;

the imaging device is further configured to capture in at least one second image of the ocular tear film without the contact lens disposed on the patient's eye, optical wave interference of specularly reflected light from the ocular tear film, when the ocular tear film is illuminated; and the computer control system is further configured to determine a second non-contact lens-based tear film characteristic in the at least one non-contact lens-based region of interest of the at least one second image.

25. The apparatus of claim 24, wherein the computer control system is further configured to compare the non-contact lens-based tear film characteristic based on the contact lens disposed on the patient's eye to the second non-contact lens-based tear film characteristic based on the contact lens not being disposed on the patient's eye.

26. The apparatus of claim 25, wherein the computer control system is further configured to generate a resulting differential tear film characteristic based on the comparison of the non-contact lens-based tear film characteristic based on the contact lens disposed on the patient's eye to the second non-contact lens-based tear film characteristic based on the contact lens not being disposed on the patient's eye.

27. The apparatus of claim 25, wherein the computer control system is further configured to compare the non-contact lens-based tear film characteristic to the second non-contact lens-based tear film characteristic by being configured to subtract the non-contact lens-based tear film characteristic from the second non-contact lens-based tear film characteristic.

* * * * *